United States Patent
Izumori et al.

(10) Patent No.: US 8,389,248 B2
(45) Date of Patent: Mar. 5, 2013

(54) DEOXYKETOHEXOSE ISOMERASE AND METHOD FOR PRODUCING DEOXYHEXOSE AND DERIVATIVE THEREOF USING SAME

(75) Inventors: Ken Izumori, Kagawa (JP); Masaaki Tokuda, Kagawa (JP); George Fleet, Oxford (GB); Yoshio Tsujisaka, Kagawa (JP); Kei Takeshita, Kagawa (JP); Keiji Tsusaki, Okayama (JP); Kazuhiro Okuma, Itami (JP)

(73) Assignees: National University Corporation Kagawa University, Takamatsu-shi (JP); Rare Sugar Production Technical Research Laboratories, LLC., Kita-gun (JP); Hayashibara Co., Ltd., Okayama (JP); Matsutani Chemical Industry Co., Ltd., Itami-shi (JP)

( * ) Notice: Subject to any disclaimer, the term of this patent is extended or adjusted under 35 U.S.C. 154(b) by 650 days.

(21) Appl. No.: 12/515,605

(22) PCT Filed: Nov. 20, 2007

(86) PCT No.: PCT/JP2007/072442
§ 371 (c)(1),
(2), (4) Date: Nov. 9, 2009

(87) PCT Pub. No.: WO2008/062780
PCT Pub. Date: May 29, 2008

(65) Prior Publication Data
US 2010/0105885 A1    Apr. 29, 2010

(30) Foreign Application Priority Data
Nov. 20, 2006  (JP) ................. 2006-313671

(51) Int. Cl.
*C12P 19/24*    (2006.01)
*C12N 9/90*    (2006.01)
(52) U.S. Cl. ............... 435/94; 435/280; 435/233

(58) Field of Classification Search .............. None
See application file for complete search history.

(56) References Cited

U.S. PATENT DOCUMENTS

| | | | |
|---|---|---|---|
| 5,411,880 A * | 5/1995 | Izumori et al. | ........... 435/233 |
| 5,679,562 A | 10/1997 | Izumori et al. | |
| 2006/0148061 A1 | 7/2006 | Izumori et al. | |

FOREIGN PATENT DOCUMENTS

| | | |
|---|---|---|
| EP | 0107652 B1 | 7/1987 |
| JP | 2006-515883 A | 6/2006 |
| WO | 2004/062604 A2 | 7/2004 |
| WO | 2004/063369 A1 | 7/2004 |

OTHER PUBLICATIONS

Gullapalli et al. Tetrahedron Letters, vol. 51, pp. 895-898, 2010.*
M. Mori et al., "New Syntheses of 6-Deoxy-L-gulose and 6-Deoxy-L-talose", Chem. Pharm. Bull., 1986, pp. 4037-4044, vol. 34, No. 10. (Cited in ISR).
T. W. Rademacher et al., "Glycobiology", Ann. Rev. Biochem., 1988, pp. 785-838, vol. 57. (Cited in spec).
T. Reichstein et al., "The Sugars of the Cardiac Glycosides", Adv. Carbohydr. Chem. 1962, pp. 65-120, vol. 17.

* cited by examiner

*Primary Examiner* — Richard Hutson
(74) *Attorney, Agent, or Firm* — Westerman, Hattori, Daniels & Adrian, LLP

(57) ABSTRACT

Providing 1- or 6-deoxy products corresponding to all of aldohexoses, ketohexoses and sugar alcohols, as based on Deoxy-Izumoring, as well as a method for systematically producing those products. A method for producing deoxyketohexose and a derivative thereof using a deoxyketohexose isomerase derived from *Pseudomonas cichorii* ST-24 (FERM BP-2736), comprising epimerizing 1-deoxy D-ketohexose or 6-deoxy D-ketohexose or 1-deoxy L-ketohexose or 6-deoxy L-ketohexose at position 3 to produce the individually corresponding 1-deoxy D-ketohexose or 6-deoxy D-ketohexose or 1-deoxy L-ketohexose or 6-deoxy L-ketohexose as an intended product.

13 Claims, 50 Drawing Sheets

[Fig.1]
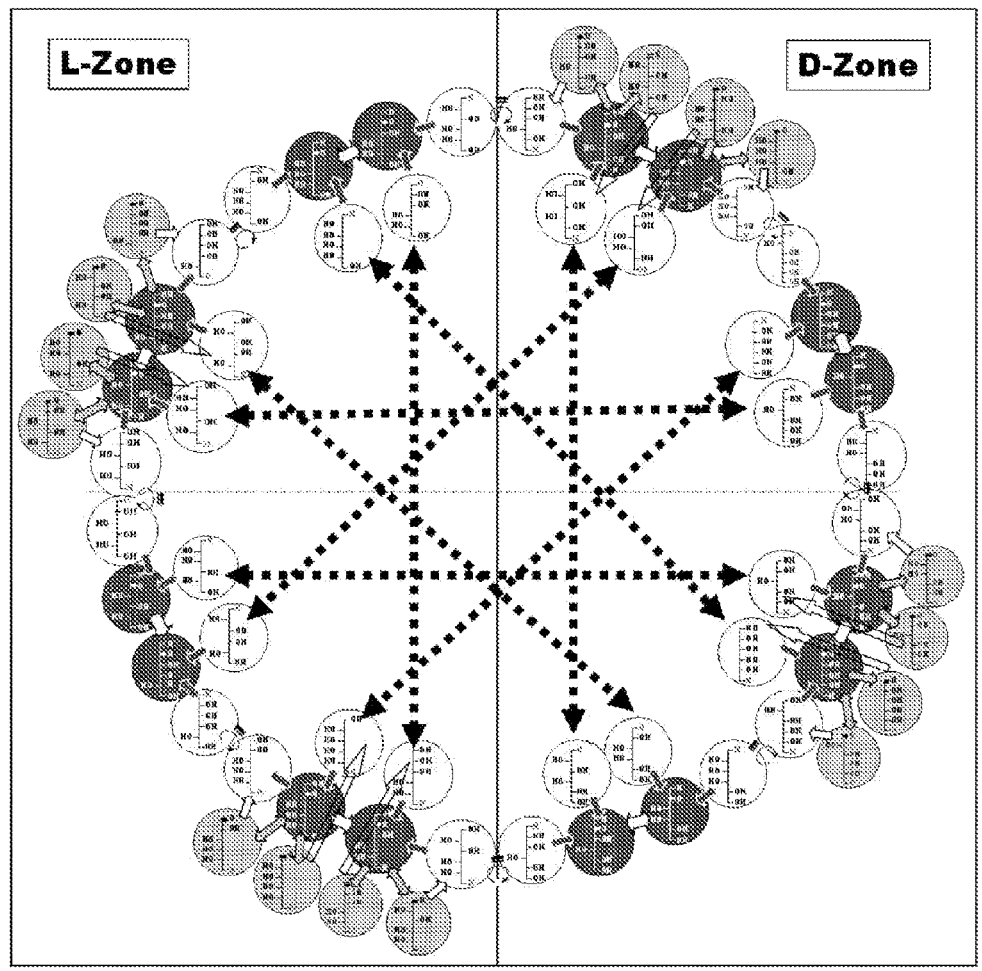
⇔ D-Tagatose 3-epimerase
⇔ Aldose isomerase
⇔ Polyol dehydrogenase
⇨ Aldose reductase
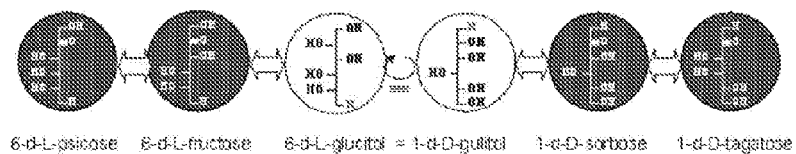

[Fig.2]
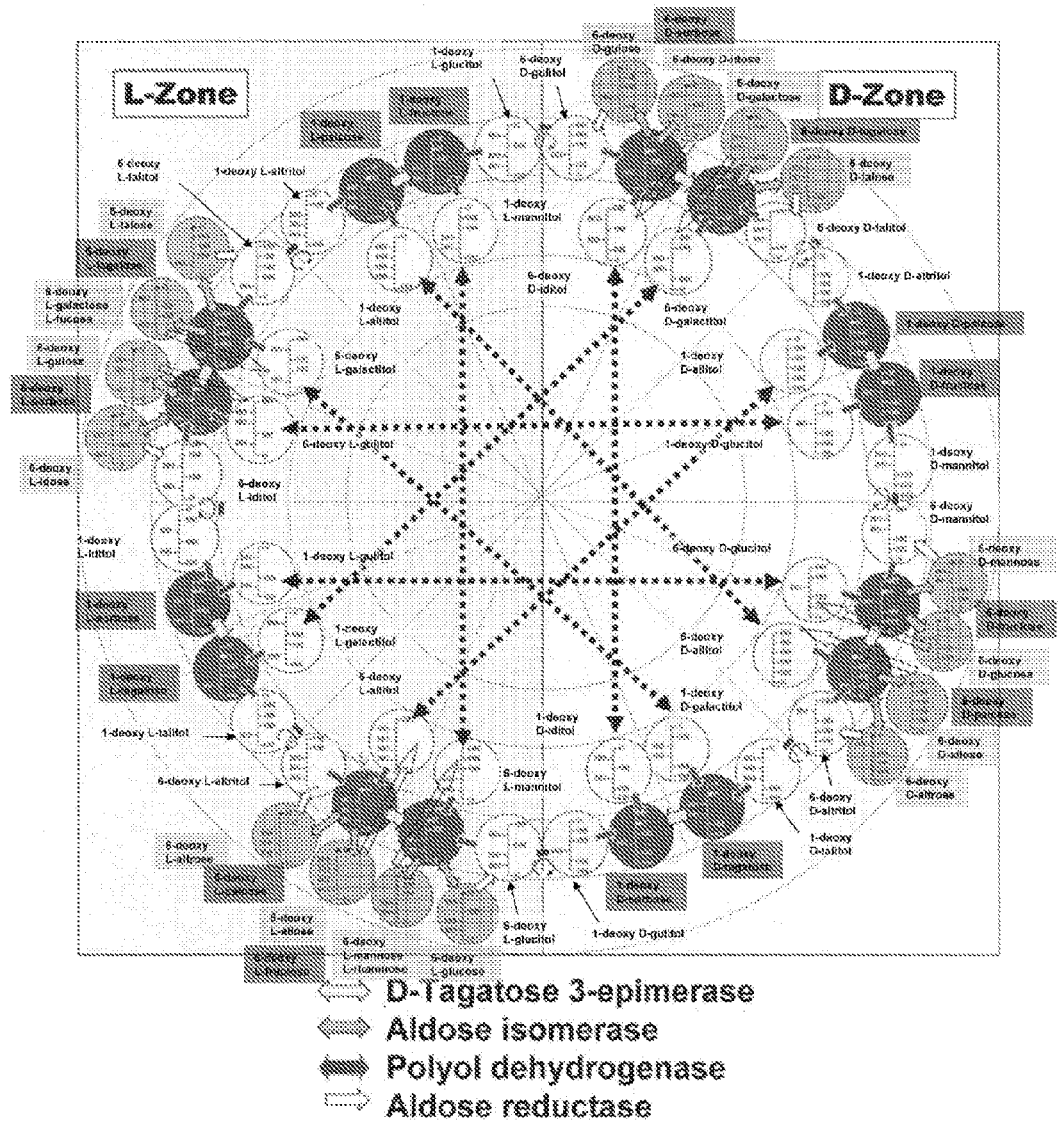

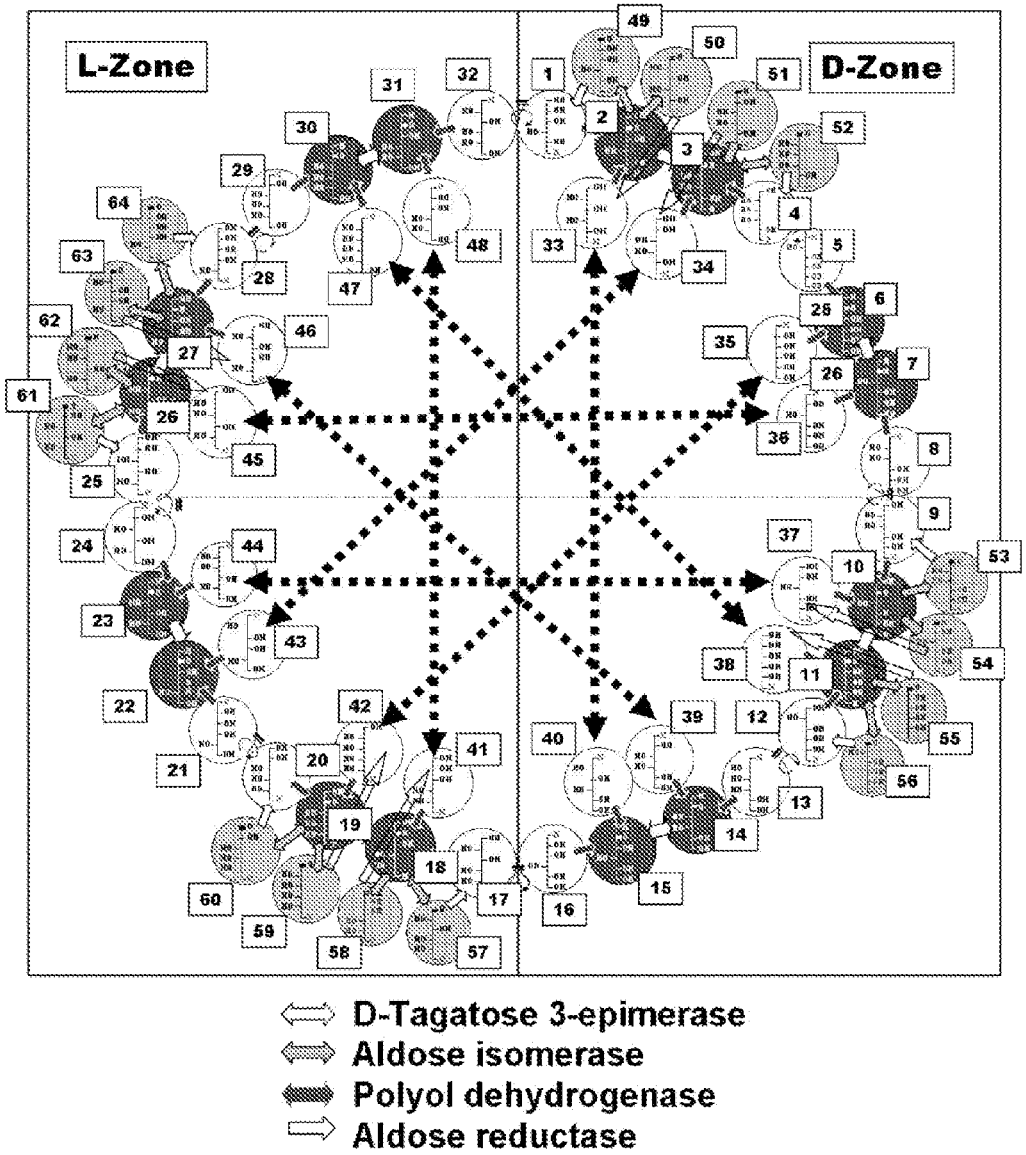
[Fig.3]
⇨ D-Tagatose 3-epimerase
⇨ Aldose isomerase
⇨ Polyol dehydrogenase
⇨ Aldose reductase

[Fig.4]
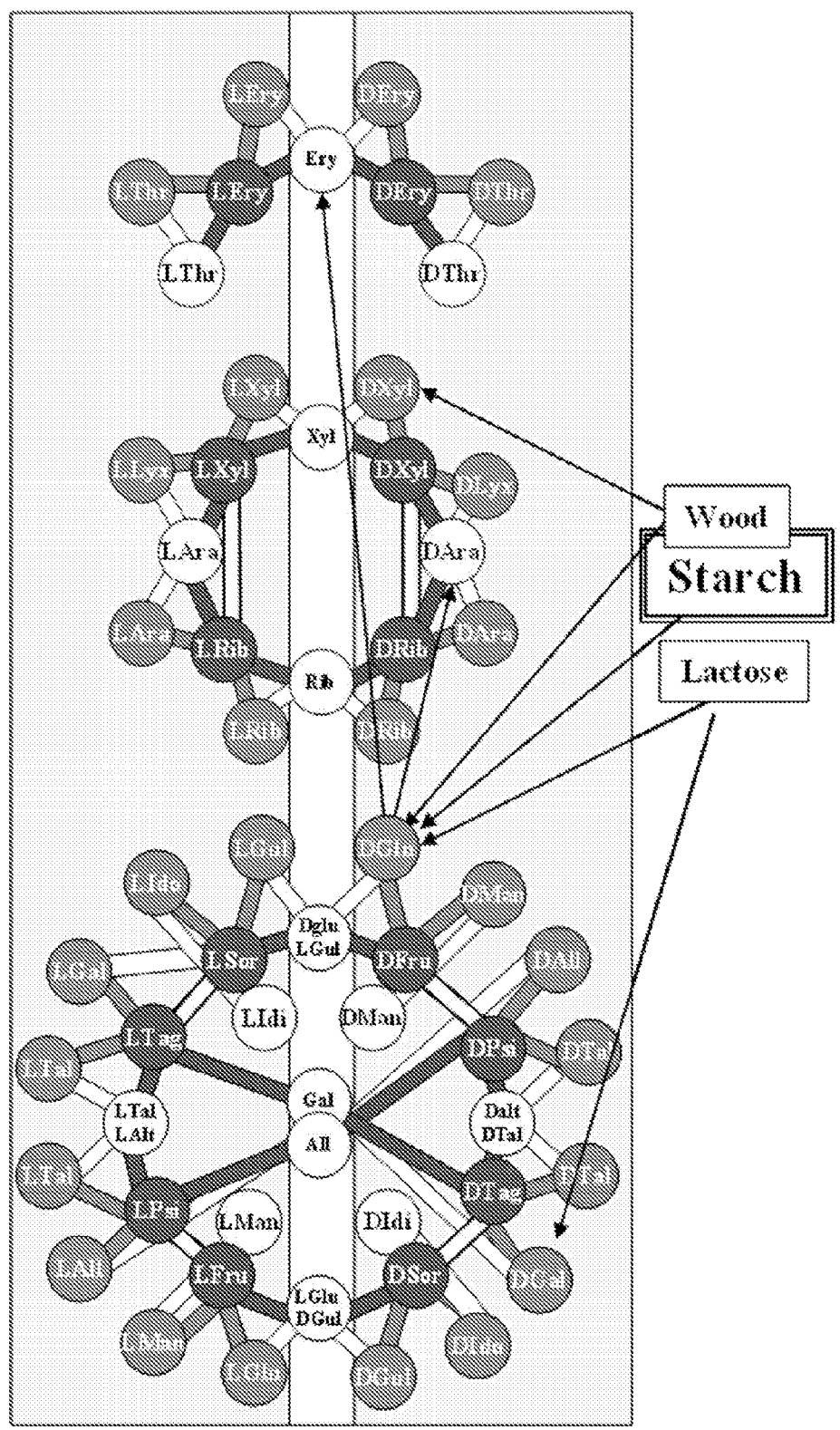

[Fig.5]
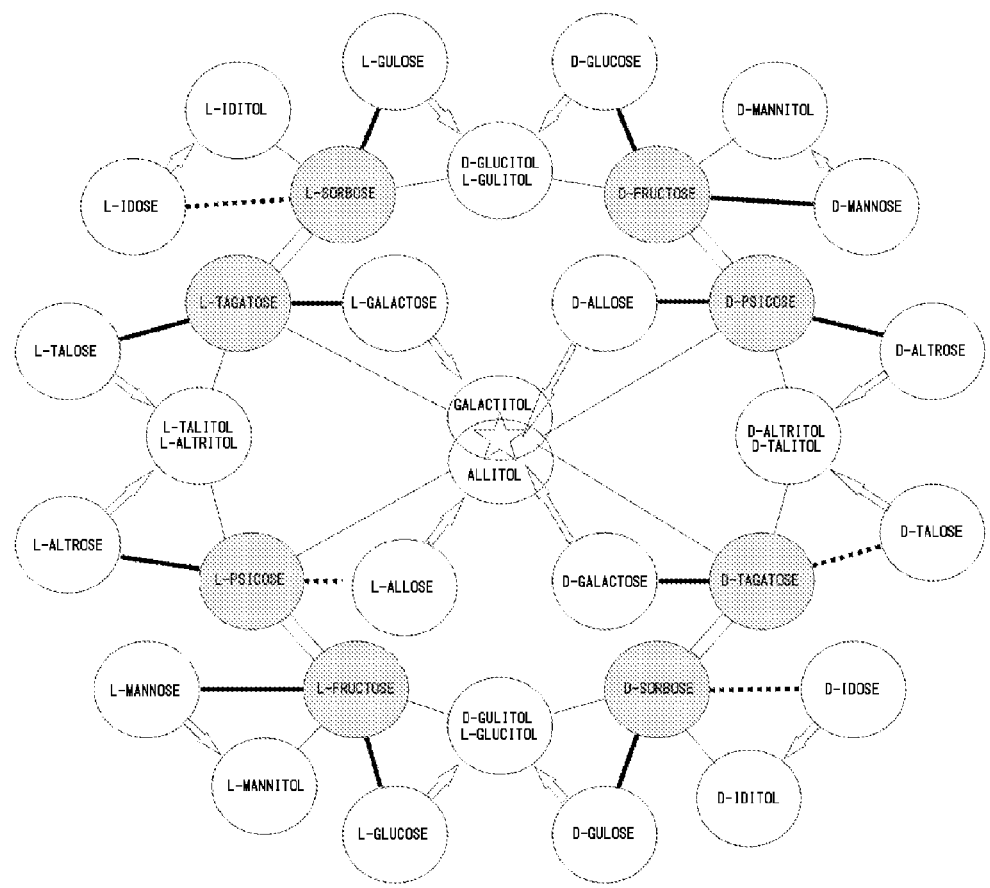

[Fig.6]
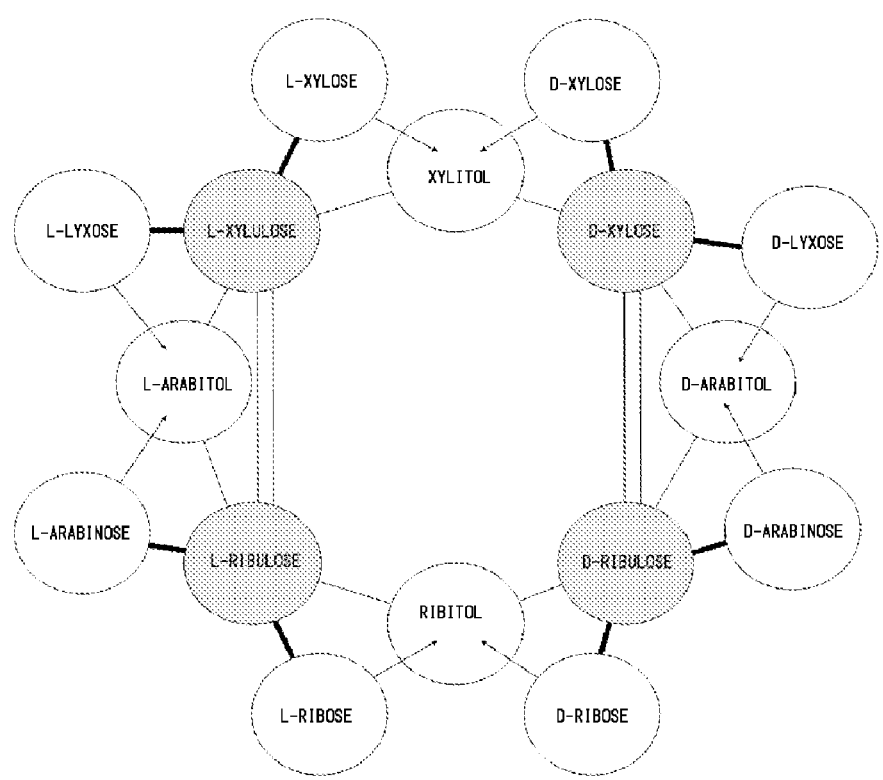

[Fig.7]
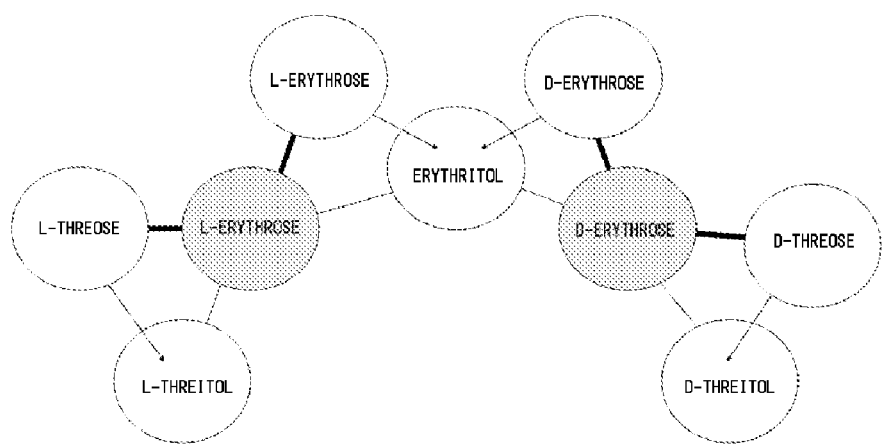

[Fig.8]
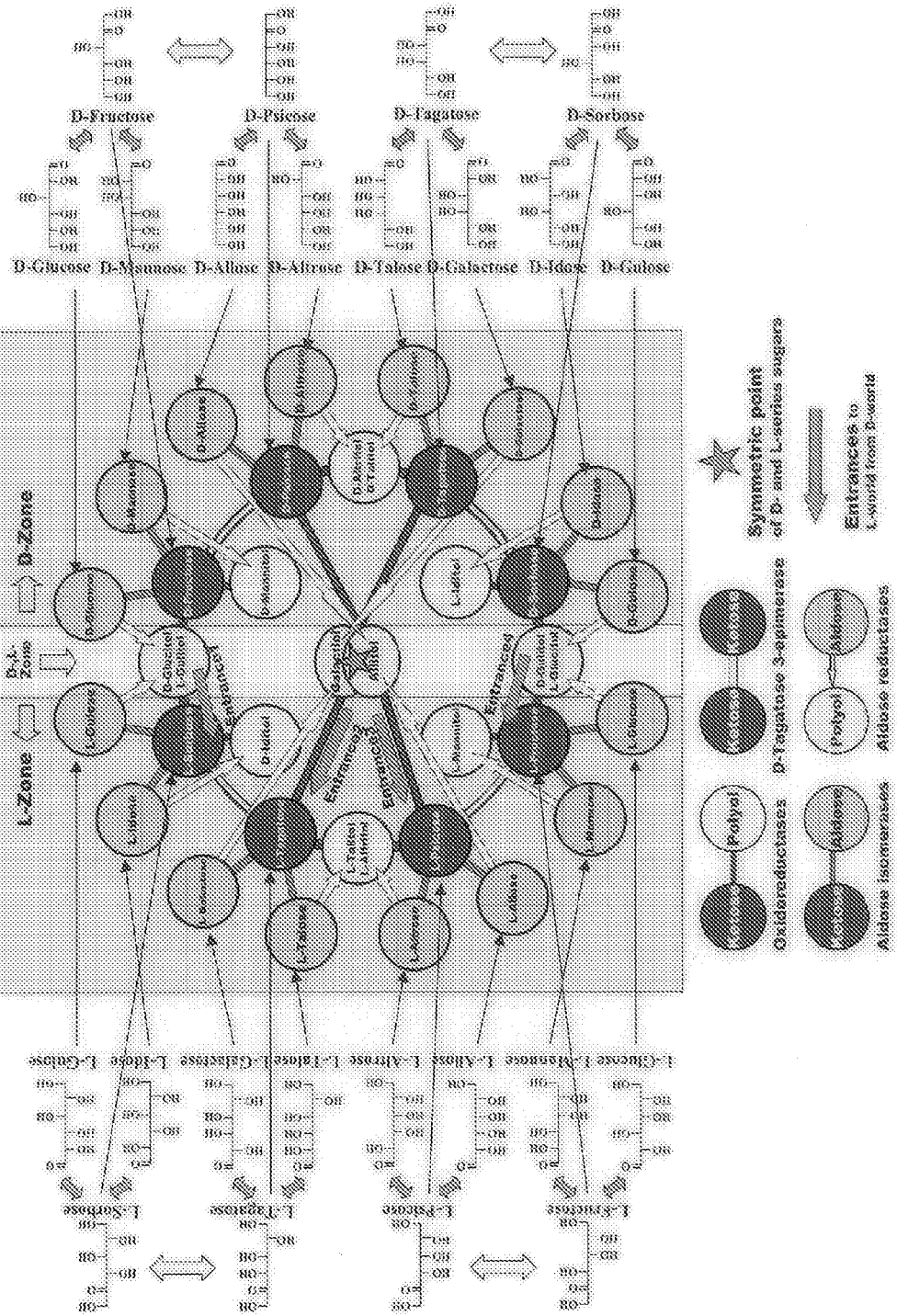

[Fig.9]
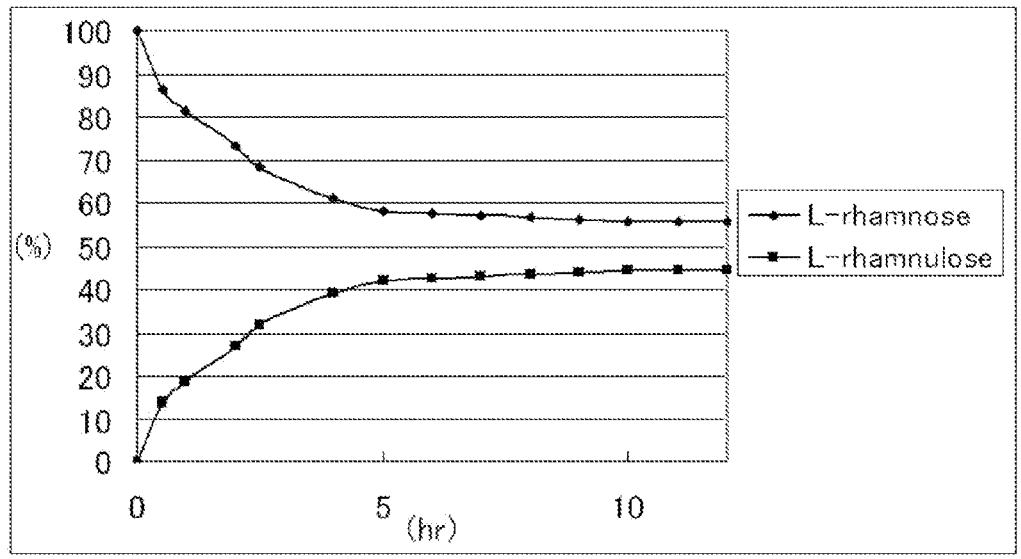
[Fig.10]
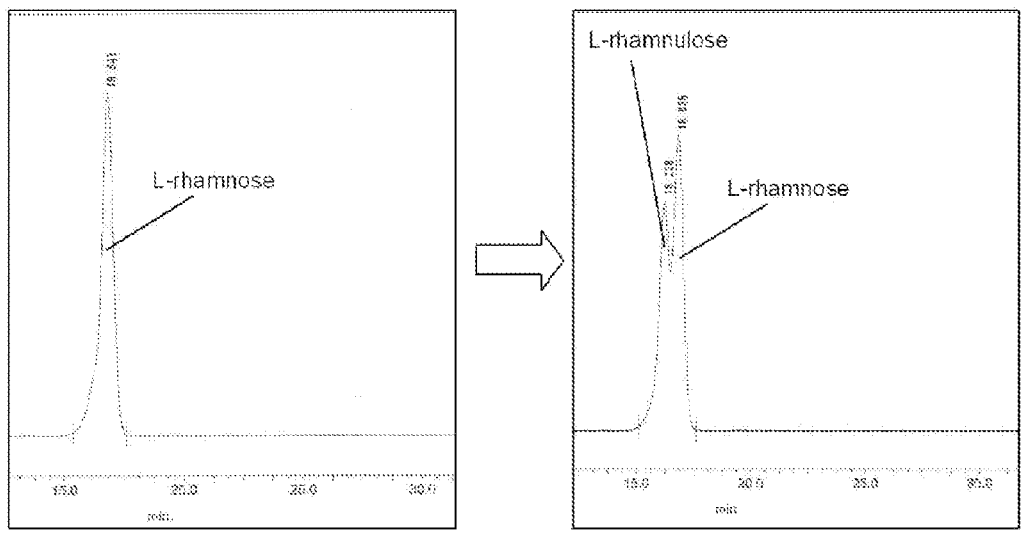

[Fig.11]
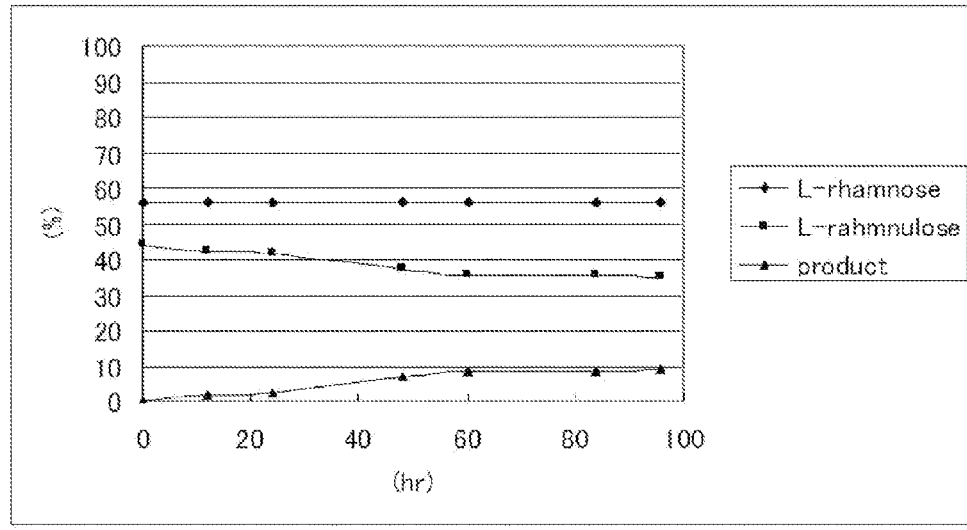
[Fig.12]
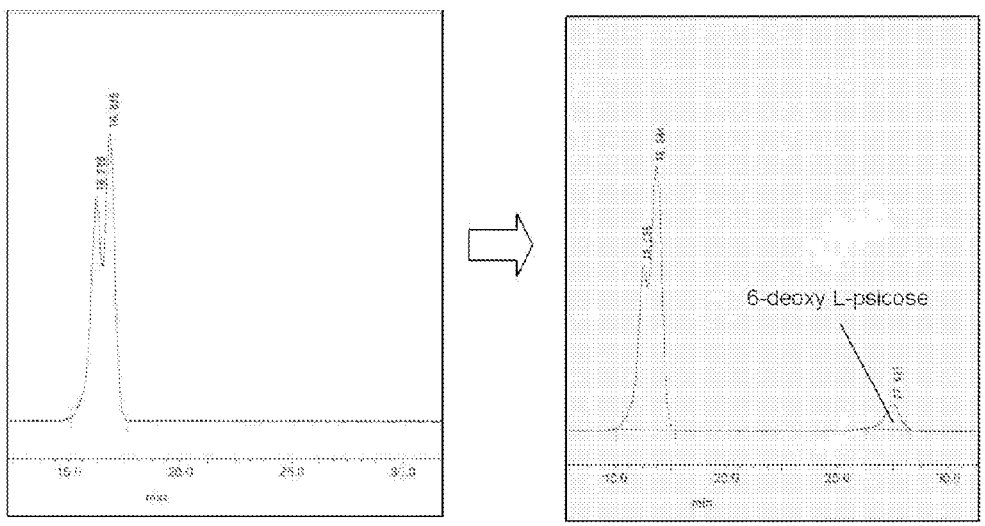

[Fig.13]
(tank A)
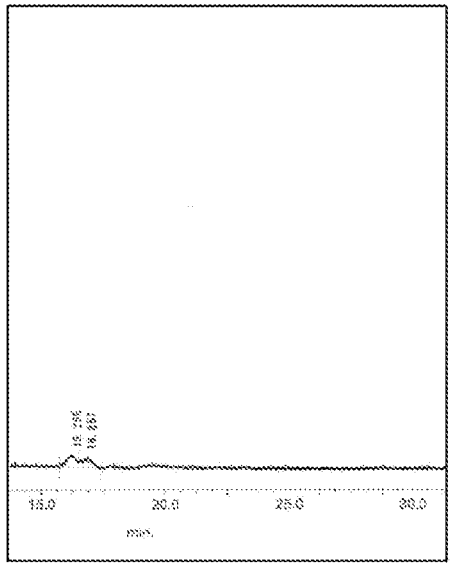
(tank B)
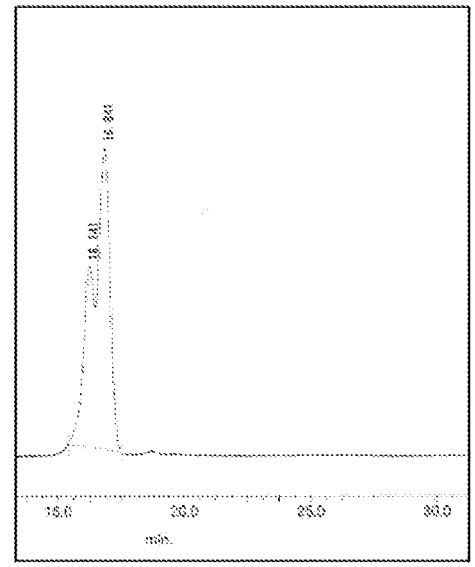
(tank C)
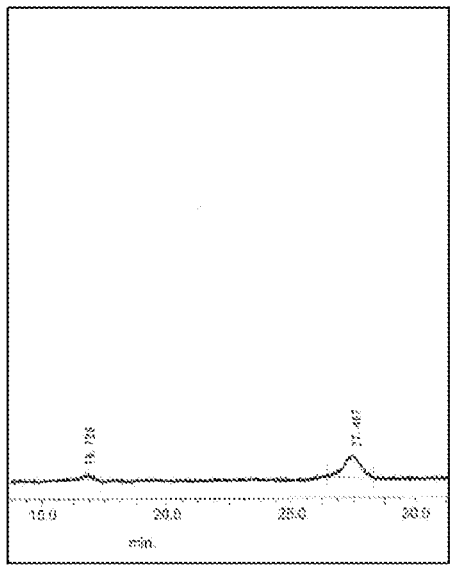
(tank D)
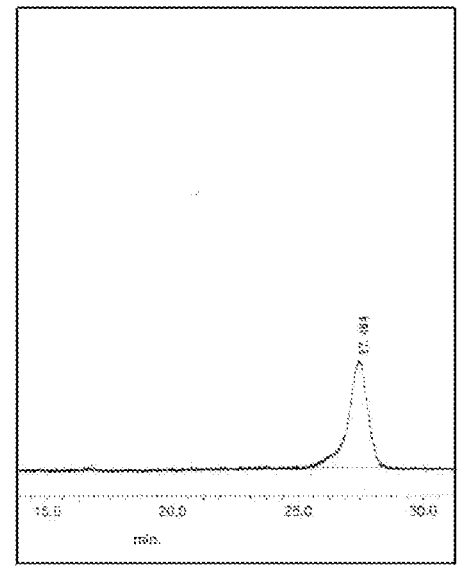

[Fig.14]
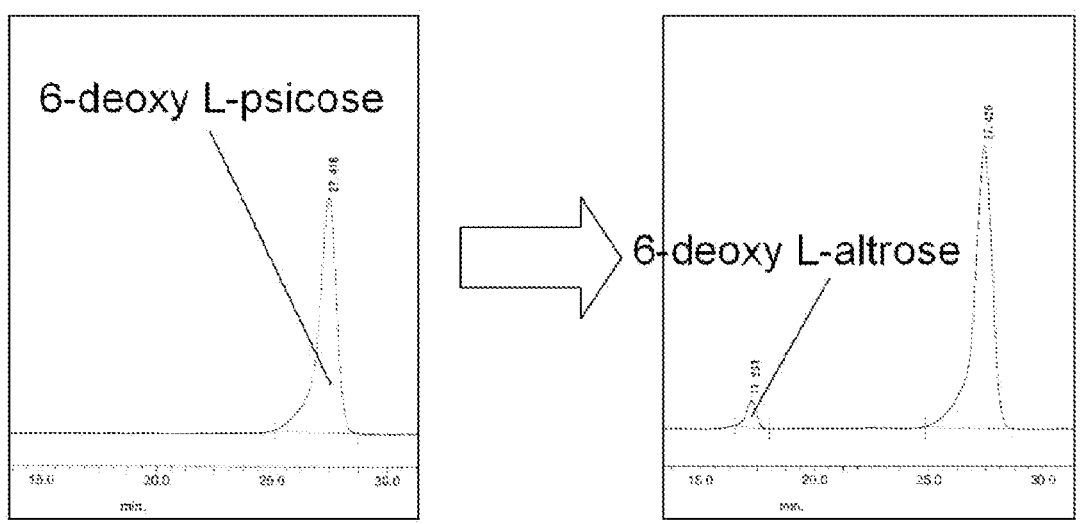

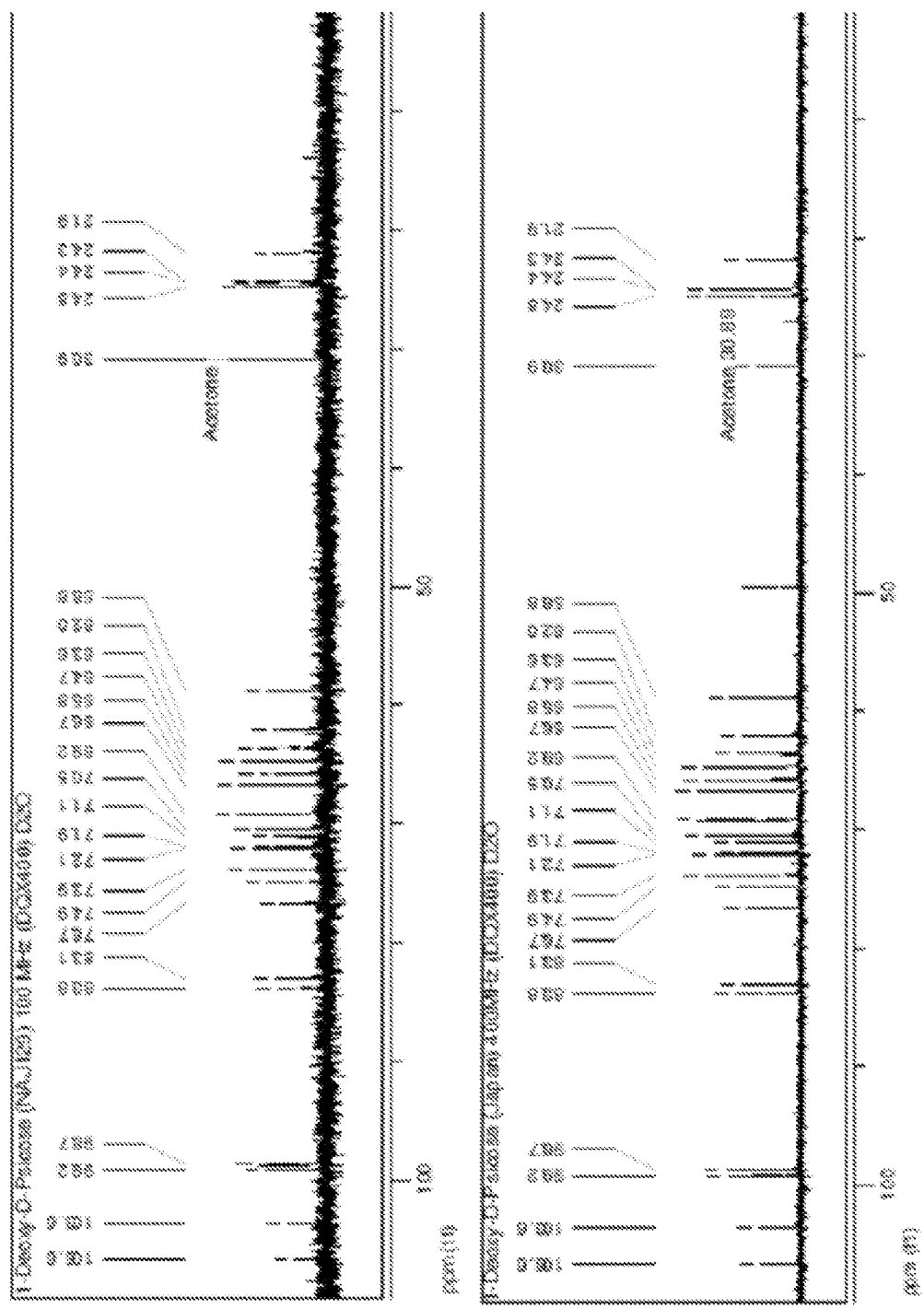
[Fig.15]

[Fig.16]
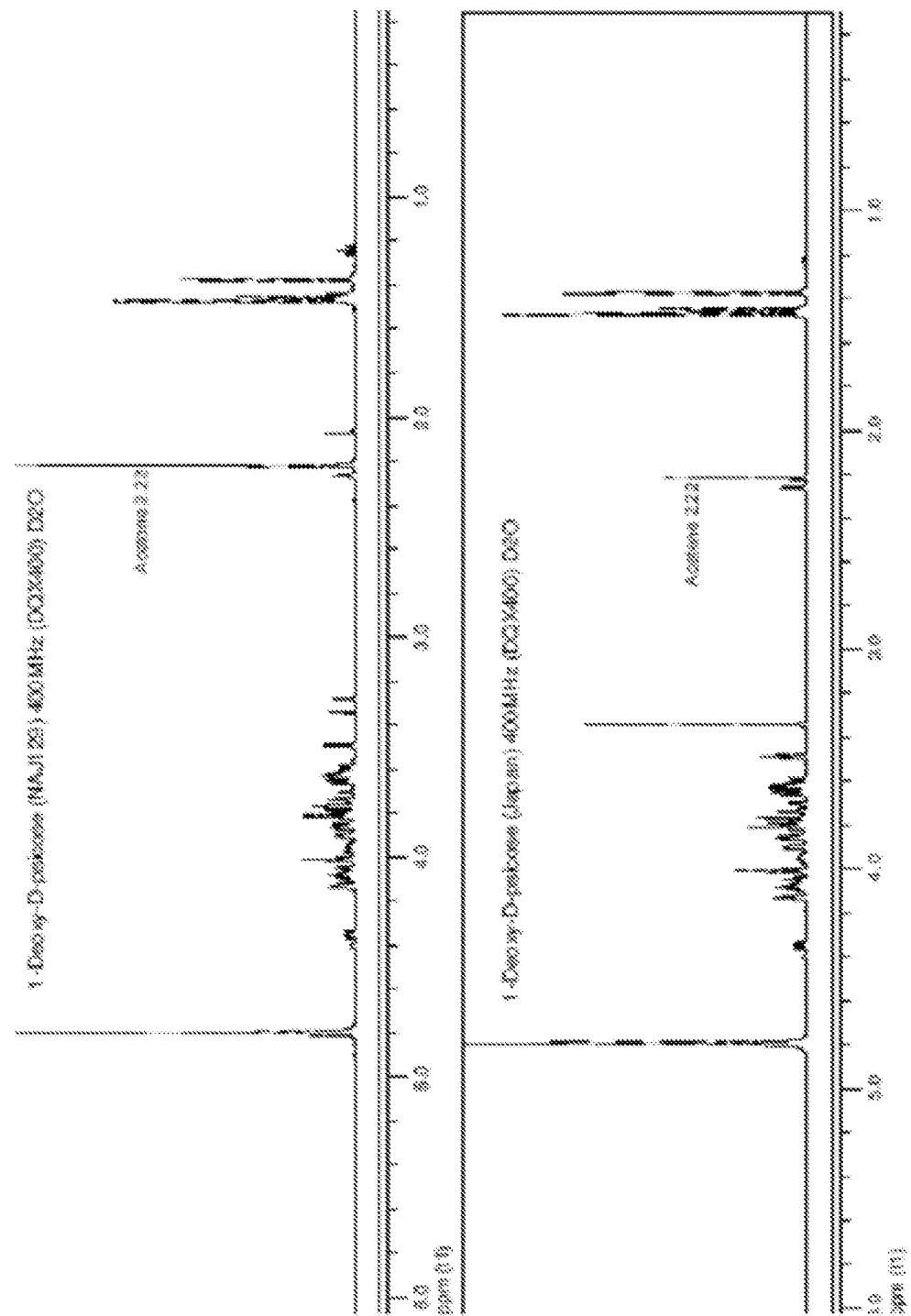

[Fig.17]
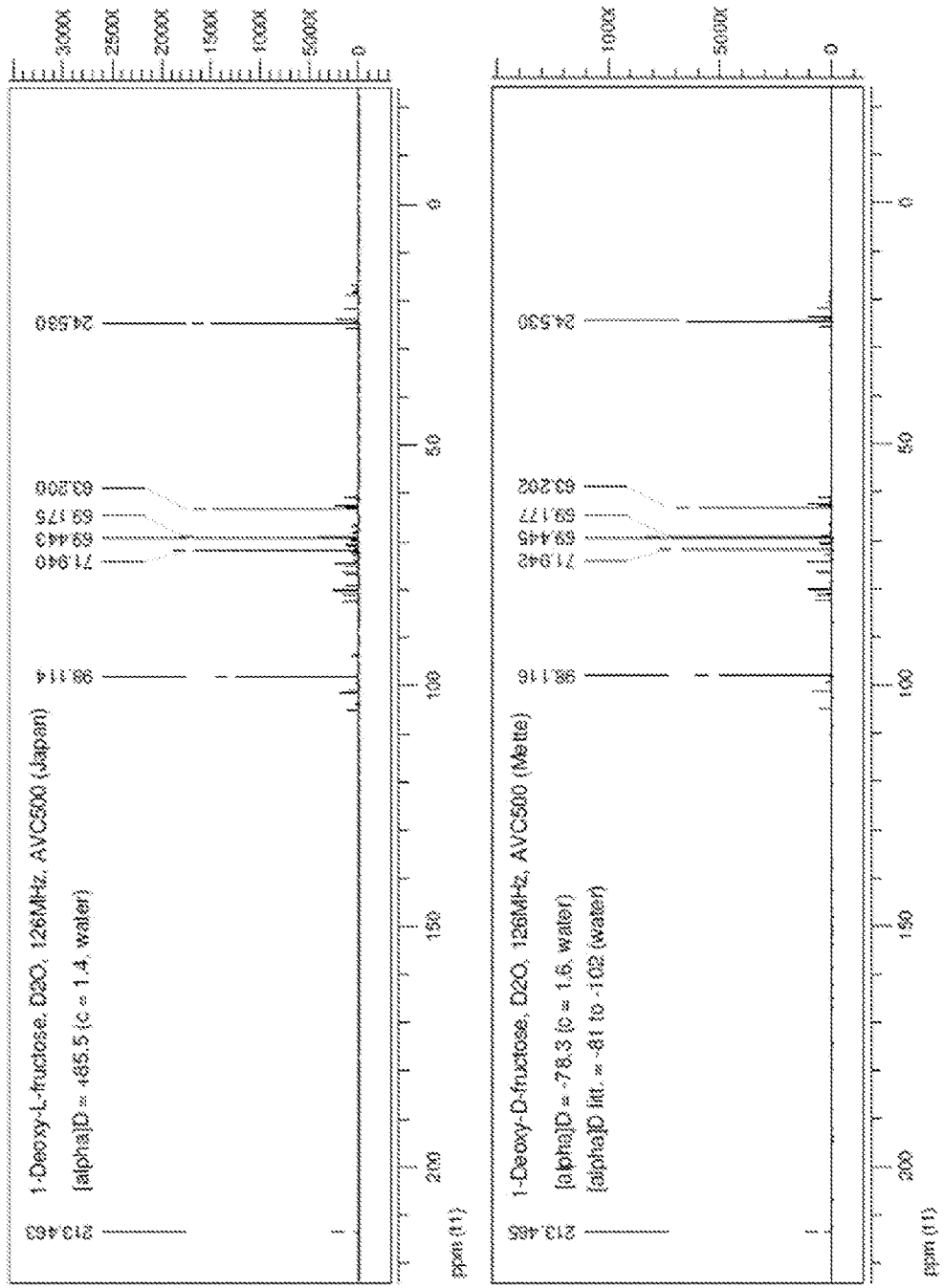

[Fig.18]
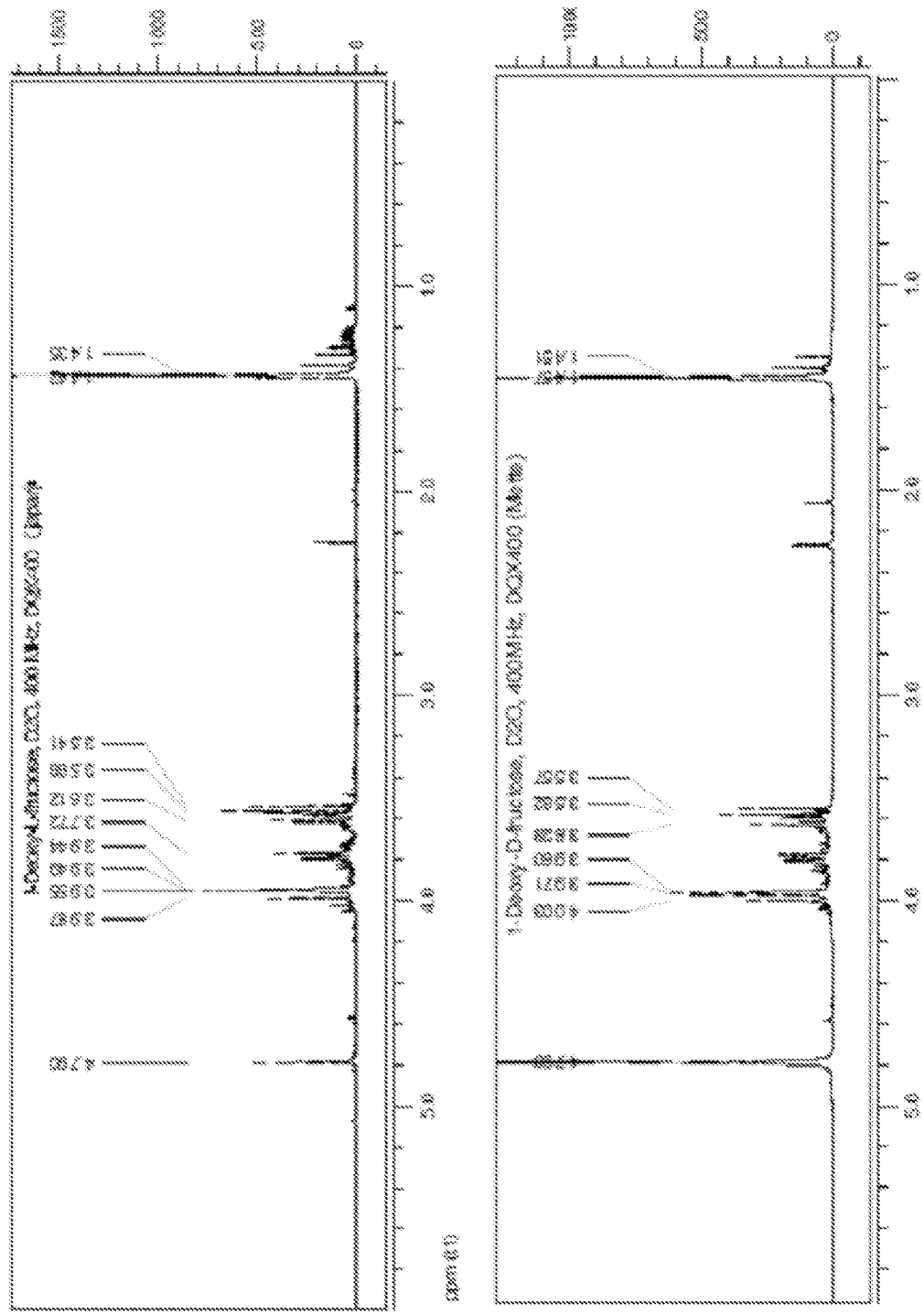

[Fig.19]
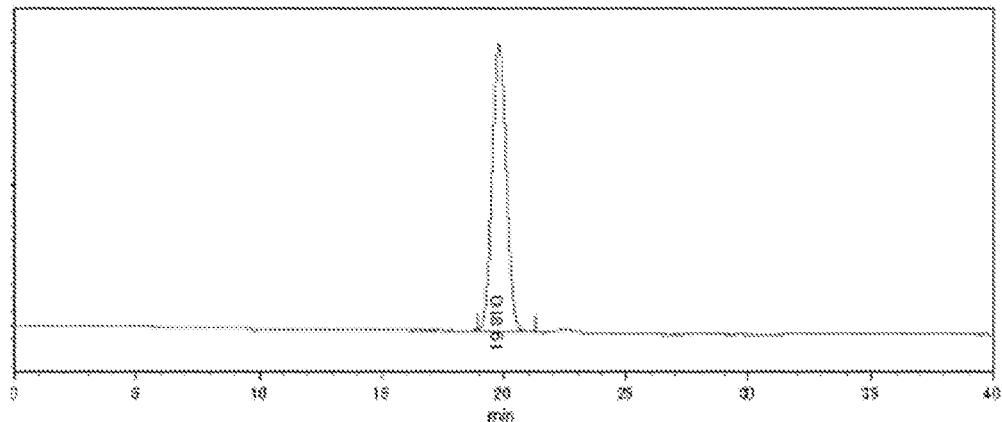
[Fig.20]
¹³C-NMR of product
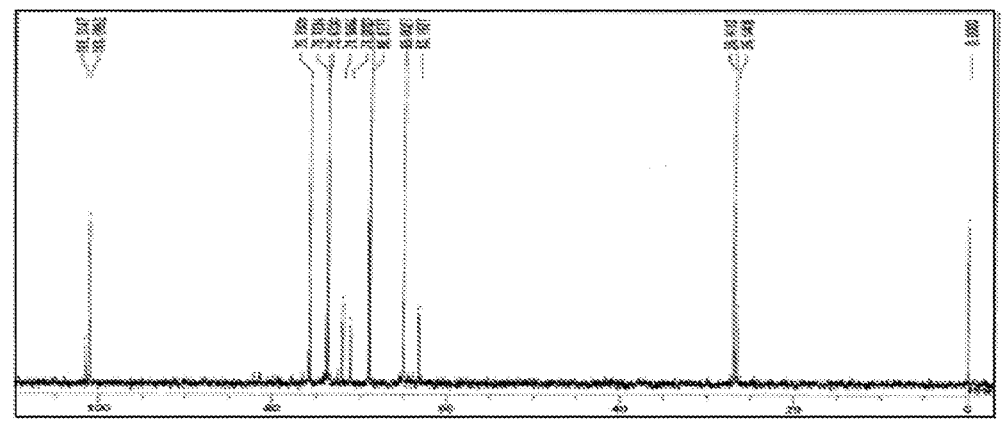
[Fig.21]
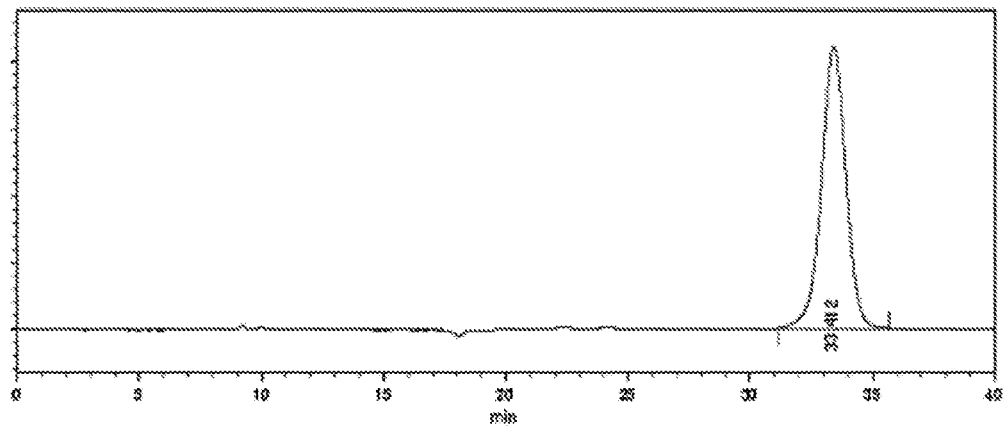

[Fig.22]
¹³C-NMR of product
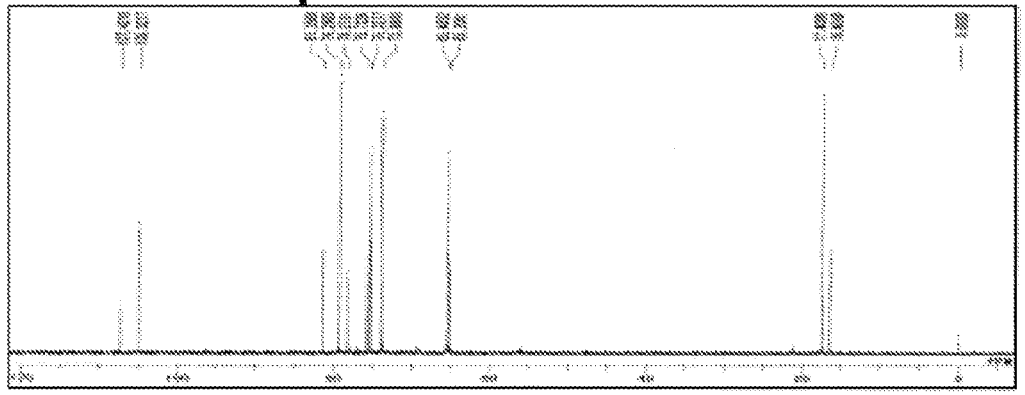
¹³C-NMR of 6-deoxy L-Tagatose
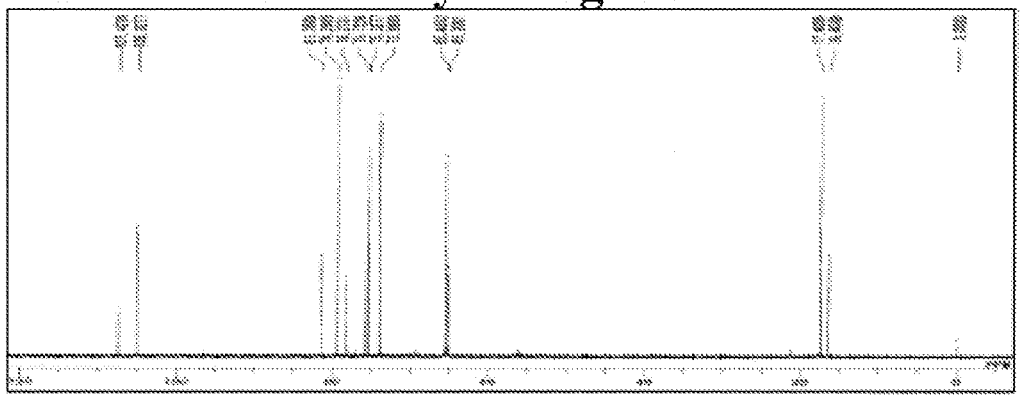
[Fig.23]
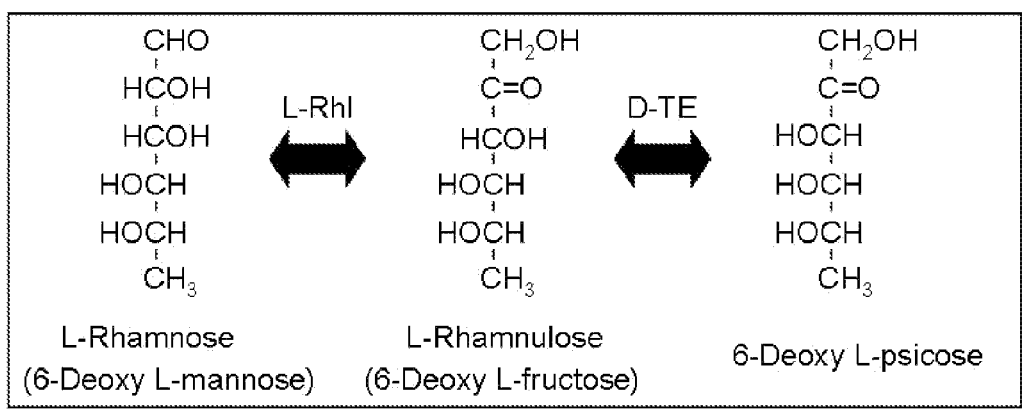

[Fig.24]
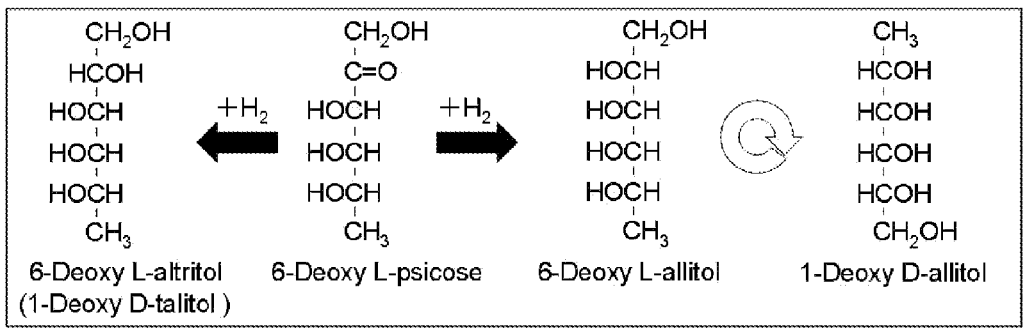
[Fig.25]
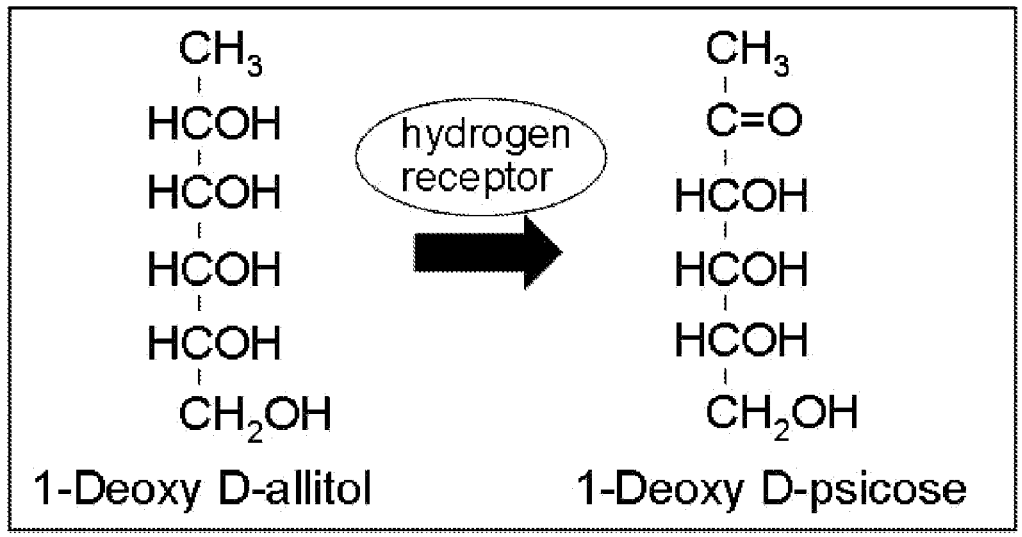
[Fig.26]
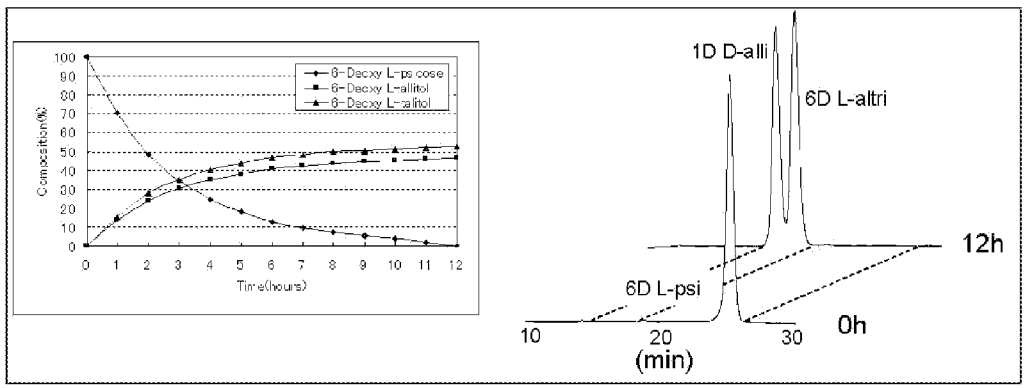

[Fig.27]
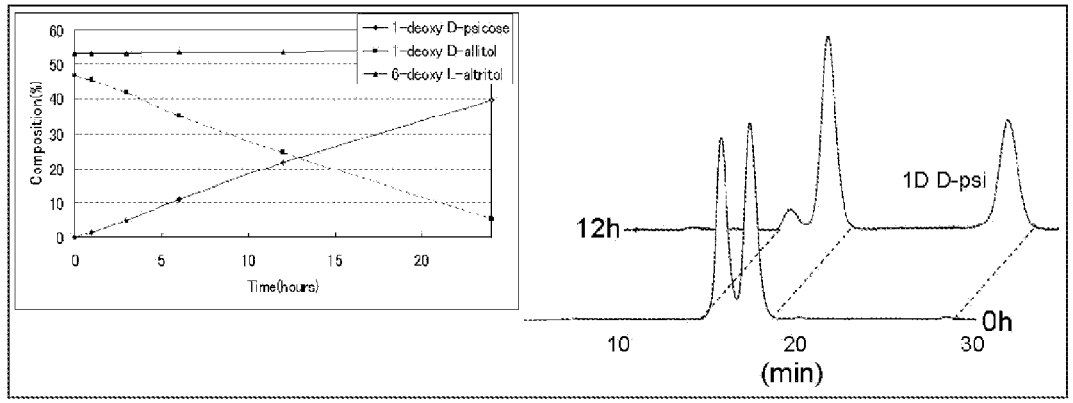
[Fig.28]
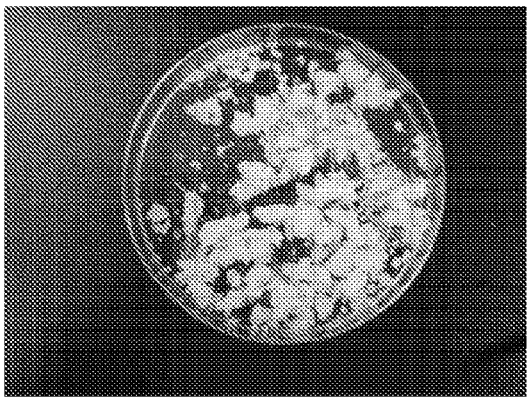
Crystal of 1-deoxy D-psicose
[Fig.29]
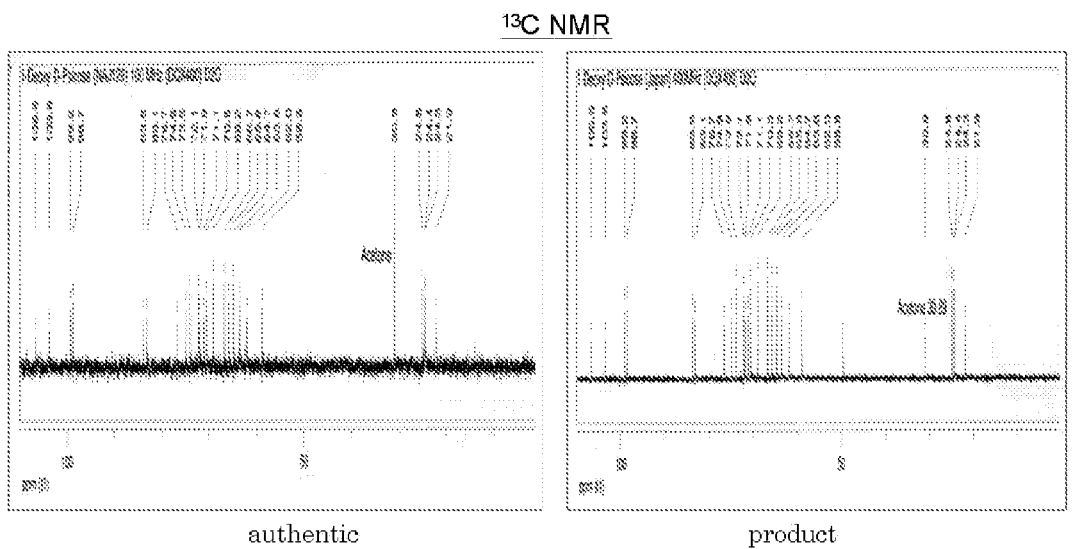
authentic                    product

[Fig.30]
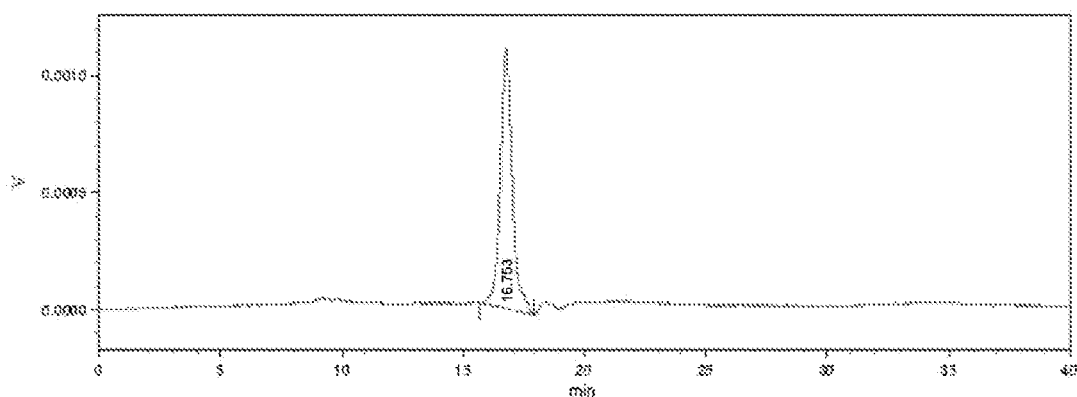

[Fig.31]
*6-deoxy-L-Fructose $^{13}C$ NMR spectra (STANDARD)*
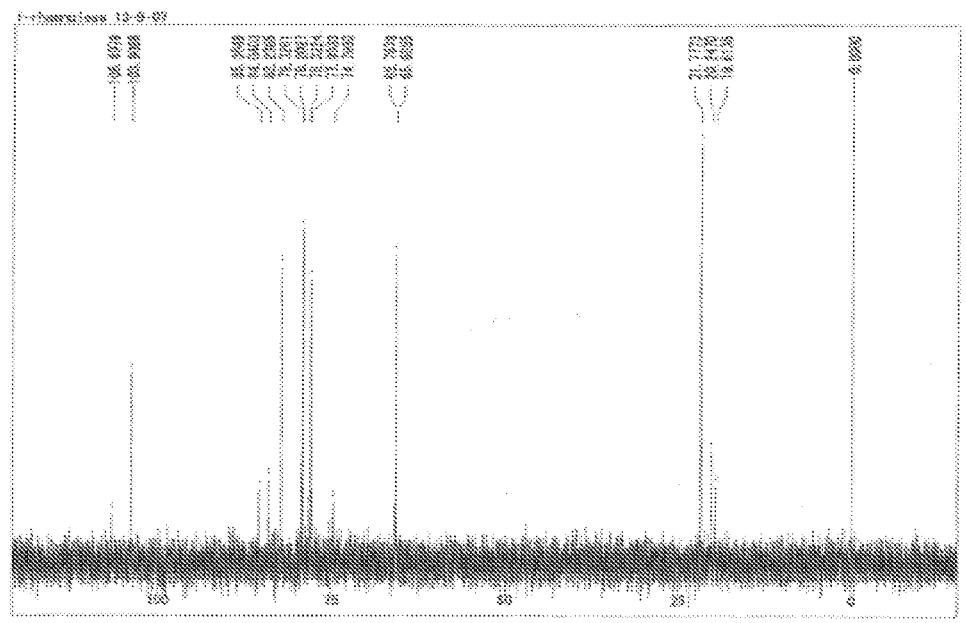
*6-deoxy-L-fructose $^{13}C$ spectra (PRODUCT)*
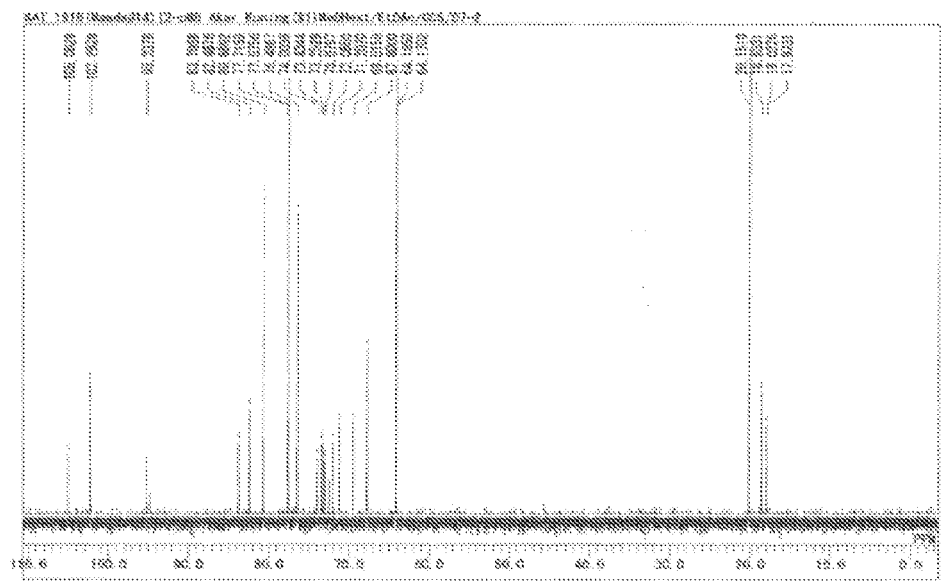

[Fig.32]
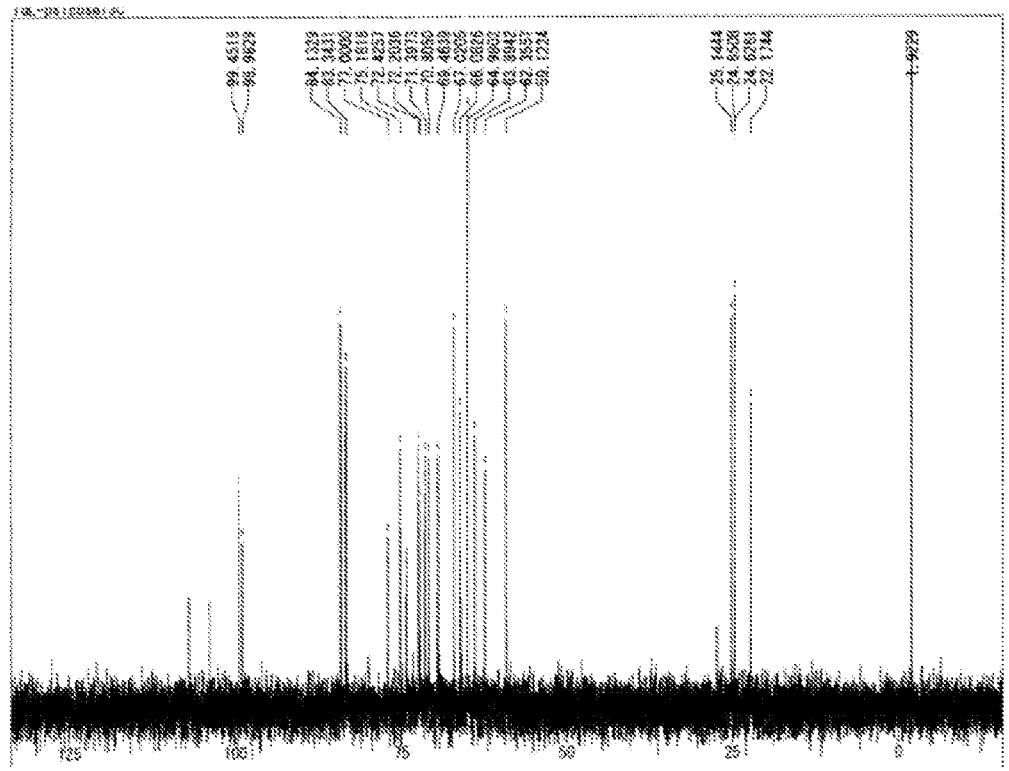
[Fig.33]
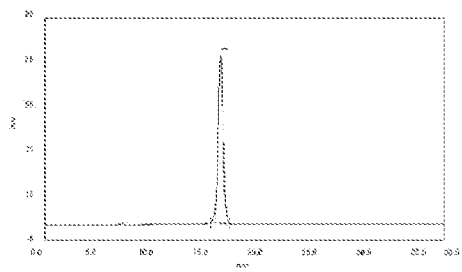
L-rhamnose (S)
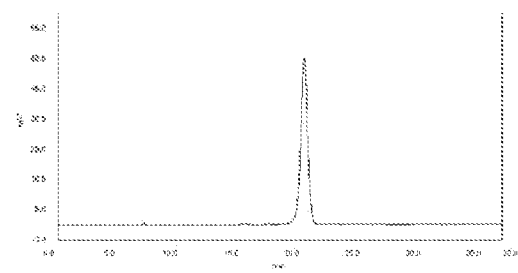
6-deoxy-L-mannitol (P)

[Fig.34]
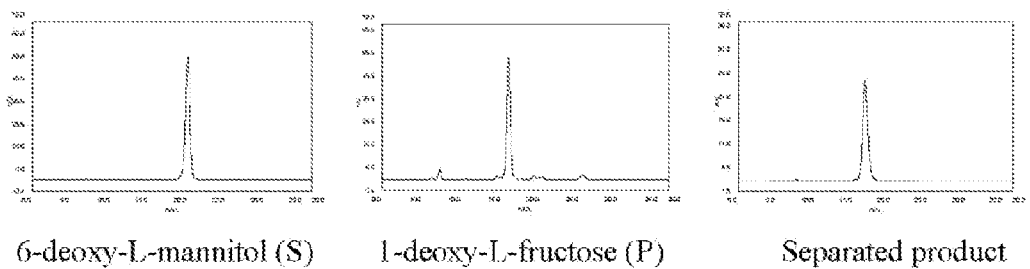
6-deoxy-L-mannitol (S)    1-deoxy-L-fructose (P)    Separated product
[Fig.35]
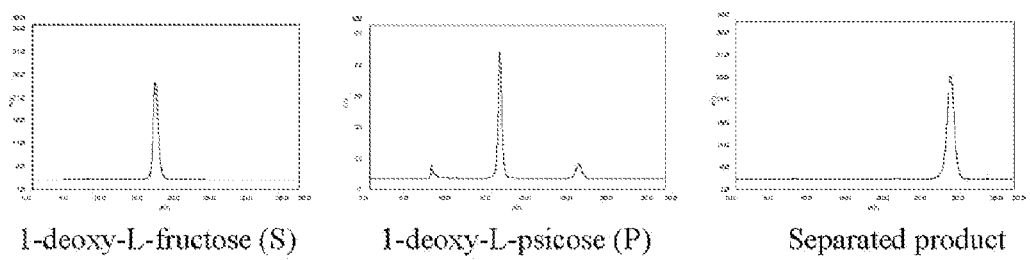
1-deoxy-L-fructose (S)    1-deoxy-L-psicose (P)    Separated product
[Fig.36]
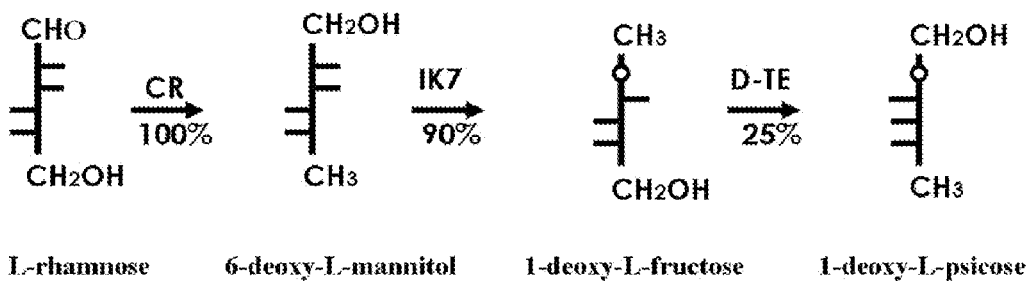
L-rhamnose    6-deoxy-L-mannitol    1-deoxy-L-fructose    1-deoxy-L-psicose

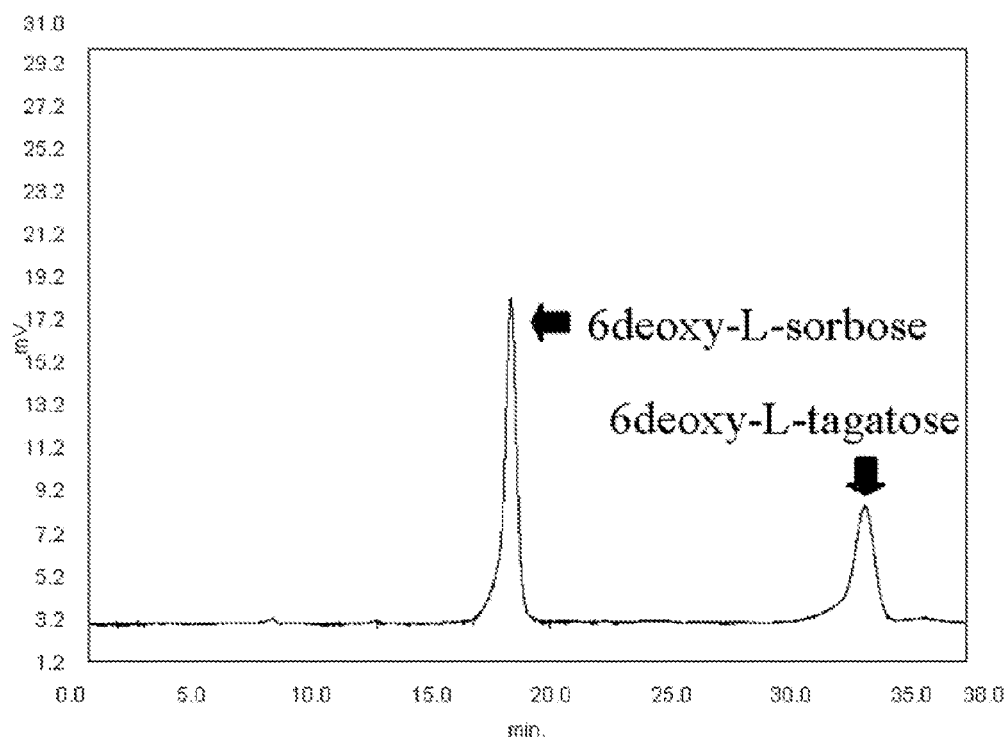
[Fig.37]
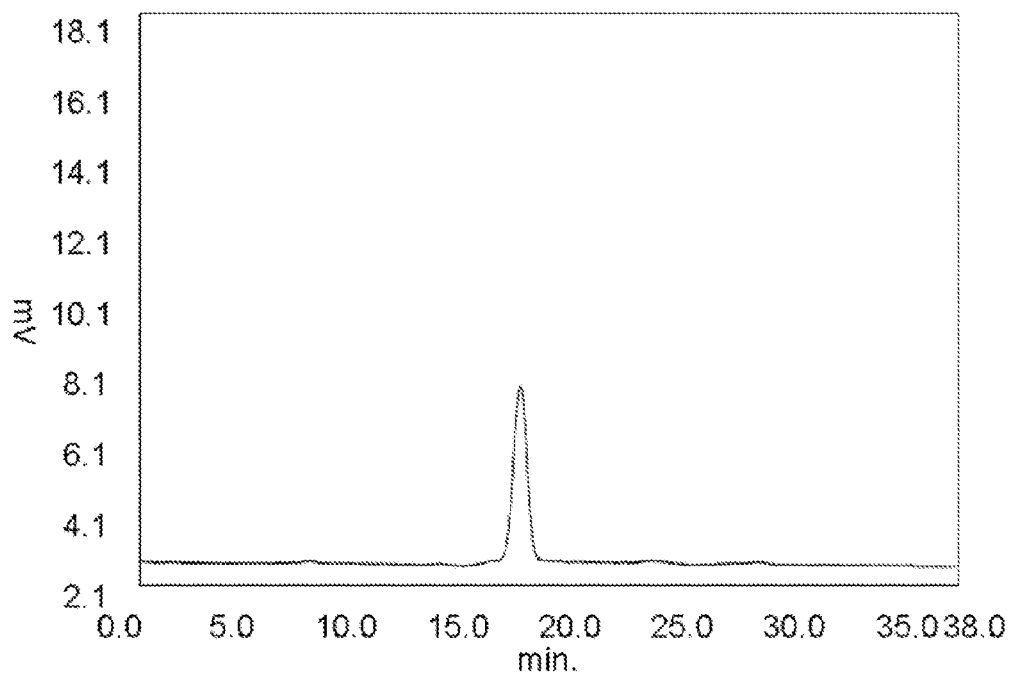
[Fig.38]

[Fig.39]
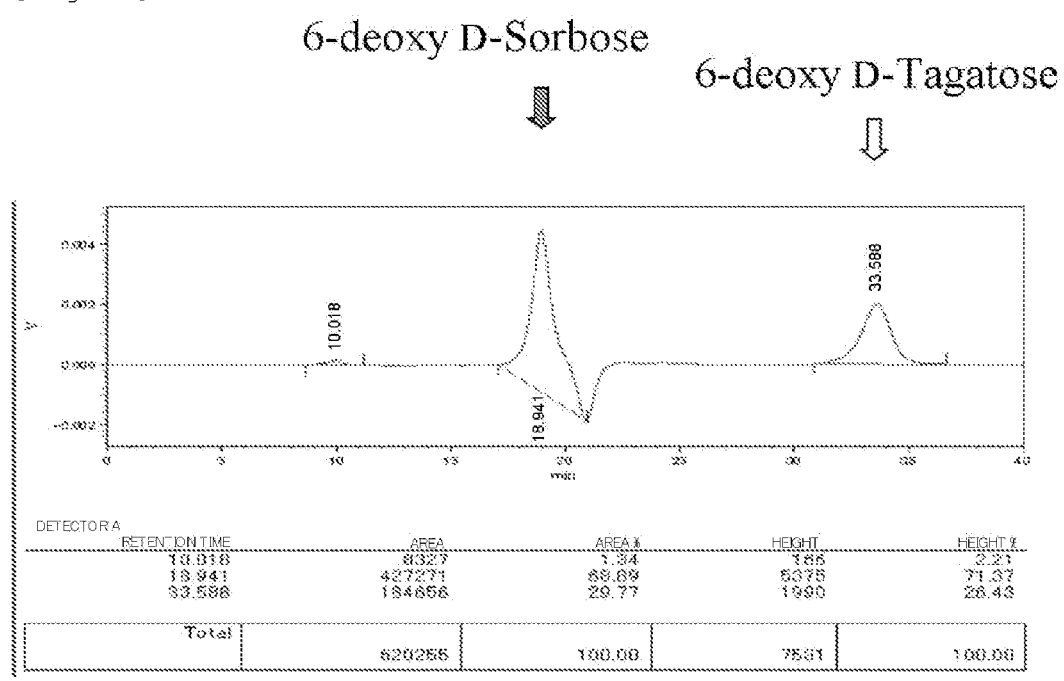

[Fig.40]
(a) 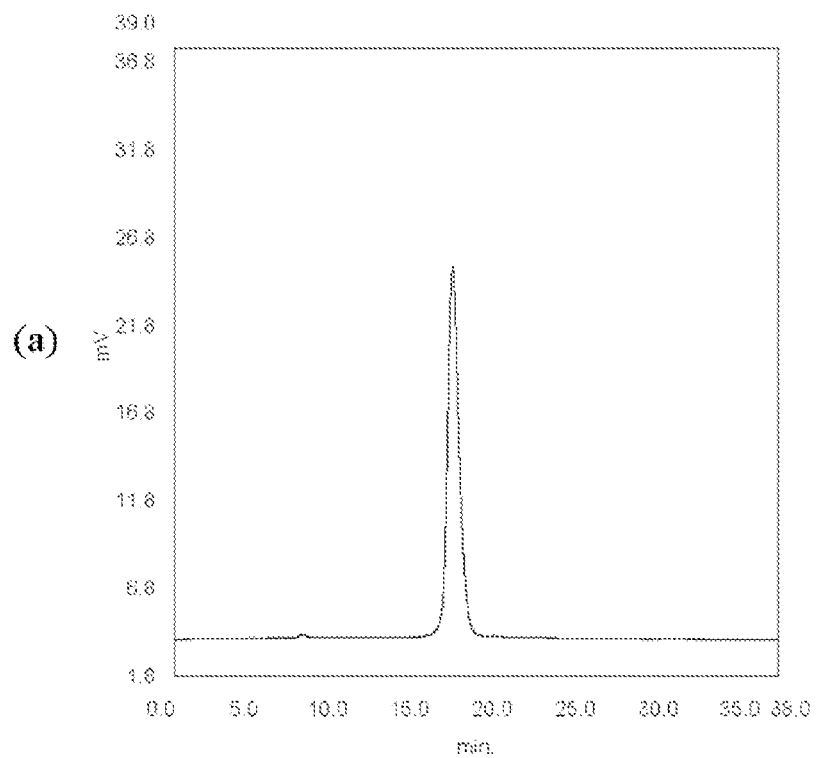
(b) 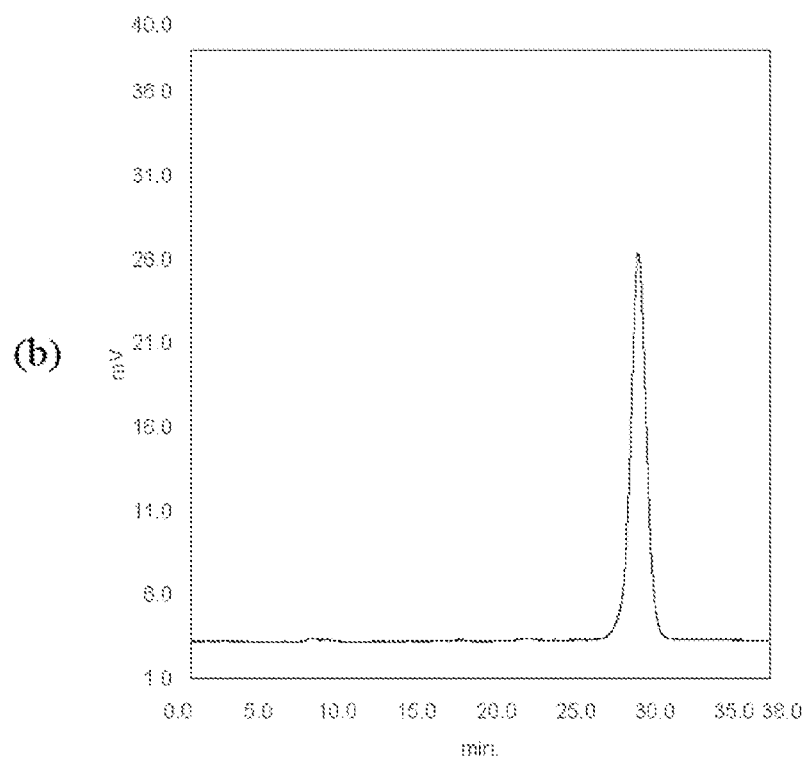

[Fig.41]
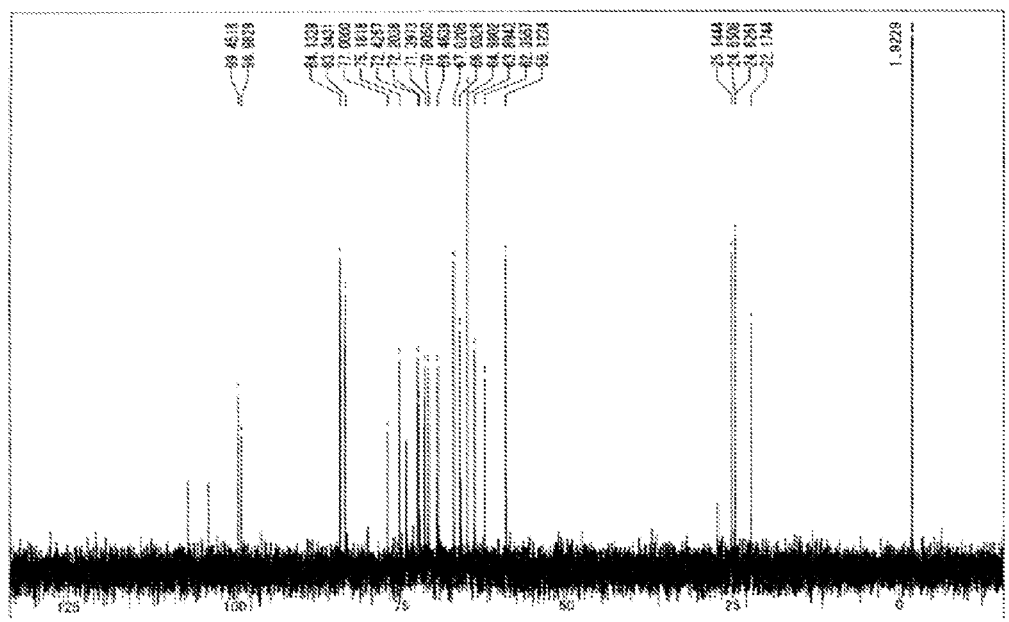

[Fig.42]
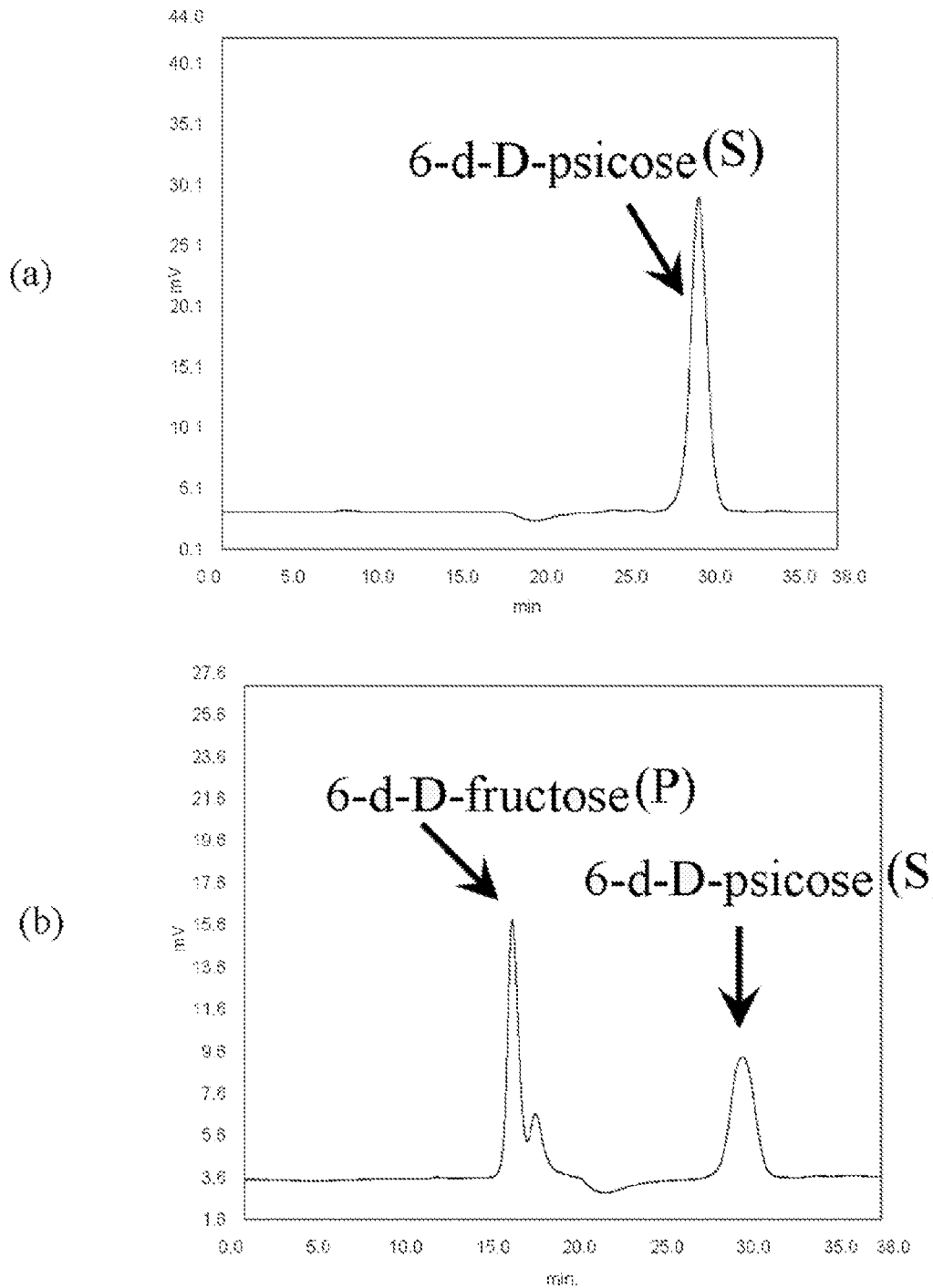

[Fig.43]
(a) 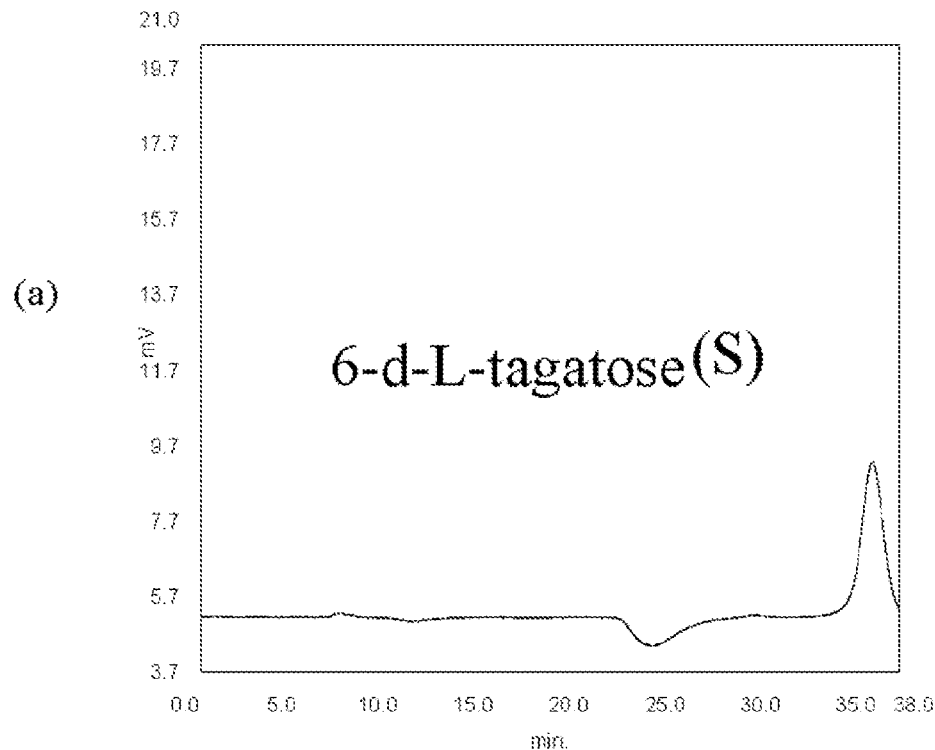
(b) 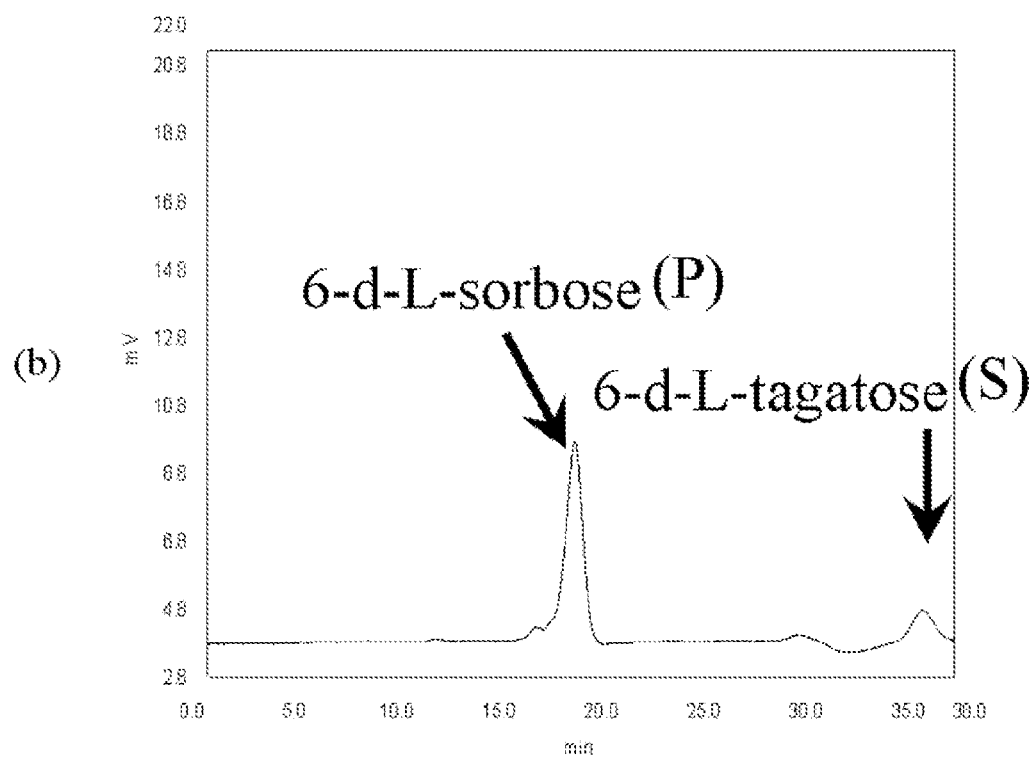

[Fig.44]
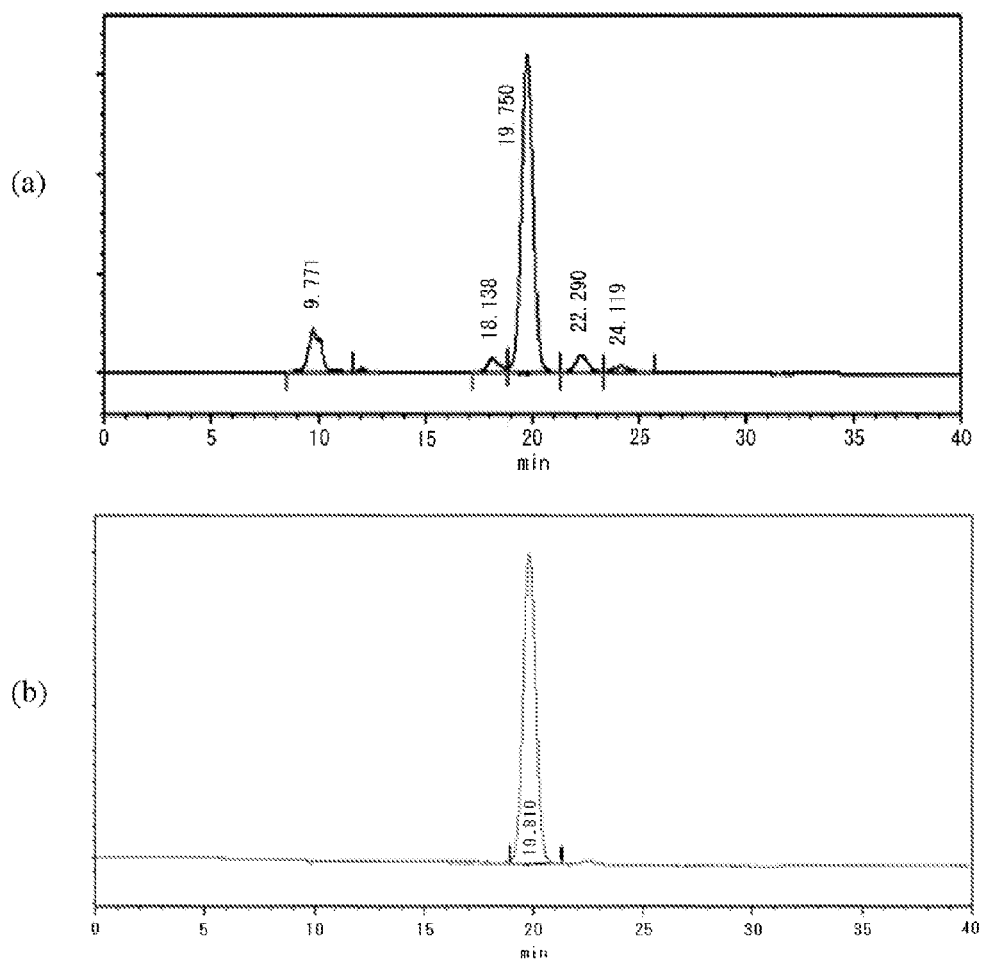

[Fig.45]
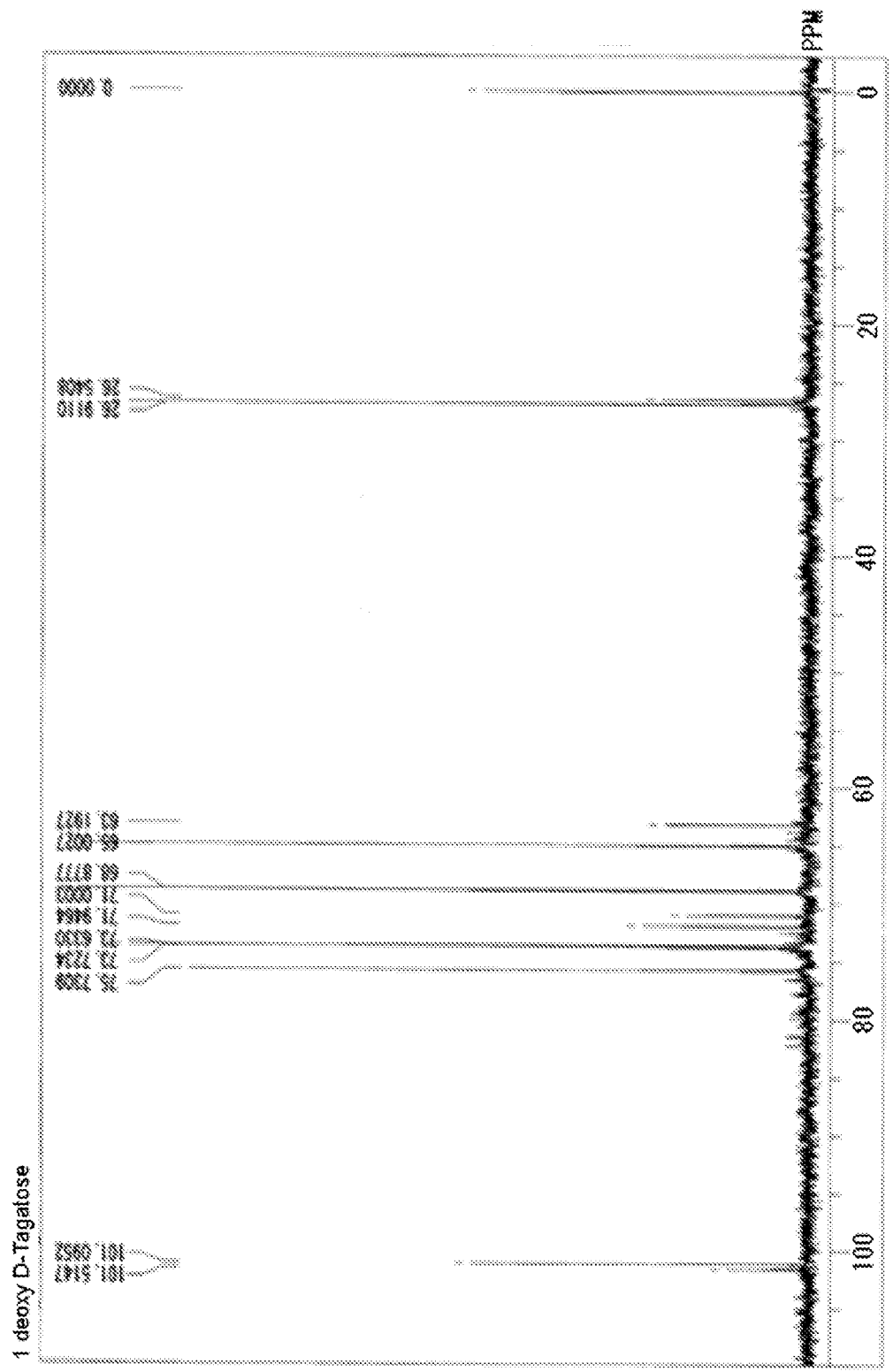

[Fig.46]
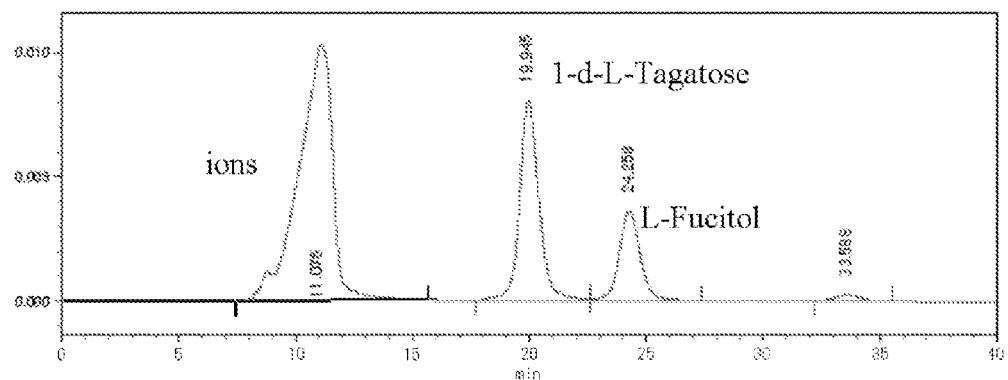
[Fig.47]
(a)
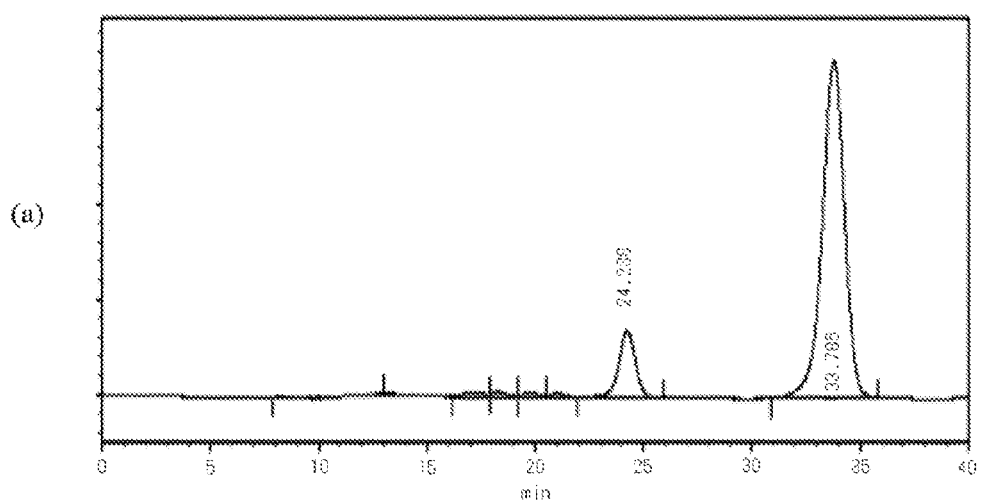
(b)
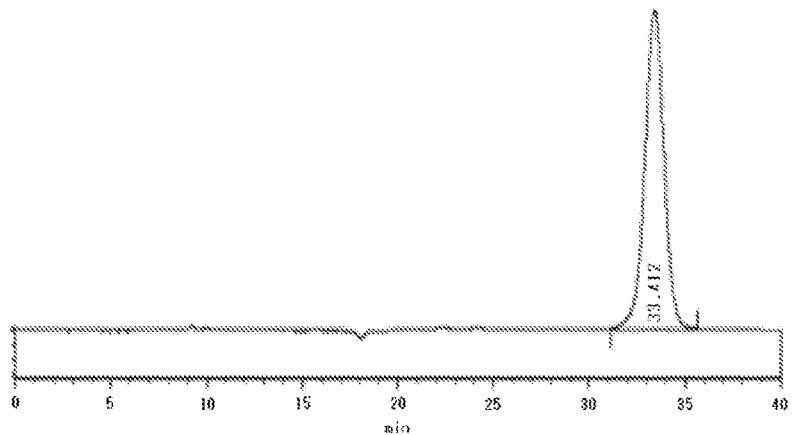

[Fig.48]
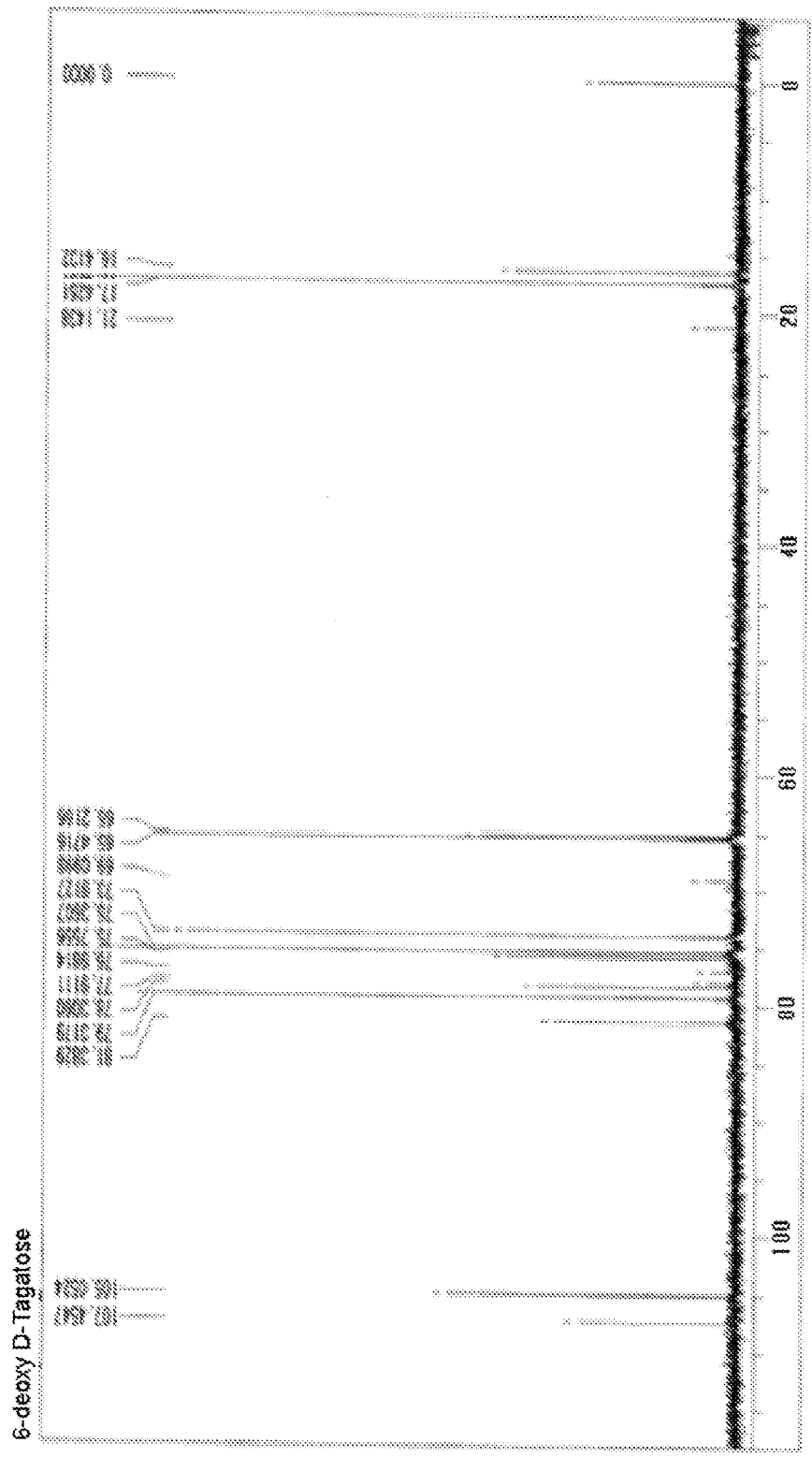

[Fig.49]
(a) 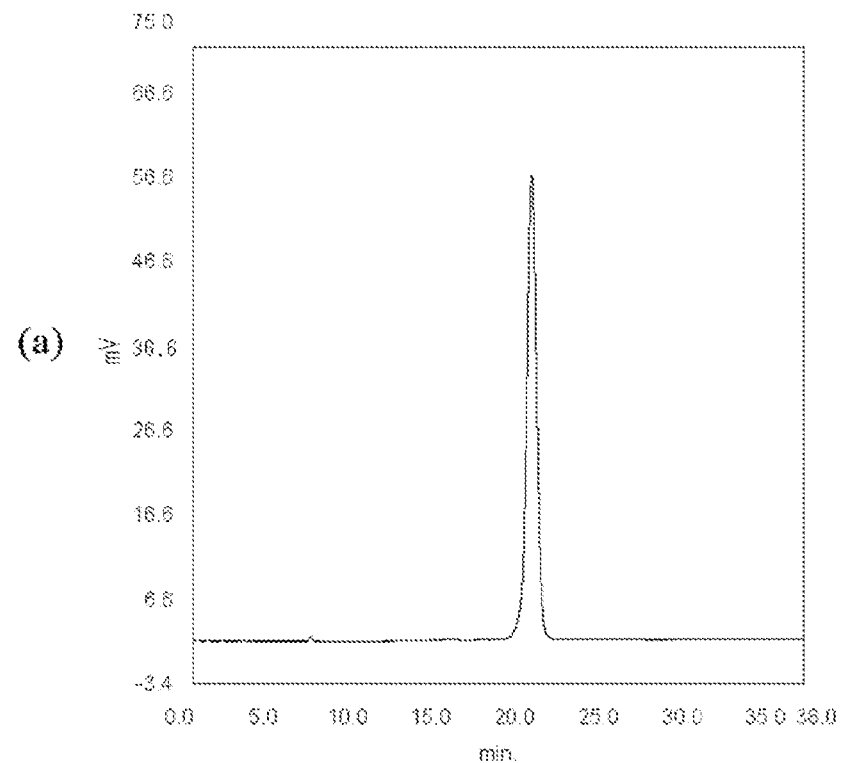
(b) 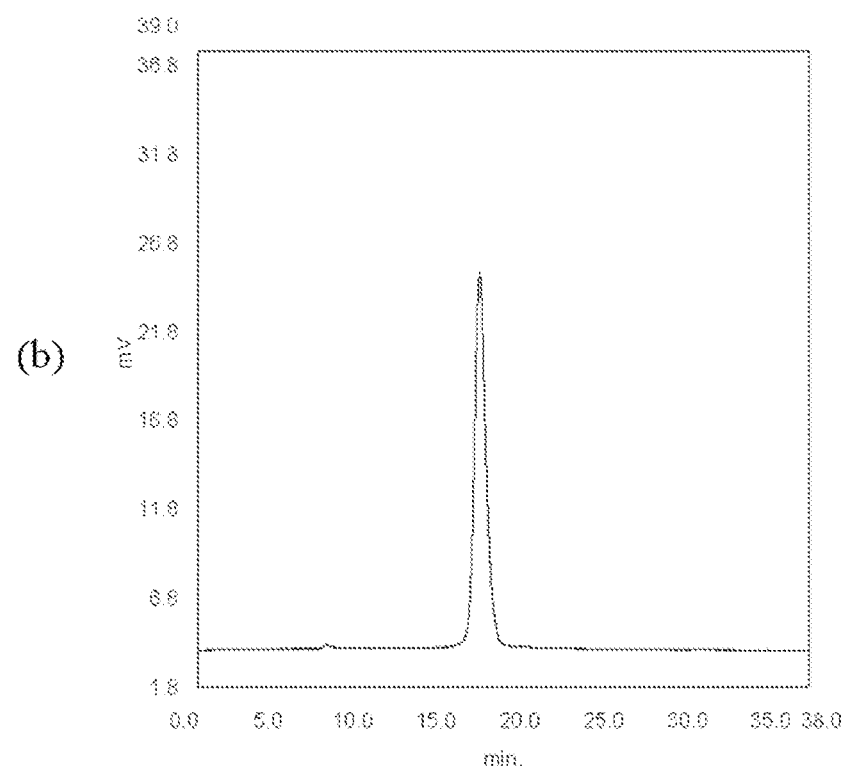

[Fig.50]
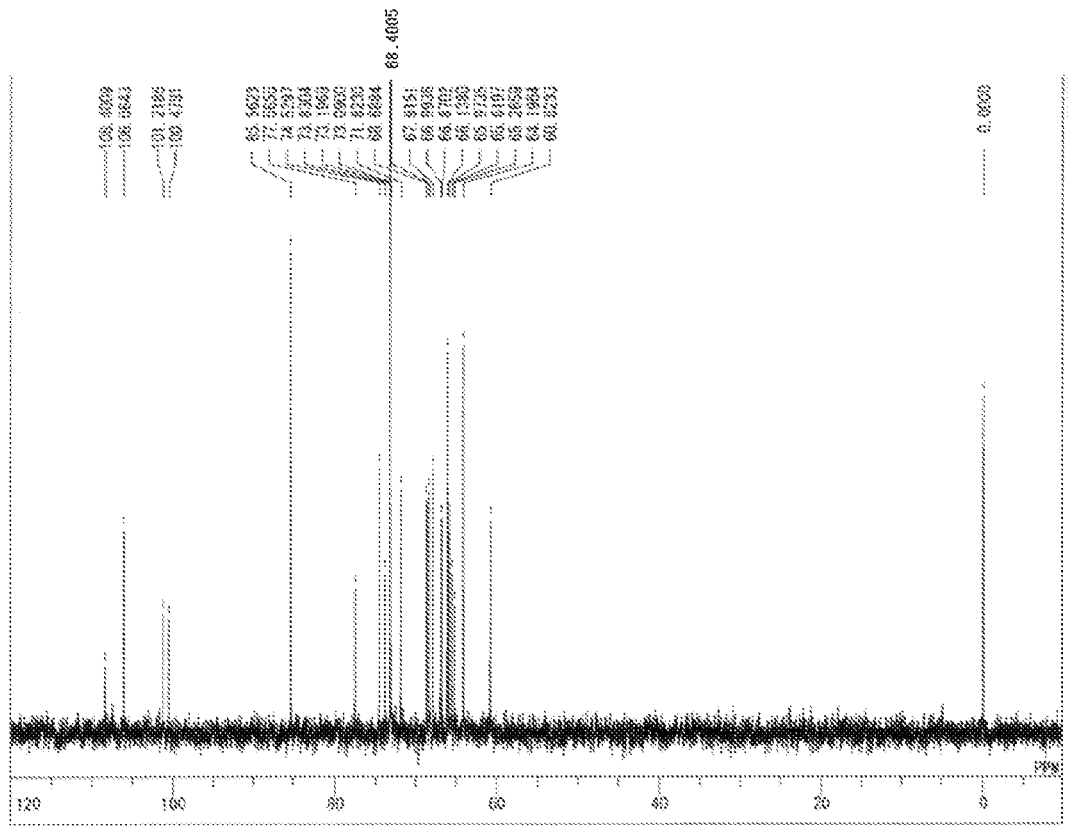

[Fig.51]
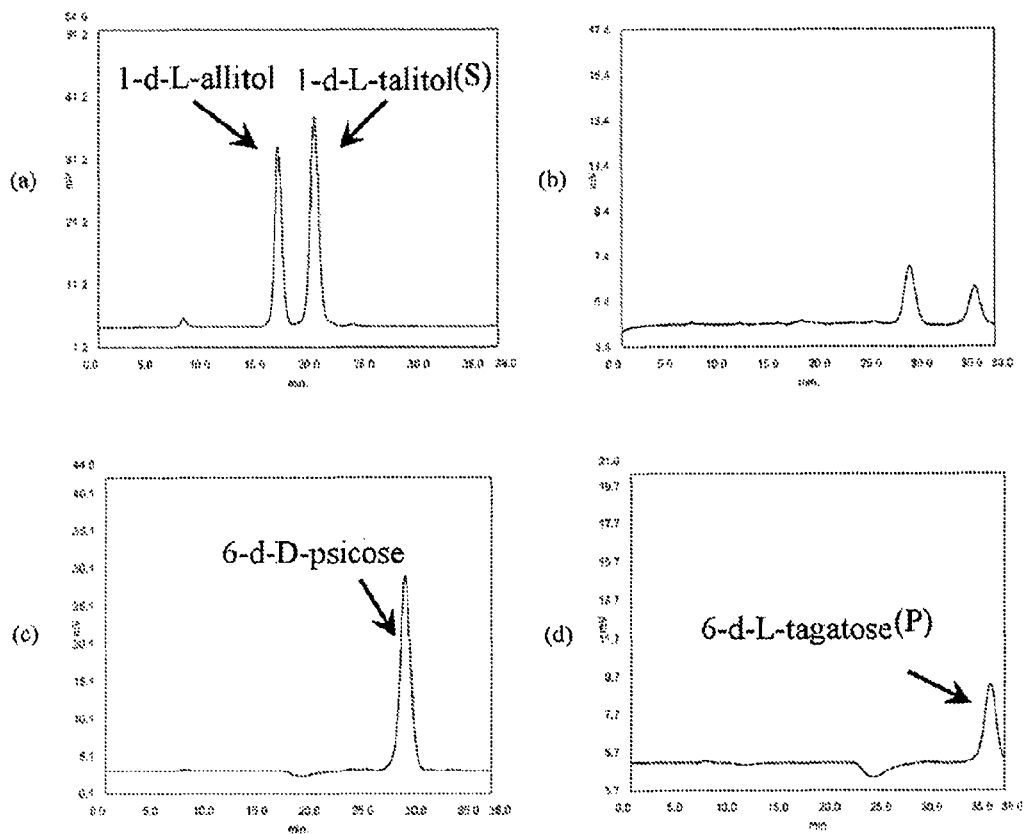

[Fig.52]
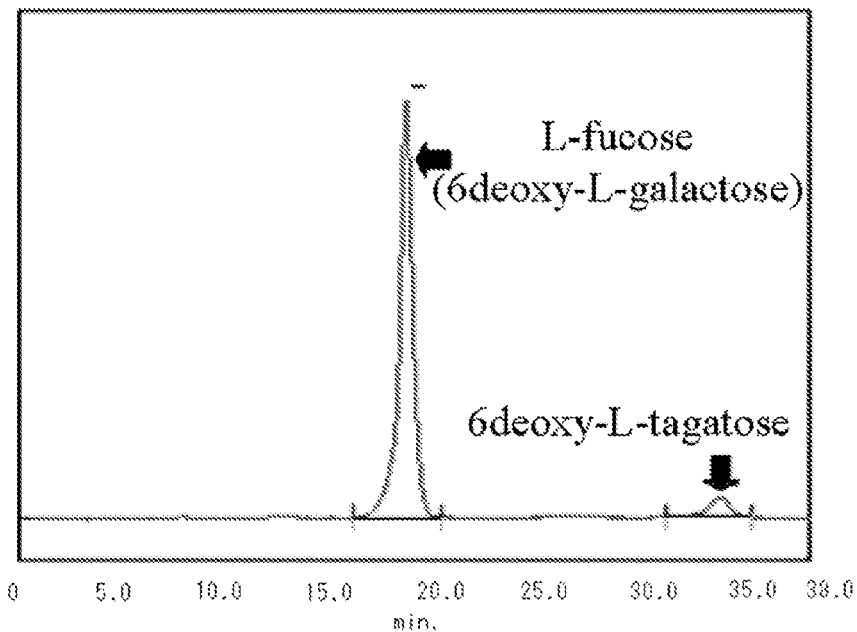
(a)
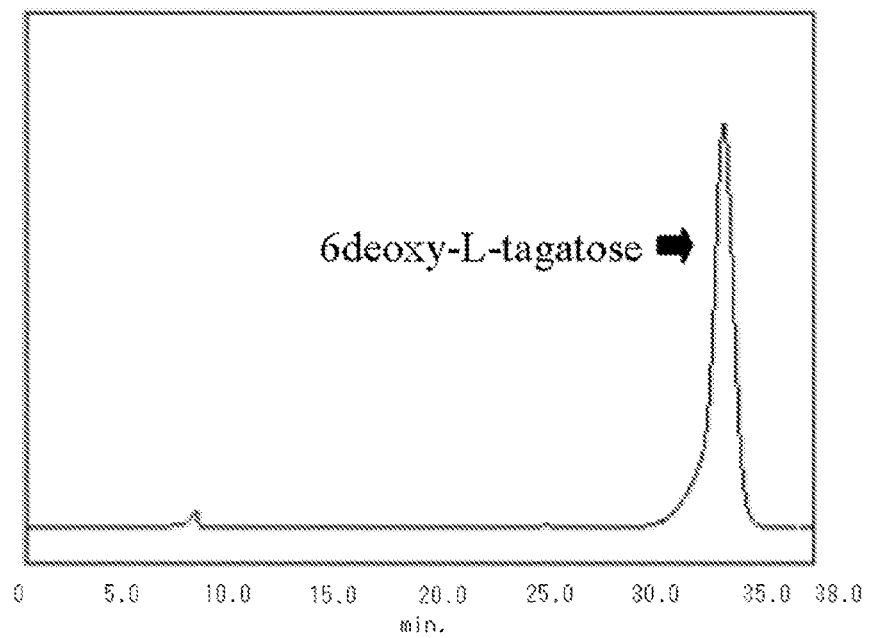
(b)

[Fig.53]
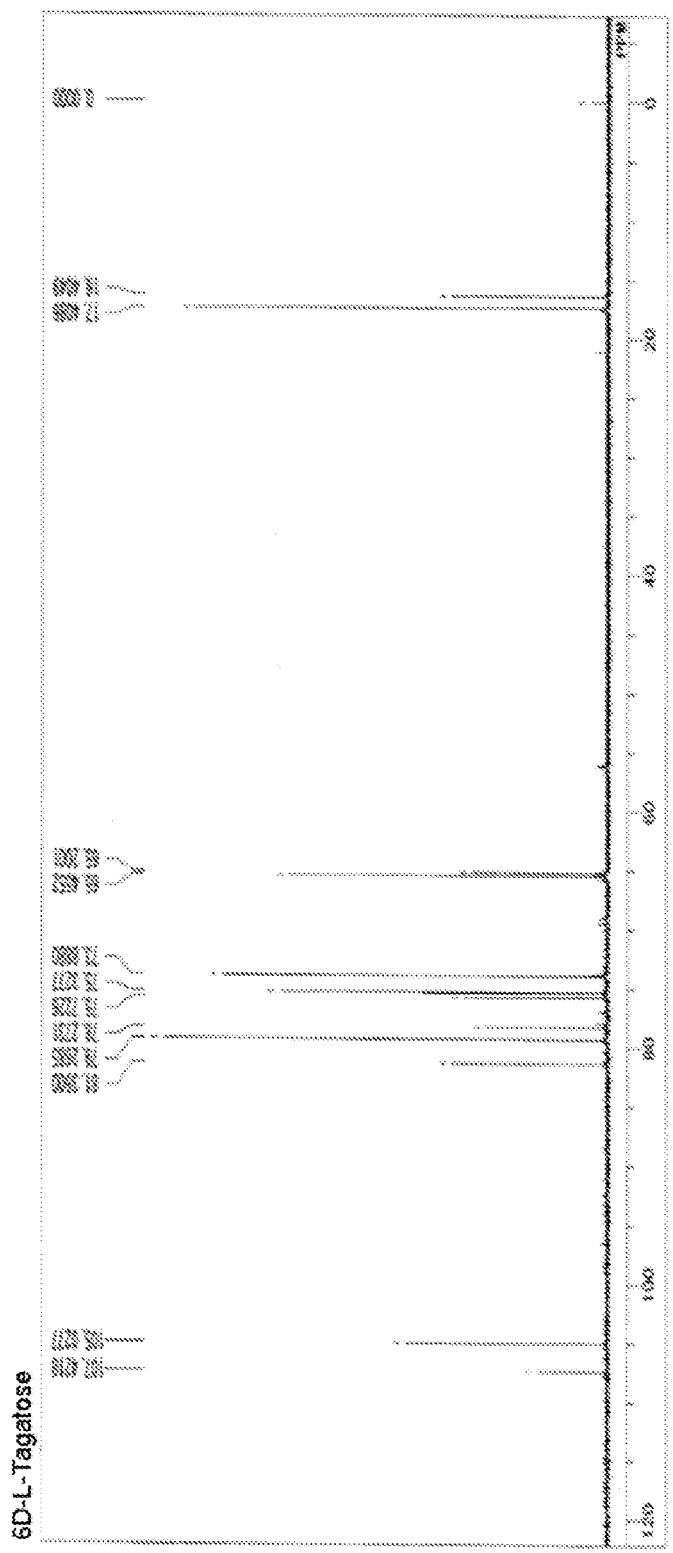

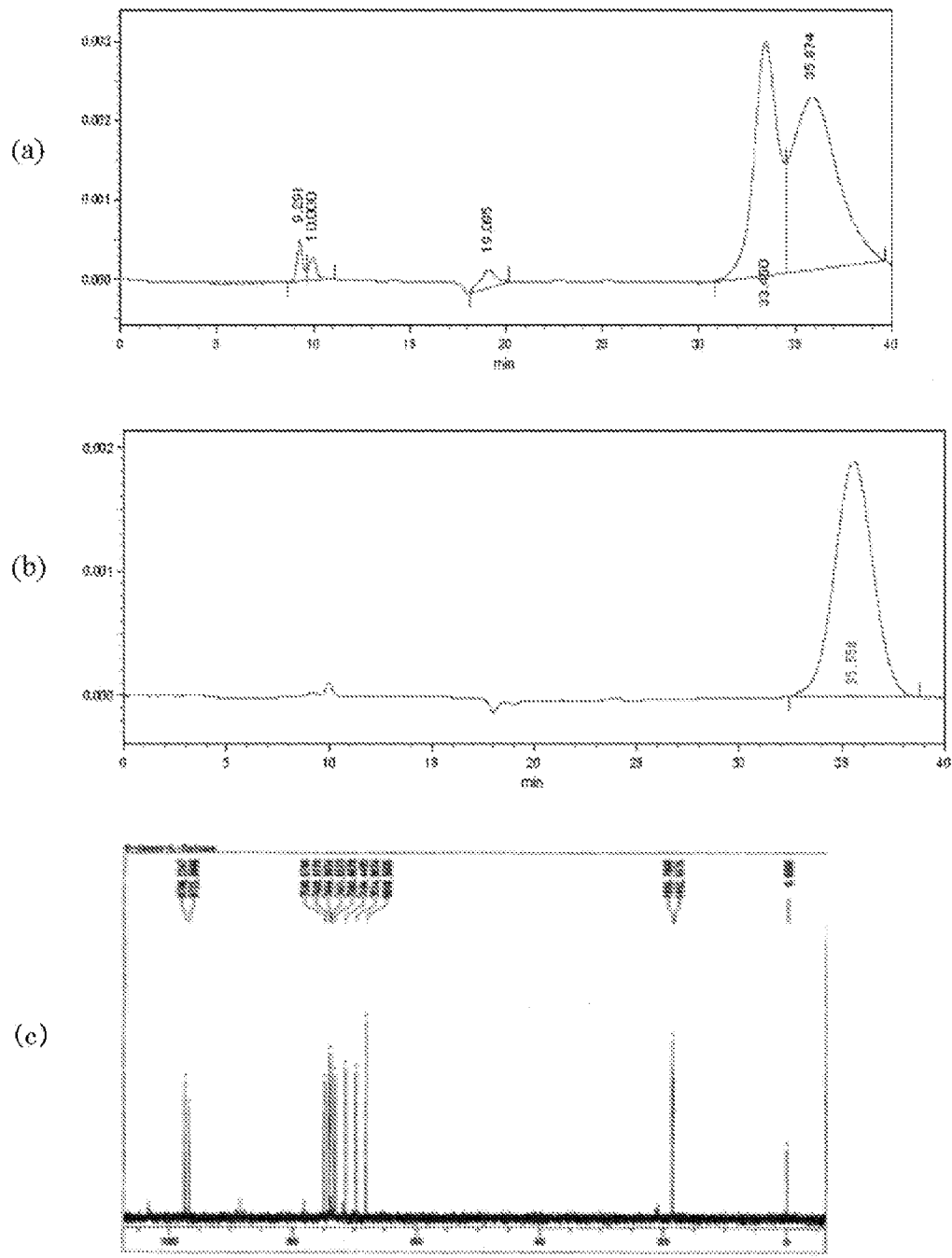
[Fig.54]

[Fig.55]
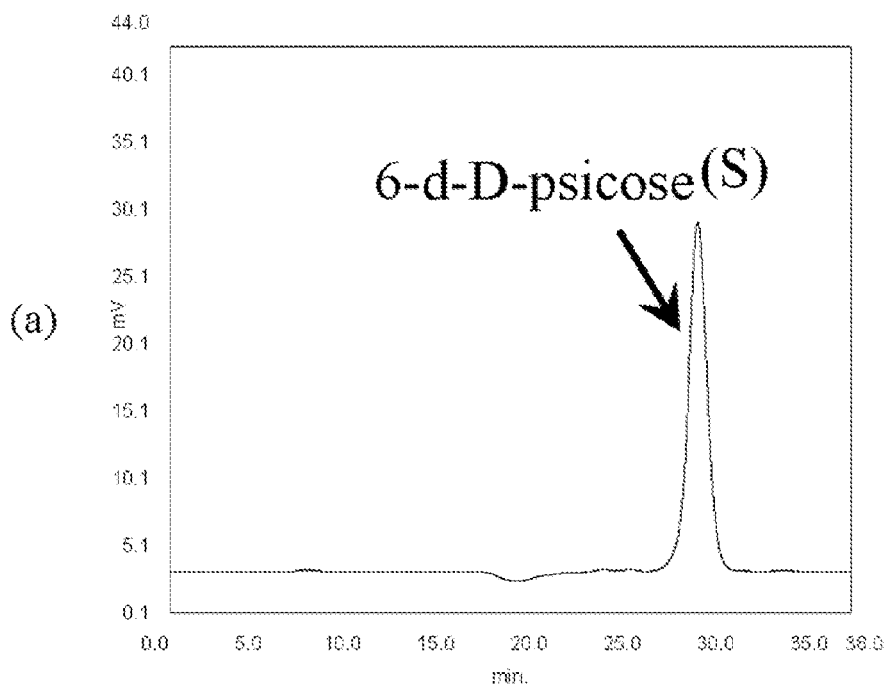
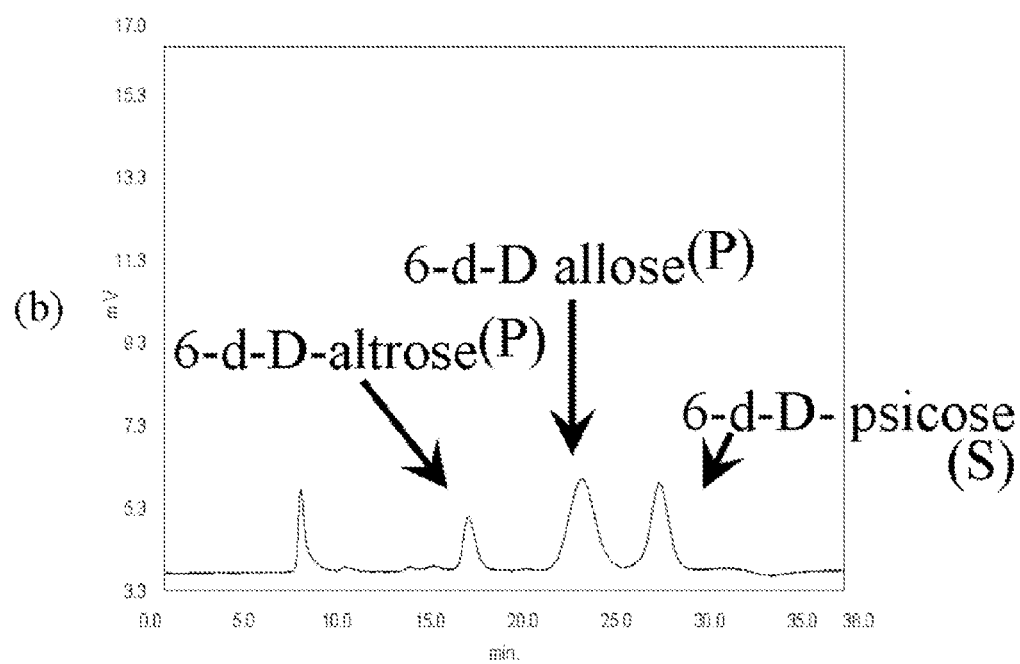

[Fig.56]
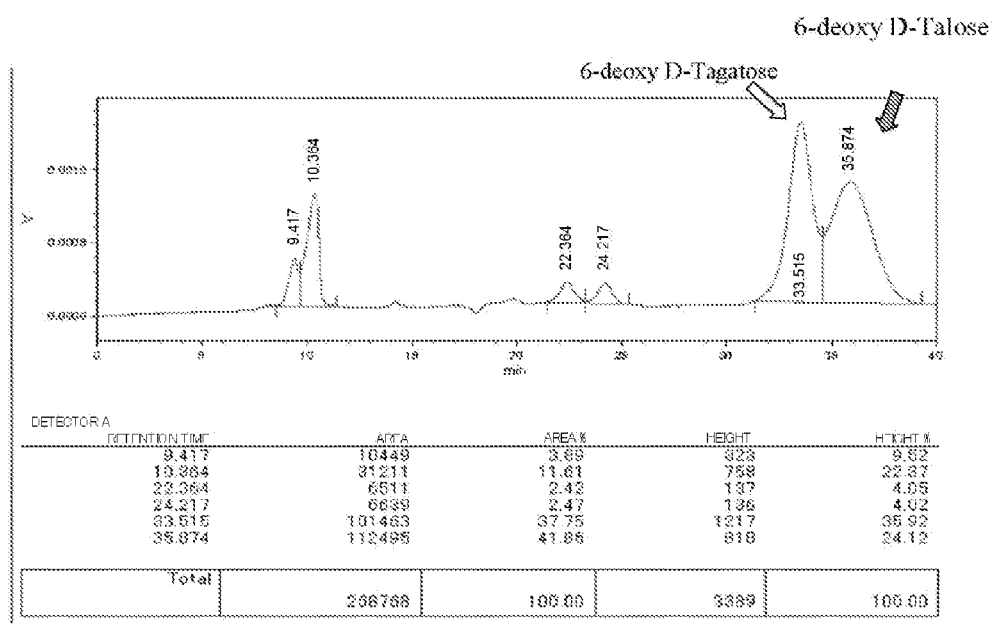

[Fig.57]
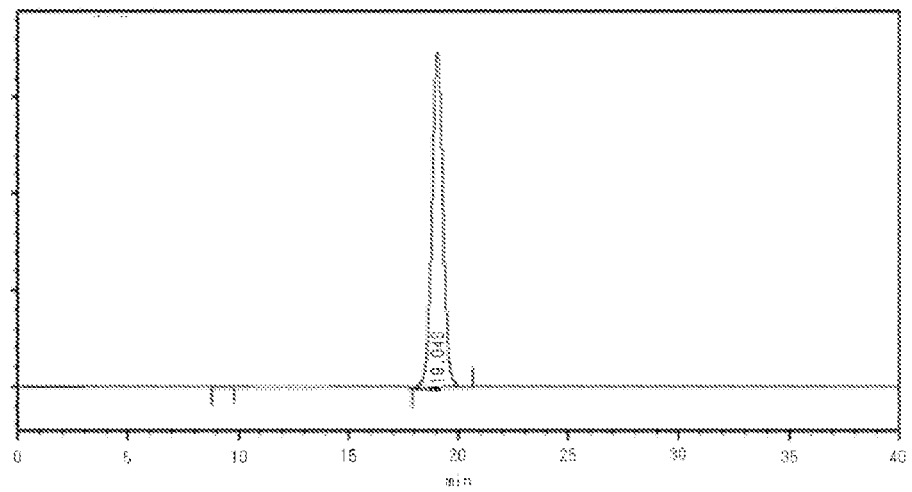
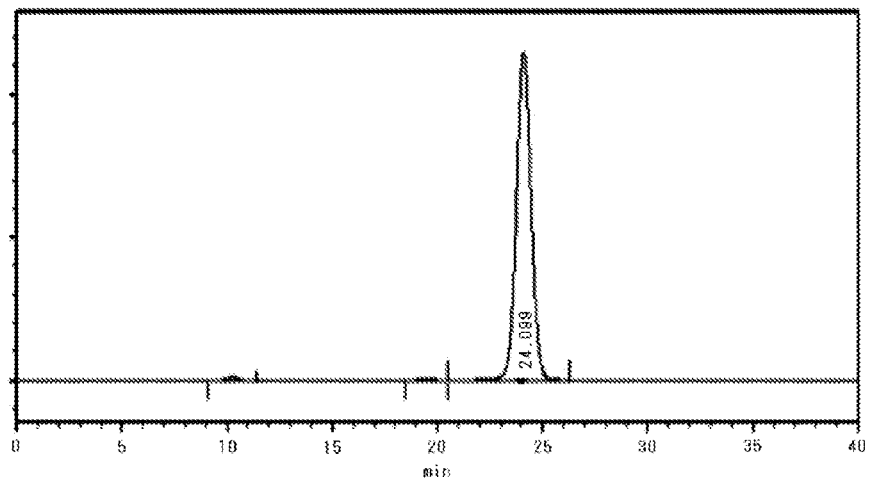

[Fig.58]
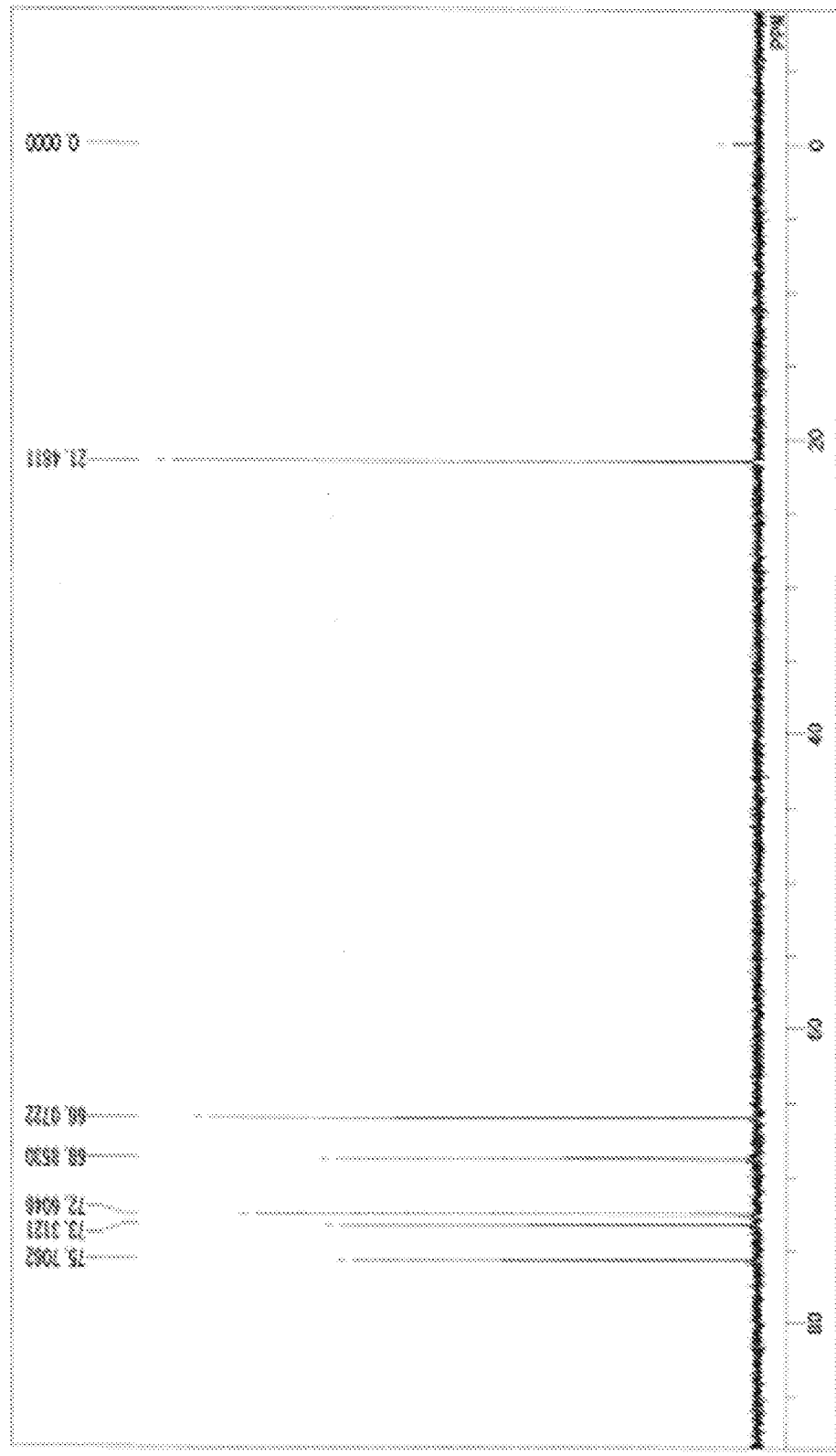

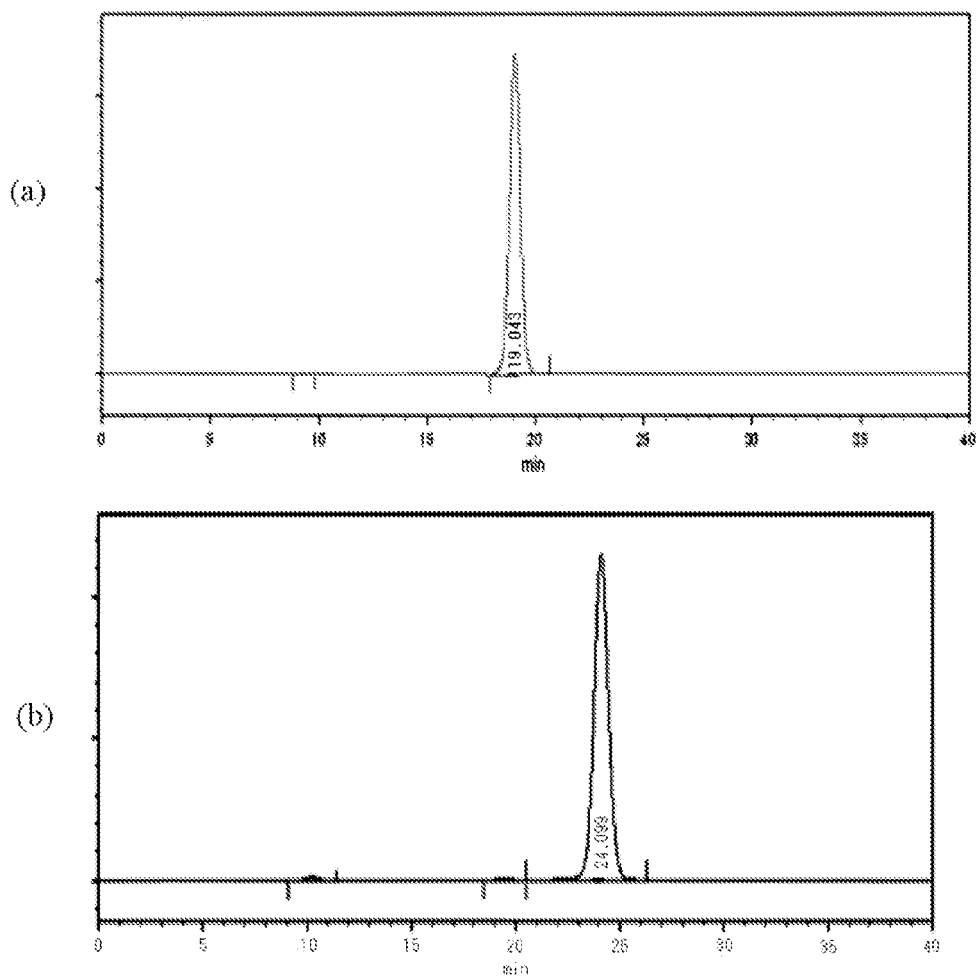
[Fig.59]

[Fig.60]
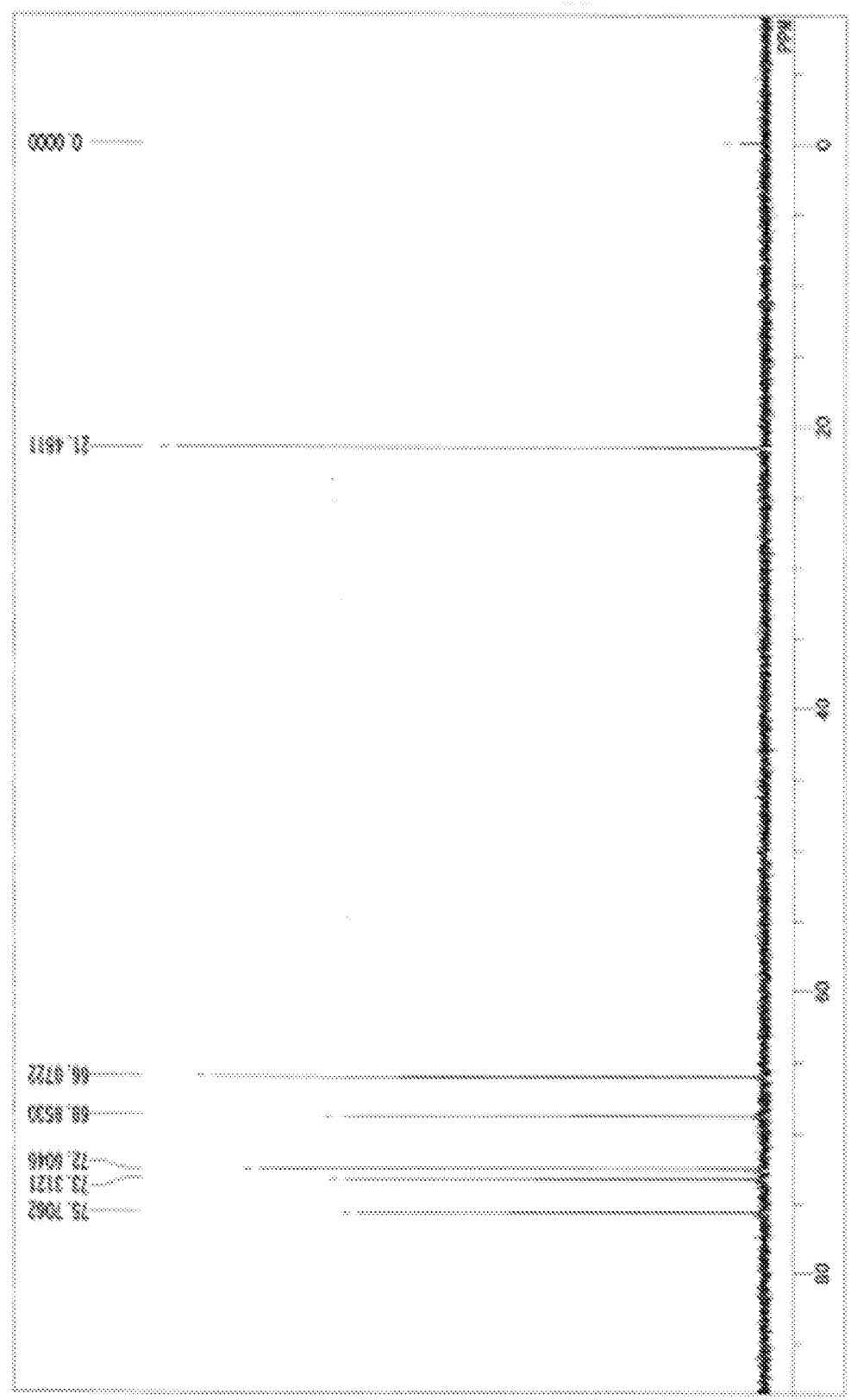

[Fig.61]
(a) 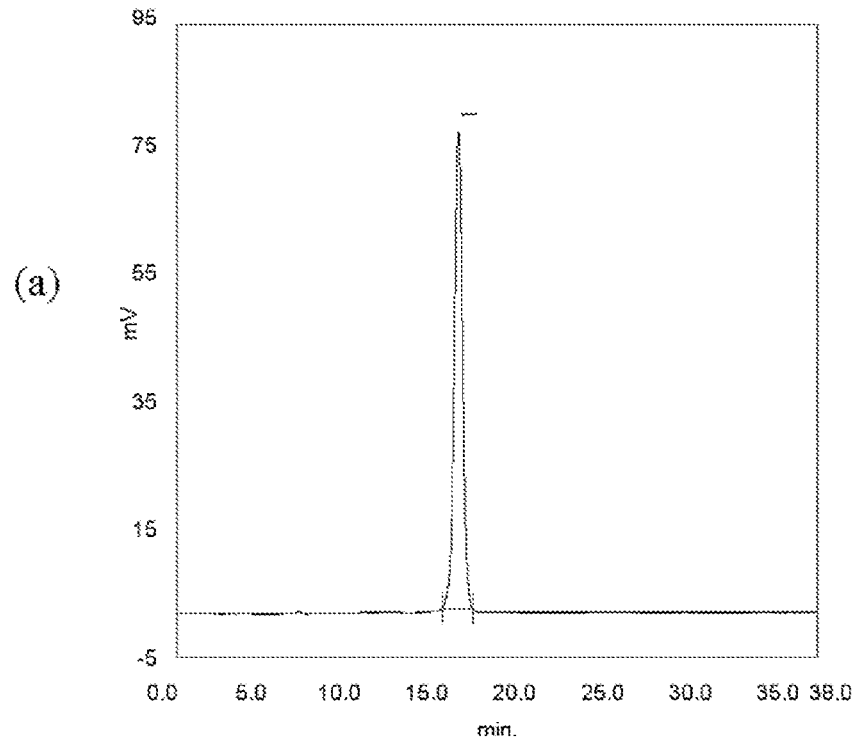
(b) 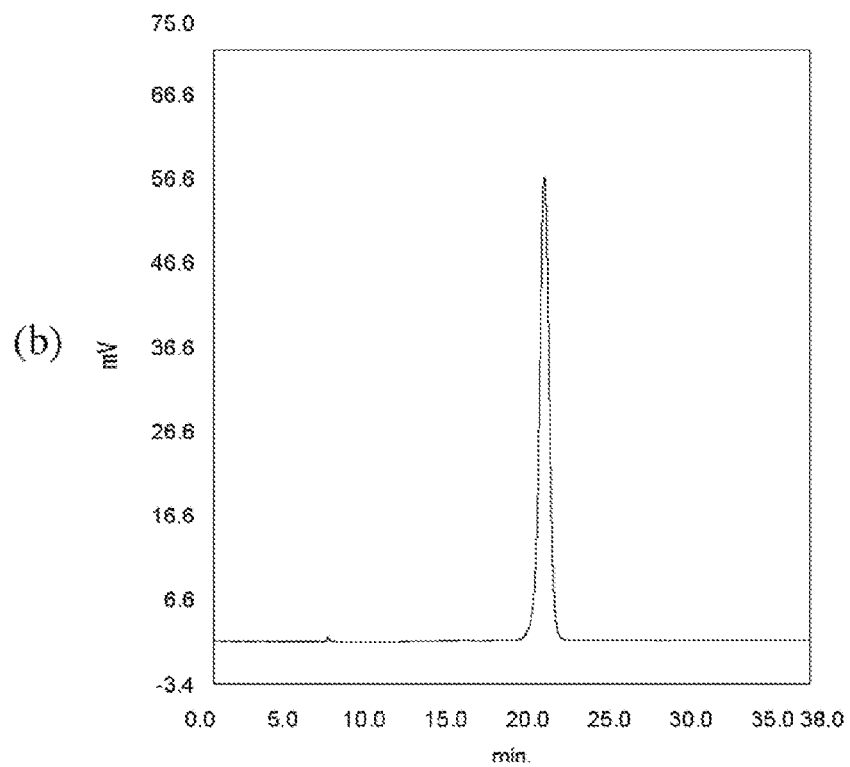

[Fig.62]
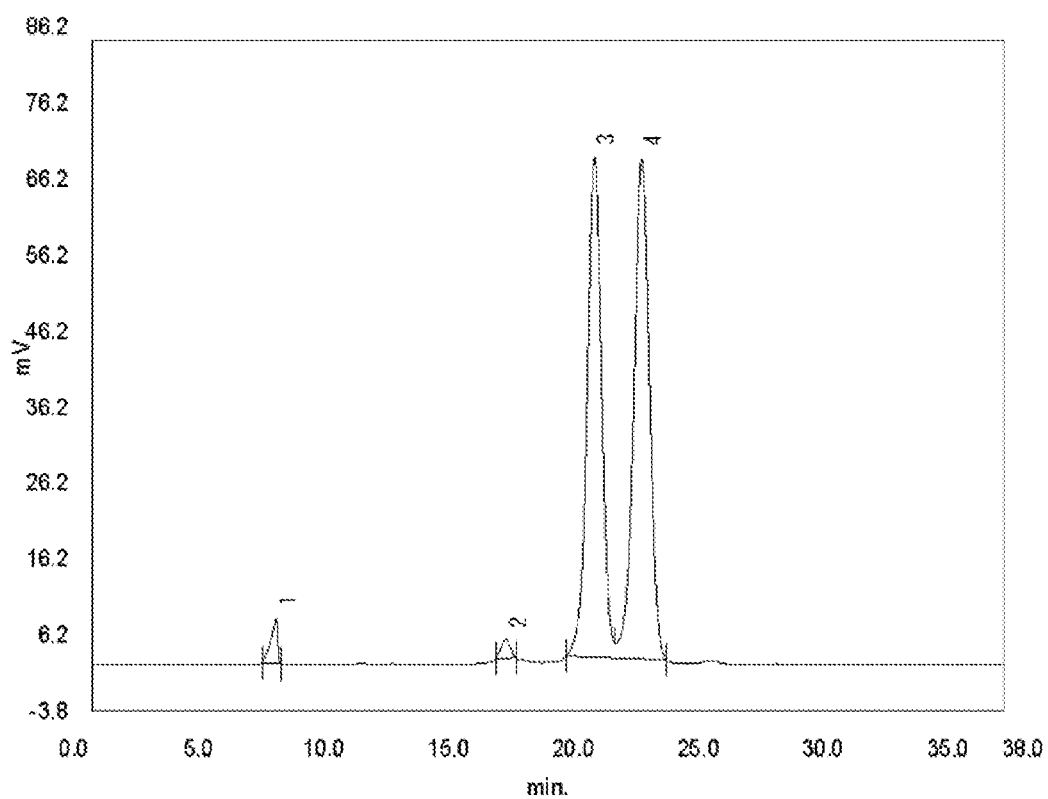

[Fig.63]
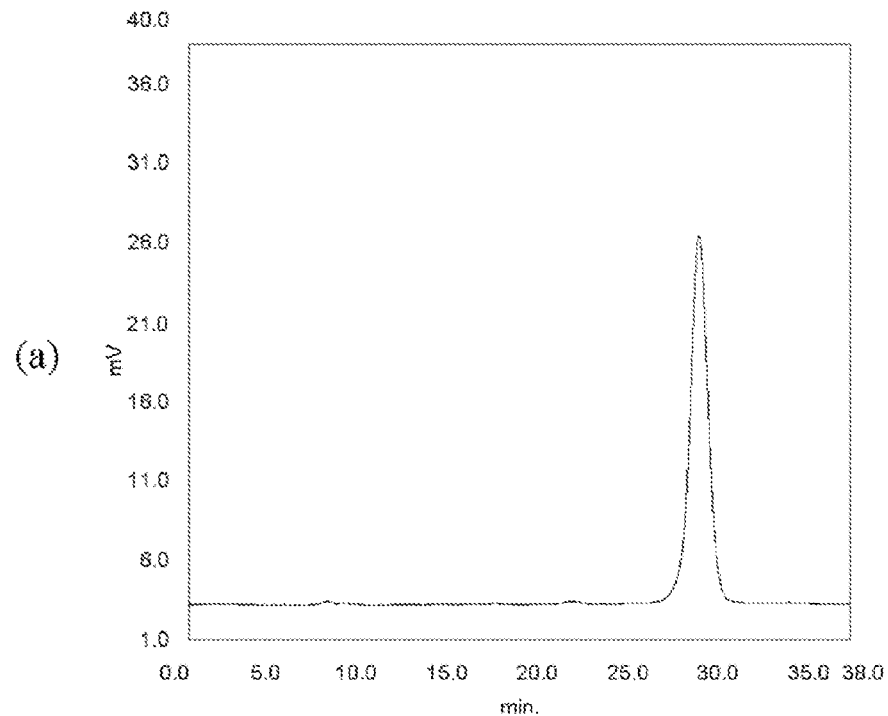
(a)
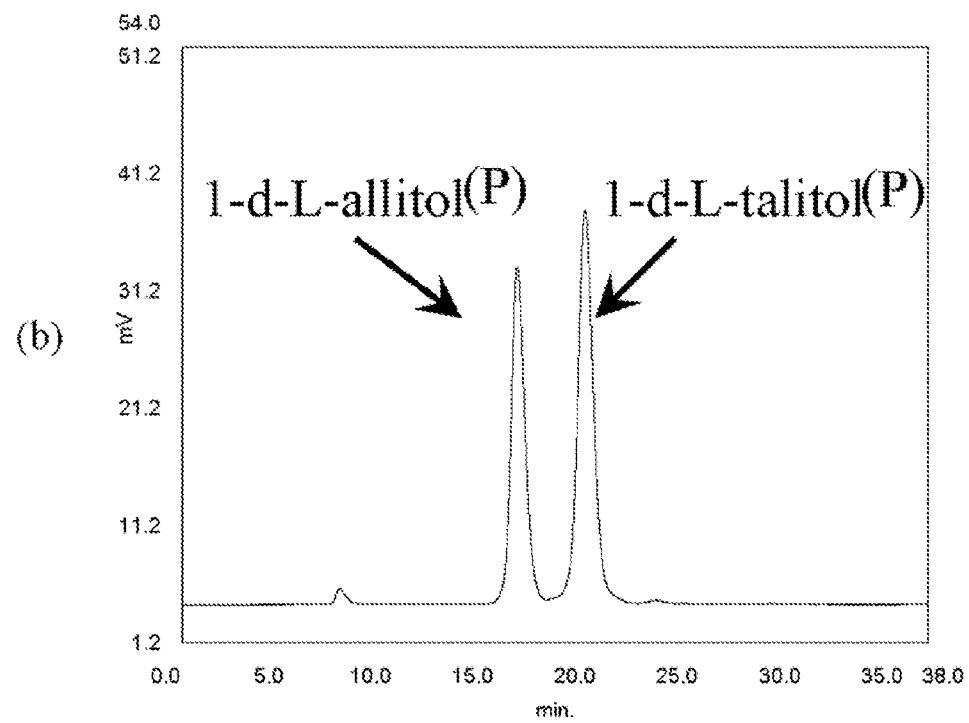
(b)

[Fig.64]

Deoxy hexoses in Deoxy-Izumoring

| # | <1- and 6-d-ketose> | <1- and 6-d-aldoses> | <1- and 6-d-polyols> |
|---|---|---|---|
| 1 | 1-d-D-fructose | 6-d-D-glucose | 1-d-D-glucitol = 6-d-D-gulitol |
| 2 | 1-d-D-psicose | 6-d-D-mannose | 1-d-D-mannitol = 6-d-D-mannitol |
| 3 | 1-d-D-tagatose | 6-d-D-allose | 1-d-D-allitol = 6-d-L-allitol |
| 4 | 1-d-D-sorbose | 6-d-D-altrose | 1-d-D-altritol = 6-d-D-talitol |
| 5 | 6-d-D-fructose | 6-d-D-talose | 1-d-D-talitol = 6-d-D-altritol |
| 6 | 6-d-D-psicose | 6-d-D-galactose | 1-d-D-galactitol = 6-d-L-galactitol |
| 7 | 6-d-D-tagatose | 6-d-D-idose | 1-d-D-iditol = 6-d-D-iditol |
| 8 | 6-d-D-sorbose | 6-d-D-gulose | 1-d-D-gulitol = 6-d-D-glucitol |
| 9 | 1-d-L-fructose | 6-d-L-glucose | 1-d-L-glucitol = 6-d-L-gulitol |
| 10 | 1-d-L-psicose | 6-d-L-mannose | 1-d-L-mannitol = 6-d-L-mannitol |
| 11 | 1-d-L-tagatose | 6-d-L-allose | 1-d-L-allitol = 6-d-D-allitol |
| 12 | 1-d-L-sorbose | 6-d-L-altrose | 1-d-L-altrirol = 6-d-L-talitol |
| 13 | 6-d-L-fructose | 6-d-L-talose | 1-d-L-talitol = 6-d-L-altritol |
| 14 | 6-d-L-psicose | 6-d-L-galactose | 1-d-L-galactitol = 6-d-D-galactitol |
| 15 | 6-d-L-tagatose | 6-d-L-idose | 1-d-L-iditol = 6-d-L-iditol |
| 16 | 6-d-L-sorbose | 6-d-L-gulose | 1-d-L-gulitol = 6-d-L-glucitol |

Total 48 ; 1- and 6 hexoses

DEOXYKETOHEXOSE ISOMERASE AND METHOD FOR PRODUCING DEOXYHEXOSE AND DERIVATIVE THEREOF USING SAME

TECHNICAL FIELD

The present invention relates to a deoxyketohexose isomerase and a method for producing deoxyhexose and derivatives thereof using the same.

BACKGROUND ART

A great number of complicated hydrocarbons play major roles in biological recognition processes such as recognitions between cells, cell growth and cell differentiation (non-patent reference 1). They compose blood type determinants (non-patent reference 2) and form cancer-related antigens (non-patent reference 3). In the plant kingdom, they exert coordination functions as hormones (non-patent reference 4) and form binding sites to lectin (non-patent reference 5).

For example, modified sugars such as deoxy- and fluoro-sugars and epimers of naturally occurring sugars provide important approaches for research works about interactions of them. Absolutely in the same manner as in the case of the interactions between specific enzymes and substrates, general rules about the interactions between proteins and carbohydrates are mostly focused in their association, interestingly. In other words, the information about the activity center of an enzyme can be obtained by continuous modifications of a substrate for the enzyme. Furthermore, attention is focused on deoxyglycosides, in particular, because of the fact that deoxyglycosides exist in a great number of antibiotics (non-patent reference 6).

It is reported that 2-deoxyglucose inhibits glycolysis in cancer cells and proliferation of cancer cells. It is also reported that 2-deoxyglucose delays cancer proliferation in some animal models. Additionally, research works are under way about combinations of other cytokines with anti-cancer drugs (patent reference 1). As described above, it is expected that deoxyhexose may be applicable to research works about metabolism and biological signals, in particular.

Izumori Ken as one of the inventors publicly discloses the Izumoring coordination scheme about tetrose, pentose and hexose in the patent reference 2 and describes the usefulness thereof. Specifically, the Izumoring coordination scheme is a scheme totally showing the coordination among all monosaccharides with 4 to 6 carbon atoms by linking them via production processes and molecular structures (D forms, L forms) as shown in FIG. 4. In other words, what is indicated in FIG. 4 is that all monosaccharides with 4, 5 and 6 carbon atoms are linked together. The whole scheme shows the linking in the Izumoring C6, the linking in the Izumoring C5, the linking in the Izumoring C4, and the linking of C4, C5 and C6 together. The concept is very important. So as to reduce the number of the carbon atoms, mainly, fermentation processes are used. The Izumoring scheme is characteristically a significant coordination scheme linking all monosaccharides with different carbon atoms together.

As shown in the lower column in FIG. 4, and in FIG. 5 and FIG. 8, the Izumoring of monosaccharides with 6 carbon atoms (hexose) shows that monosaccharides with 6 carbon atoms (hexose) include 34 types in total, where aldose includes 16 types; ketose includes eight types; and sugar alcohol includes 10 types. Rare sugars are defined as monosaccharides (aldose and ketose) and derivatives thereof (sugar alcohol) which exist rarely in the natural kingdom. Since the definition is not a definition according to the sugar structure or the sugar properties, the definition itself is so ambiguous. In other words, no definition about the amount such that rare sugars exist at a certain level or less is given. However, the aldose abundantly existing in the natural kingdom includes six types of D-glucose, D-galactose, D-mannose, D-ribose, D-xylose and L-arabinose. Therefore, aldose types except those described above are defined as rare sugars. D-Fructose exists as the ketose, while ketose types except D-fructose are defined as rare sugars. The other ketose types include D-psicose, D-tagatose, D-sorbose, L-fructose, L-psicose, L-tagatose and L-sorbose. Meanwhile, sugar alcohol is prepared by reducing monosaccharides. In the natural kingdom, D-sorbitol exists relatively abundantly, but sugar alcohols except D-sorbitol exist at so smaller amounts quantitatively that these sugar alcohols are also defined as rare sugars.

It has been known by research works including research works of the inventors that these sugars can be converted via redox enzyme reactions, aldose isomerase reactions, and aldose reduction enzyme reactions. D-Glucose (grape sugar) and D-fructose exist abundantly in the natural kingdom and are inexpensive, but these rare sugars have never been synthetically prepared yet. Herein, a novel enzyme was discovered. Quite unexpectedly, D-sorbose was found in a liquid culture of a bacterium generating an enzyme synthesizing D-sorbose from galactitol. That was the beginning. The cause was examined. Consequently, it was found that the bacterium generated an enzyme D-tagatose 3-epimerase (DTE) (patent reference 3). It is indicated that DTE is an enzyme linking between D-tagatose and D-sorbose, which have never been linked together. More surprisingly, DTE is an enzyme epimerizing all ketose types at position 3, and having such wide substrate specificity to interact with D-fructose and D-psicose, L-sorbose and L-tagatose, D-tagatose and D-sorbose, and L-psicose and L-fructose, which have never been synthetically connected together. In other words, it is indicated that the enzyme is a unique enzyme capable of selecting a substrate in a very wide range. Via the discovery of DTE, all monosaccharides are linked together in a ring shape, so that information about monosaccharides can be structurally constructed, which was designated Izumoring.

In a thorough view of FIG. 5, L forms are shown on the left side; D forms, on the right side; and DL forms, on the center. Additionally, L forms and corresponding D forms thereto locate to each other in point symmetry on the center (asterisk) of the ring. For example, D-glucose and L-glucose position to each other in point symmetry on the center point as the base. The value of Izumoring additionally resides in the design scheme for producing all monosaccharides. When intending to produce L-glucose from a starting material D-glucose, in the previous example, Izumoring shows that L-glucose can be prepared from D-glucose through isomerization, epimerization, reduction, oxidation, epimerization and isomerization.

Using Izumoring about monosaccharides with 6 carbon atoms (hexose), relations between sugars abundantly existing in the natural kingdom and rare sugars existing at a trace of amounts are shown. D-Glucose, D-fructose, D-mannose and D-galactose generated from lactose in cow milk exist abundantly in the natural kingdom, while sugars except those described above are grouped as rare sugars existing at extremely small amounts. The discovery of DTE enabled the production of D-fructose and D-psicose from D-glucose and also the production of D-allose, allitol and D-talitol. A rare sugar D-psicose has hardly been available so far, but a method for producing rare sugars from monosaccharides abundantly existing in the natural kingdom is now being developed. By utilizing the technique, the rare sugar D-psicose can be produced.

Herein, the meaning of Izumoring about monosaccharides with 6 carbon atoms is now described collectively below: all monosaccharides are structurally coordinated (structurally constructing information) via production processes and molecular structures (D forms, L forms) to catch the whole image of monosaccharides; an effective and efficient approach about research works thereof can be selected; an optimal production route can be designed; and defective parts may be anticipated.

Izumoring about monosaccharides with 5 carbon atoms (pentose) is of a ring smaller than the ring of Izumoring about monosaccharides with 6 carbon atoms, as shown in the middle column of FIG. 4 and in FIG. 6. Nonetheless, the Izumoring includes all of eight aldose types, four ketose types and four sugar alcohols, like C6 Izumoring, so that all monosaccharides are linked together via enzyme reactions. All the monosaccharides are linked together in a ring shape in the same manner except for a different point that the monosaccharides are produced only by redox reaction and isomerization reaction. It is indicated that by using DTE, a more efficient production route can be designed. As apparently shown in FIG. 6, in particular, the characteristic feature of the Izumoring with 5 carbon atoms is the symmetry on the right and left sides in contrast to the Izumoring with 6 carbon atoms, where all monosaccharides are arranged in point symmetry. Since all these pentose types are linked together with enzyme reactions, all the pentose types are structurally arranged (information construction) in the same manner as in the case of the Izumoring with 6 carbon atoms, so that the whole image can be given; an effective and efficient approach for research works about such pentose types can be selected; the optimal production route can be designed; and a defective part can be anticipated, significantly.

As shown in the upper column of FIG. 4 and FIG. 7, the Izumoring about monosaccharides with 4 carbon atoms (tetrose) cannot form a complete ring due to the characteristic structural feature of tetrose. The Izumoring with 4 carbon atoms has a structure corresponding to the upper half of the Izumoring with 5 carbon atoms. The ring is also in linking via redox and isomerization reactions absolutely in the same manner as the Izumoring with 5 to 6 carbon atoms does. Because DTE never reacts with ketose with 4 carbon atoms, currently, no reaction exists between ketose types. However, the existence of a novel epimerase is anticipated, so research works about the existence thereof are now under way.

The whole arrangement is in symmetry on the right and left sides, like the arrangement in the Izumoring with 5 carbon atoms and includes all four aldose types, two ketose types and three sugar alcohol types. In other words, the same meaning as the Izumoring with 5 and 6 carbon atoms exists.

D-Glucose in the Izumoring C6 is linked to D-arabitol in the Izumoring C5 and to erythritol in the Izumoring C4. The lines show that D-arabitol and erythritol can be produced from D-glucose by a fermentation method. In other words, the Izumoring C6, the Izumoring C5 and the Izumoring C4 are linked together. The linking is mainly due to reactions by fermentation, causing the reduction of carbon atoms. The Izumoring C6, the Izumoring C5 and the Izumoring C4 may be linked together by fermentation methods other than the two conversion reactions to D-arabitol and erythritol. For example, D-ribose may be produced from D-glucose.

As described above, all monosaccharides (aldose, ketose and sugar alcohol) with 4, 5 and 6 carbon atoms are linked together via the three Izumoring schemes. Therefore, the locations of individual monosaccharides in all the monosaccharides can be clearly identified. It is readily confirmed that the most famous Xylitol can be produced readily by reducing D-xylose prepared from wood pulp as a source not utilized.

In case that a specific monosaccharide is obtained abundantly via a reaction in a biological organism, the conversion of the specific monosaccharide to a novel monosaccharide will possibly be found readily. Because the locations of all monosaccharides as raw materials can securely be obtained on the basis of the whole image, a useful method for the utilization thereof can be designed. Particularly, the method for using any monosaccharide obtained from wastes or by-products can readily be anticipated.

When monosaccharides are reduced, aldehyde group and ketone group therein are converted to alcohol group, so that polyhydric alcohols with the same carbon atoms, namely sugar alcohols are produced. Many of reducing sugars are useful in fields of food, etc.; for example, L-arabinose as a pentose has a taste close to sucrose and is slightly absorbed, so L-arabinose is a non-caloric sugar. Additionally, it is known that disaccharides such as sucrose and maltose inhibit disaccharide hydrolases in exerting its function during the absorption thereof into biological bodies. It is expected that such disaccharides may be utilized as diet sweeteners or sweeteners for diabetic patients. Additionally, L-arabinose is a useful sugar as a raw material for synthetically preparing pharmaceutical products.

In case of intending to obtain reducing sugars, the origin may be screened for in naturally occurring materials. For example, recently, a method for producing L-arabinose comprising allowing an enzyme and an acid to react with corn fiber, gum Arabic and beet pulp has been developed as an approach for obtaining L-arabinose. Crude fibers such as arabinan, arabinoxylan and arabinogalactan as raw materials frequently exist in mixtures with for example pectin and unnecessary crude fiber. In solutions resulting from the enzyme decomposition and acid hydrolysis of them, pectin, crude fibers or decomposition products thereof in addition to reducing sugars such as L-arabinose are mixed together and concurrently exist. As to a method for purifying L-arabinose, there are proposed for example a method of fractionation of the intended L-arabinose from xylose and oligosaccharides in an L-arabinose-containing sugar solution by chromatography with ion exchange resins; a method by chromatography with ion exchange resins for the purpose of separating L-arabinose from polysaccharides, oligosaccharides and salts; and film treatment.

As to deoxy monosaccharides, alternatively, effective methods for producing such deoxy monosaccharides and substances recognized as deoxy monosaccharides are very few. Therefore, the establishment of a method for producing deoxy monosaccharides is first desired.

Patent reference 1: JP-T-2006-515883 (the term "JP-T" means a published Japanese translation of a PCT patent application)

Patent reference 2: WO 2004/063369

Patent reference 3: Japanese Patent 3,333,969

Non-patent reference 1: G. E. Edelman, Spektrum Wiss. 1964 (6), 62

Non-patent reference 2: V. Ginsburg, Adv. Enzymol. 36, (1972), 131

Non-patent reference 3: G. M. W. Cook, E. W. Stoddard, "Surface carbohydrates of the Eucaryotic Cell", Academic Press, London, 1973

Non-patent reference 4: P. Albersheim, A. G. Darvill, Spektrum Wiss. 1985(11), 86

Non-patent reference 5: T. W. Rademacher, R. B. Parekh, R. A. Dwek, Ann. Rev. Biochem., 57, (1988), 785

Non-patent reference 6: T. Reichstein, E. Weiss, Adv. Carbohydr. Chem. 17, (9162[sic]), 65

DISCLOSURE OF THE INVENTION

Problems that the Invention is to Solve

It has been strongly desired that a method for industrially producing a deoxy monosaccharide at steps of a number as small as possible in a ready manner is to be established. Therefore, Izumoring of deoxy monosaccharides is to be constructed, along with the establishment of a systematic method for producing such deoxy monosaccharide using the Izumoring.

Specifically, it is an object of the invention to provide a deoxyketohexose isomerase interacting with 1- or 6-deoxyketohexose to epimerize the 1- or 6-dexoyketohexose as it remains the free deoxy sugar, to produce a deoxy product resulting from the epimerization at position 3.

Additionally, it is an object of the invention to accomplish Deoxy-Izumoring corresponding to the Izumoring of monosaccharides with 6 carbon atoms (hexose), using the enzyme.

It is another object of the invention to provide 1- or 6-deoxy monosaccharides corresponding to all of aldohexose, ketohexose and sugar alcohol as well as a systematic, specific and economical method for producing the same.

Means for Solving the Problems

The inventors made investigations so as to establish a method for producing deoxy monosaccharides. In the course, the inventors found that D-tagatose 3-epimerase derived from *Pseudomonas cichorii* ST-24 (FERM BP-2736) could generate 6-deoxyhexose (for example 6-deoxy L-psicose), using the corresponding substrate 6-deoxyhexose (for example 6-deoxy L-fructose). The inventors found that L-rhamnose isomerase catalyzed the isomerization reaction between other deoxyketose monosaccharides and deoxyaldose monosaccharides such as the isomerization reaction between 6-deoxy L-psicose and 6-deoxy L-altrose, in addition to the conventionally known enzyme reaction between L-rhamnose and 6-deoxy L-fructose. Further, the inventors found that 1- or 6-deoxy monosaccharides and 1- or 6-deoxy sugar alcohols could be produced by an additional combination with redox reactions. Thus, the invention has been achieved. In such manner, Deoxy-Izumoring as the Izumoring corresponding to such deoxy products could be completely prepared. FIG. 1 shows Deoxy-Izumoring of deoxyhexose types linked together. FIG. 2 shows Deoxy-Izumoring where the names of individual deoxy sugars composing the Izumoring in FIG. 1 are described and attached. FIG. 3 shows Deoxy-Izumoring where the individual deoxy sugars are numbered. The numbers in FIG. 3 and the names of deoxy sugars are as follows.

1 6-Deoxy D-gulitol
2 6-Deoxy D-sorbose
3 6-Deoxy D-tagatose
4 6-Deoxy D-talitol
5 1-Deoxy D-altritol
6 1-Deoxy D-psicose
7 1-Deoxy D-fructose
8 1-Deoxy D-mannitol
9 6-Deoxy D-mannitol
10 6-Deoxy D-fructose
11 6-Deoxy D-psicose
12 6-Deoxy D-altritol
13 1-Deoxy D-talitol
14 1-Deoxy D-tagatose
15 1-Deoxy D-sorbose
16 1-Deoxy D-gulitol
17 6-Deoxy L-glucitol
18 6-Deoxy L-fructose
19 6-Deoxy L-psicose
20 6-Deoxy L-altritol
21 1-Deoxy L-talitol
22 1-Deoxy L-tagatose
23 1-Deoxy L-sorbose
24 1-Deoxy L-iditol
25 6-Deoxy L-iditol
26 6-Deoxy L-sorbose
27 6-Deoxy L-tagatose
28 6-Deoxy L-talitol
27 1-Deoxy L-altritol
30 1-Deoxy L-psicose
31 1-Deoxy L-fructose
32 1-Deoxy L-glucitol
33 6-Deoxy D-iditol
34 6-Deoxy D-galactitol
35 1-Deoxy D-allitol
36 1-Deoxy D-glucitol
37 6-Deoxy D-glucitol
38 6-Deoxy D-allitol
39 1-Deoxy D-galactitol
40 1-Deoxy D-iditol
41 6-Deoxy L-mannitol
42 6-Deoxy L-allitol
43 1-Deoxy L-galactitol
44 1-Deoxy L-gulitol
45 6-Deoxy L-gulitol
46 6-Deoxy L-galactitol
47 1-Deoxy L-allitol
48 1-Deoxy L-mannitol
47 6-Deoxy D-gulose
50 6-Deoxy D-idose
51 6-Deoxy D-galactose
52 6-Deoxy D-talose
53 6-Deoxy D-mannose
54 6-Deoxy D-glucose
55 6-Deoxy D-allose
56 6-Deoxy D-altrose
57 6-Deoxy L-glucose
58 6-Deoxy L-mannose
59 6-Deoxy L-allose
60 6-Deoxy L-altrose
61 6-Deoxy L-idose
62 6-Deoxy L-gulose
63 6-Deoxy L-galactose
64 6-Deoxy L-talose The gist of the invention resides in the deoxyketohexose isomerase described below in (1) through (4).

(1) A deoxyketohexose isomerase which can be obtained from a bacterium of the genus *Pseudomonas*, the deoxyketohexose isomerase interacting with 1- or 6-deoxyketohexose to epimerize the 1- or 6-deoxyketohexose as it remains the free deoxy sugar, to produce a deoxy product resulting from the epimerization at position 3.

(2) A deoxyketohexose isomerase described above in (1), epimerizing 1-deoxy D-ketohexose or 6-deoxy D-ketohexose or 1-deoxy L-ketohexose or 6-deoxy L-ketohexose at position 3 to generate the corresponding 1-deoxy D-ketohexose or 6-deoxy D-ketohexose or 1-deoxy L-ketohexose or 6-deoxy L-ketohexose.

(3) A deoxyketohexose isomerase which can be obtained from a bacterium of the genus *Pseudomonas*, the deoxyketohexose isomerase having the following physico-chemical properties:

1) epimerizing 1- or 6-deoxy D-ketohexose, and 1- or 6-deoxy L-ketohexose at position 3 to generate the corresponding 1- or 6-deoxy D-ketohexose and 1- or 6-deoxy L-ketohexose, respectively;

2) the optimal pH and pH stability of D-ketohexose 3-epimerase: the optimal pH is at pH 7 to 10, while the D-ketohexose 3-epimerase is stable at pH 5 to 10;

3) the optimal temperature and thermal stability of D-ketohexose 3-epimerase activity: the optimal temperature around 60° C., while the epimerase is stable at 50° C. or less;

4) the ultraviolet absorption spectrum: an absorption band at 275 to 280 nm;

5) the molecular weight of 41,000±3,000 (by gel filtration chromatography).

(4) A deoxyketohexose isomerase described above in (1), (2) or (3), where the deoxyketohexose isomerase is an enzyme derived from *Pseudomonas cichorii* ST-24 (FERM BP-2736).

The gist of the invention resides in a method for producing deoxyketohexose and a derivative thereof as described below in (5) to (17).

<Between Ketose Types>

(5) A method for producing deoxyketohexose and a derivative thereof, comprising epimerizing a raw material 1-deoxy D-ketohexose or 6-deoxy D-ketohexose or 1-deoxy L-ketohexose or 6-deoxy L-ketohexose at position 3, using the deoxyketohexose isomerase described above in (1), (2), (3) or (4), to produce the corresponding 1-deoxy D-ketohexose or 6-deoxy D-ketohexose or 1-deoxy L-ketohexose or 6-deoxy L-ketohexose as an intended product.

<Ketose→Reduction→Sugar Alcohol>

(6) A method for producing deoxyketohexose and a derivative thereof as described above in (5), where the derivative is prepared by reducing deoxyketohexose, the method comprising reducing the intended product 1-deoxy D-ketohexose or 6-deoxy D-ketohexose or 1-deoxy L-ketohexose or 6-deoxy L-ketohexose to generate the corresponding 1-deoxy D-sugar alcohol or 6-deoxy D-sugar alcohol, or 1-deoxy L-sugar alcohol or 6-deoxy L-sugar alcohol as a derivative thereof.

<Ketose→Reduction→Sugar Alcohol→Oxidation→Ketose>

(7) A method for producing deoxyketohexose and a derivative thereof as described above in (5), where the derivative is prepared by reducing deoxyketohexose followed by oxidation, the method comprising reducing the intended product 1-deoxy D-ketohexose or 6-deoxy D-ketohexose or 1-deoxy L-ketohexose or 6-deoxy L-ketohexose to generate the corresponding 1-deoxy D-sugar alcohol or 6-deoxy D-sugar alcohol, or 1-deoxy L-sugar alcohol or 6-deoxy L-sugar alcohol as a derivative thereof, and then oxidizing the 1-deoxy D-sugar alcohol or 6-deoxy D-sugar alcohol, or 1-deoxy L-sugar alcohol or 6-deoxy L-sugar alcohol to produce the corresponding 6-deoxy D-ketohexose or 1-deoxy D-ketohexose or 6-deoxy L-ketohexose or 1-deoxy L-ketohexose.

<Ketose→Aldose (Only Existing as 6-Deoxy Form)>

(8) A method for producing deoxyketohexose and a derivative thereof as described above in (5), where the derivative is prepared by isomerizing 6-deoxyketohexose, the method comprising allowing aldose isomerase to interact with the intended product 6-deoxy D-ketohexose or 6-deoxy L-ketohexose to produce the corresponding 6-deoxy D-aldohexose or 6-deoxy L-aldohexose as a derivative thereof.

<Ketose→Aldose→Sugar Alcohol>

(9) A method for producing deoxyketohexose and a derivative thereof as described above in (5), where the derivative is prepared by isomerizing and then reducing deoxyketohexose, the method comprising allowing aldose isomerase to interact with the intended product 6-deoxy D-ketohexose or 6-deoxy L-ketohexose to produce the corresponding 6-deoxy D-aldohexose or 6-deoxy L-aldohexose as a derivative thereof, and allowing aldose reductase to interact with the 6-deoxy D-aldohexose or 6-deoxy L-aldohexose to produce the corresponding 6-deoxy D-sugar alcohol or 6-deoxy L-sugar alcohol.

<Aldose→Isomerization→Ketose→Epimerization→Ketose>

(10) A method for producing deoxyketohexose and a derivative thereof as described above in (5), where 6-deoxy D-ketohexose or 6-deoxy L-ketohexose as a raw material for enzyme interaction is produced by allowing aldose isomerase to interact with 6-deoxy D-aldohexose or 6-deoxy L-aldohexose to produce the corresponding 6-deoxy D-ketohexose or 6-deoxy L-ketohexose, the method additionally comprising epimerizing the product 6-deoxy D-ketohexose or 6-deoxy L-ketohexose to produce the corresponding 6-deoxy D-ketohexose or 6-deoxy L-ketohexose as the intended product.

<Sugar Alcohol→Oxidation→Ketose→Epimerization→Ketose>

(11) A method for producing deoxyketohexose and a derivative thereof according to claim 5, where 1-deoxy D-ketohexose or 6-deoxy D-ketohexose or 1-deoxy L-ketohexose or 6-deoxy L-ketohexose as a raw material is produced by oxidizing 1-deoxy D-sugar alcohol or 6-deoxy D-sugar alcohol or 1-deoxy L-sugar alcohol or 6-deoxy L-sugar alcohol to produce the corresponding 1-deoxy D-ketohexose or 6-deoxy D-ketohexose or 1-deoxy L-ketohexose or 6-deoxy L-ketohexose, the method additionally comprising epimerizing the resulting product to produce the corresponding 1-deoxy D-ketohexose or 6-deoxy D-ketohexose or 1-deoxy L-ketohexose or 6-deoxy L-ketohexose as the intended product.

(12) A method for producing deoxyketohexose and a derivative thereof as described above in (6), (7) or (11), where polyol dehydrogenase is used or a hydrogenation process using Raney nickel as a catalyst is used, for the oxidation reaction or reduction reaction.

(13) A method described above in (7) or (11), where a bacterial strain IK7 (NITE BP-271) of the genus *Enterobacter* and with a potency of generating dehydrogenase is used for the oxidation reaction.

<Aldose→Reduction→Sugar Alcohol→Oxidation→Ketose→Epimerization→Ketose>

(14) A method for producing deoxyketohexose and a derivative thereof as described above in (5), where the raw material 1- or 6-deoxy D-ketohexose or 1- or 6-deoxy L-ketohexose is produced by allowing aldose reductase to interact with 6-deoxy D-aldohexose or 6-deoxy L-aldohexose or via a reduction reaction of organic chemistry, to produce the corresponding 6-deoxy D-sugar alcohol or 6-deoxy L-sugar alcohol and then oxidizing the resulting sugar alcohol to produce the corresponding 1- or 6-deoxy D-ketohexose or 1- or 6-deoxy L-ketohexose, the method additionally comprising epimerizing the 1- or 6-deoxy D-ketohexose or 1- or 6-deoxy L-ketohexose to produce the corresponding 1- or 6-deoxy D-ketohexose or f- or 6-deoxy L-ketohexose as the intended product.

(15) A method for producing deoxyketohexose and a derivative thereof described above in (9) or (14), where aldose reductase is used or a chemical reduction process is used, for the reduction reaction.

(16) A method for producing deoxyketohexose or a derivative thereof as described above in (8), (9) or (10), where L-rhamnose isomerase is used for the isomerization reaction.

(17) A method for producing deoxyketohexose and a derivative thereof as described above in (8), (9) or (10), where L-rhamnose isomerase is used for the isomerization reaction for isomerization of 6-deoxy L-psicose to 6-deoxy L-altrose.

The gist of the invention resides in the novel compounds described below in (18).

(18) The following novel compounds produced by any of the methods described above in (5) through (17): 6-deoxy D-sorbose, 6-deoxy D-tagatose, 1-deoxy D-psicose, 1-deoxy D-fructose, 6-deoxy D-fructose, 6-deoxy D-psicose, 1-deoxy D-tagatose, 1-deoxy D-sorbose, 6-deoxy L-fructose, 6-deoxy L-psicose, 1-deoxy L-tagatose, 1-deoxy L-sorbose, 6-deoxy L-sorbose, 6-deoxy L-tagatose, 1-deoxy L-psicose, 1-deoxy L-fructose, 6-deoxy D-gulose, 6-deoxy D-idose, 6-deoxy D-galactose, 6-deoxy D-talose, 6-deoxy D-mannose, 6-deoxy D-glucose, 6-deoxy D-allose, 6-deoxy D-altrose, 6-deoxy L-glucose, 6-deoxy L-allose, 6-deoxy L-altrose, 6-deoxy L-idose, 6-deoxy L-gulose, 6-deoxy L-talose, 1-deoxy L-glucitol or 6-deoxy D-gulitol, 6-deoxy D-iditol or 1-deoxy D-iditol.

Advantages of the Invention

In accordance with the invention, there are provided deoxyketohexose isomerase interacting with free 1- or 6-deoxyketohexose; a method for producing 1- or 6-deoxyketohexose using the same; and the produced 1- or 6-deoxyketohexose.

As to rare sugars as monosaccharides rarely existing in the natural kingdom and derivatives thereof (aldose, ketose and sugar alcohol), additionally, the Izumoring of monosaccharides with 6 carbon atoms and derivatives thereof (hexose) shows relations between sugars abundantly existing in the natural kingdom and rare sugars existing at extremely small amounts, and starting raw materials and routes for obtaining such sugars. In accordance with the invention, the Izumoring can be developed into Deoxy-izumoring where 1- or 6-deoxy products corresponding to monosaccharides with 6 carbon atoms and derivatives thereof (aldose, ketose, and sugar alcohol) are linked together.

In the Deoxy-izumoring, 1- or 6-deoxy products corresponding to monosaccharides with 6 carbon atoms and derivatives thereof (aldose, ketose, sugar alcohol), namely deoxy rare sugars (deoxyketohexose, deoxyaldohexose) and derivatives thereof, i.e. deoxy sugar alcohols are linked together in such a manner that the relations between enzymatic oxidation, enzymatic or chemical reduction or isomerization are demonstrated, leading to efficient production.

BRIEF DESCRIPTION OF DRAWINGS

FIG. 1 Depicting Deoxy-Izumoring where deoxyhexose is linked together.

FIG. 2 Depicting Deoxy-Izumoring with attached names of deoxy sugars.

FIG. 3 Depicting Deoxy-Izumoring with numbered deoxy sugars.

FIG. 4 Depicting routes for producing Izumoring where tetrose, pentose and hexose are linked together.

FIG. 5 Depicting routes for producing Izumoring where hexose is linked together.

FIG. 6 Depicting routes for producing Izumoring where pentose is linked together.

FIG. 7 Depicting routes for producing Izumoring where tetrose is linked together.

FIG. 8 Depicting an explanatory view of Izumoring C6 with a set of structural formulas.

FIG. 9 Depicting the equilibrium ratio between L-rhamnose and 6-deoxy L-fructose.

FIG. 10 Depicting the HPLC analysis results of a solution of L-rhamnose and 6-deoxy L-fructose.

FIG. 11 Depicting the equilibrium ratio between L-rhamnose, 6-deoxy L-fructose and 6-deoxy L-psicose.

FIG. 12 Depicting the HPLC analysis results of a solution of L-rhamnose, 6-deoxy L-fructose and 6-deoxy L-psicose.

FIG. 13 Depicting the HPLC analysis results of solutions in the individual tanks of L-rhamnose, 6-deoxy L-fructose and 6-deoxy L-psicose.

FIG. 14 Depicting the HPLC analysis results of solutions of 6-deoxy L-psicose and 6-deoxy L-altrose.

FIG. 15 $^{13}$C NMR of the product 1-deoxy D-psicose and chemically synthesized 1-deoxy D-psicose and the results of comparison of the structures thereof to each other.

FIG. 16 Proton NMR of the product 1-deoxy D-psicose and chemically synthesized 1-deoxy D-psicose and the results of comparison of the structures thereof to each other, where the upper NMR chart is for the chemical synthesized psicose, while the lower NMR chart is for the product at the present experiment.

FIG. 17 NMR spectra of chemically synthesized 1-deoxy L-fructose and the product and the results of comparison. $^{13}$C NMR of 1-deoxy D-psicose is shown on the upper column, while $^{13}$C NMR of the 1-deoxy L-fructose experimentally produced is shown on the lower column.

FIG. 18 NMR spectra of chemically synthesized 1-deoxy L-fructose and the product and the results of comparison. Proton NMR of 1-deoxy D-psicose is shown on the upper column, while proton NMR of the 1-deoxy L-fructose experimentally produced is shown on the lower column.

FIG. 19 Depicting the HPLC analysis results of 1-deoxy D-tagatose produced in Example 10.

FIG. 20 Depicting $^{13}$C NMR of 1-deoxy D-tagatose produced in Example 10.

FIG. 21 Depicting HPLC analysis results of 6-deoxy D-tagatose produced in Example 10.

FIG. 22 Depicting $^{13}$C NMR of 6-deoxy D-tagatose produced in Example 10.

FIG. 23 Depicting reactions for producing 6-deoxy L-psicose using L-rhamnose isomerase and D-tagatose 3-epimerase, from L-rhamnose.

FIG. 24 Depicting chemical reduction reactions of 6-deoxy L-psicose to 1-deoxy D-allitol and 1-deoxy D-talitol.

FIG. 25 Depicting biochemical reactions of deoxy D-allitol to 6-deoxy L-psicose.

FIG. 26 Depicting the time course of chemical reduction reactions of 6-deoxy L-psicose to 1-deoxy D-allitol and 1-deoxy D-talitol as well as HPLC chromatograph analysis results thereof.

FIG. 27 Depicting the time course of a biochemical reaction of deoxy D-allitol to 6-deoxy L-psicose as well as HPLC chromatograph analysis results thereof.

FIG. 28 A photograph of the crystal of 6-deoxy L-psicose produced in Example 10 in place of a drawing.

FIG. 29 Depicting NMR spectra of chemically synthesized 6-deoxy L-psicose and the product in Example 11, together with the comparative results thereof. $^{13}$C NMR of 6-deoxy L-psicose is shown on the left side, while on the right side, $^{13}$C NMR of 6-deoxy L-psicose produced in Example 11 is shown.

FIG. 30 Depicting HPLC analysis results of purified 6-deoxy L-fructose.

FIG. 31 Depicting NMR spectra of chemically synthesized 6-deoxy L-fructose (standard) and the produced 6-deoxy L-fructose, and the comparative results thereof. $^{13}$C NMR of the standard is shown on the upper column, while $^{13}$C NMR of the 6-deoxy L-fructose produced in the experiment is shown on the lower column.

FIG. 32 Depicting $^{13}$C NMR spectrum of the produced 1-deoxy L-psicose.

FIG. 33 Depicting $^{13}$C NMR spectra of L-rhamnose and 6-deoxy L-mannitol.

FIG. 34 Depicting $^{13}$C NMR spectra of 6-deoxy L-mannitol, 1-deoxy L-fructose and the product isolated.

FIG. 35 Depicting $^{13}$C NMR spectra of 1-deoxy L-fructose, 1-deoxy L-psicose and the product isolated.

FIG. 36 Depicting the process of producing 1-deoxy L-psicose en route 6-deoxy L-mannitol and 1-deoxy L-fructose from L-rhamnose in chemical reaction formulas.

FIG. 37 Depicting HPLC analysis results of a solution of 6-deoxy L-tagatose and 6-deoxy L-sorbose as a reaction mixture in Example 14.

FIG. 38 Depicting HPLC analysis results of 6-deoxy L-sorbose produced in Example 14.

FIG. 39 Depicting HPLC analysis results of a solution of 6-deoxy D-tagatose and 6-deoxy D-sorbose as a reaction mixture in Example 15.

FIG. 40 Depicting HPLC analysis results of 1-deoxy L-fructose (a) and 1-deoxy L-psicose (b) separated from a reaction mixture in Example 16.

FIG. 41 Depicting $^{13}$C NMR spectrum of 1-deoxy L-psicose isolated in Example 16.

FIG. 42(a) shows the HPLC analysis results of 6-deoxy D-psicose before reaction and FIG. 42(b) shows the HPLC analysis results thereof after reaction in Example 17.

FIG. 43(a) shows the HPLC analysis results of 6-deoxy L-tagatose before reaction and FIG. 43(b) shows the HPLC analysis results thereof after reaction in Example 18.

FIG. 44(a) shows the HPLC analysis results of a reaction mixture after reaction and FIG. 44(b) shows the HPLC analysis results of the produced 1-deoxy D-tagatose in Example 19.

FIG. 45 Depicting $^{13}$C NMR spectrum of 1-deoxy D-tagatose produced in Example 19.

FIG. 46 HPLC analysis results in the course of producing 1-deoxy L-tagatose in Example 20.

FIG. 47(a) shows the HPLC analysis results of a reaction mixture after reaction and FIG. 47(b) shows the HPLC analysis results of the isolated and purified 1-deoxy D-tagatose in Example 21.

FIG. 48 Depicting $^{13}$C NMR spectrum of 1-deoxy D-tagatose produced in Example 21.

FIGS. 49(a) and (b) show HPLC analysis results of L-rhamnitol and 1-deoxy L-fructose isolated and purified, respectively in Example 22.

FIG. 50 Depicting $^{13}$C NMR spectrum of 1-deoxy L-fructose produced in Example 22.

FIGS. 51(a), (b), (c) and (d) show HPLC analysis results of a mixture of 1-deoxy L-allitol and 1-deoxy L-talitol before reaction, a reaction mixture of 6-deoxy D-psicose and 6-deoxy L-tagatose after reaction, isolated and purified 6-deoxy D-psicose and isolated and purified 6-deoxy L-tagatose, respectively in Example 23.

FIG. 52(a) shows the HPLC analysis results of a reaction mixture after reaction and FIG. 52 (b) shows the HPLC analysis results of the isolated and purified 6-deoxy L-tagatose in Example 24.

FIG. 53 Depicting $^{13}$C NMR spectrum of 6-deoxy L-tagatose produced in Example 24.

FIGS. 54 (a) and (b) show HPLC analysis results of a reaction mixture after reaction, and isolated and purified 6-deoxy D-talose, respectively and FIG. 54(c) shows the $^{13}$C NMR spectrum of isolated and purified 6-deoxy D-talose, in Example 25.

FIGS. 55 (a) and (b) show HPLC analysis results of 6-deoxy D-psicose used as a substrate and a reaction mixture after reaction, respectively, in Example 26.

FIG. 56 HPLC analysis results of a mixture of 6-deoxy D-tagatose and 6-deoxy D-talose after the interaction of 6-deoxy D-tagatose with L-ribose isomerase in Example 27.

FIGS. 57 (a) and (b) show HPLC analysis results of D-fucose before reduction and 6-deoxy L-galactitol after reduction in Example 28.

FIG. 58 $^{13}$C NMR spectrum of 6-deoxy L-galactitol produced in Example 29.

FIGS. 59 (a) and (b) show HPLC analysis results of L-fucose before reduction and 6-deoxy D-galactitol after reduction in Example 29.

FIG. 60 Depicting $^{13}$C NMR spectrum of 6-deoxy D-galactitol produced in Example 29.

FIGS. 61 (a) and (b) show HPLC analysis results of L-rhamnose before reduction and L-rhamnitol after reduction in Example 30.

FIG. 62 HPLC analysis results of a mixture of 1-deoxy L-mannitol and 1-deoxy L-sorbitol after reduction in Example 31.

FIG. 63 HPLC analysis results of a mixture of 1-deoxy L-allitol and 1-deoxy L-talitol after reduction in Example 32.

FIG. 64 Listing all deoxy sugars (eight types of 1-deoxyketose, eight types of 6-deoxyketose, 16 types of 6-deoxyaldose and 16 types of 1- and 6-deoxy polyol), which can be produced in the Deoxy-Izumoring shown in FIGS. 1 through 3.

BEST MODE FOR CARRYING OUT THE INVENTION

The present inventors made investigations so as to screen for an epimerase capable of readily epimerizing two deoxyketohexose types as they remained the free deoxy sugars. Consequently, the inventors found that D-ketohexose 3-epimerase, namely D-tagatose 3-epimerase (U.S. Pat. No. 3,333, 969) conventionally known interacts with not only ketohexose but also the corresponding 1-deoxy or 6-deoxyketohexose to obtain such deoxy products resulting from epimerization at position 3. Thus, the inventors established a method for conversion between two D- or L-deoxyketohexose types and a method for producing the converted D- or L-deoxyketose, using the enzyme.

Herein, it has been known that epimerase interacts with various sugars according to Enzyme Nomenclature (USA, Academic Press, Inc. 1992). However, conventionally known epimerase types interact mainly with phosphorylated sugars and sugars bound with UDP, for example ribulose phosphate 3-epimerase (EC 5.1.3.1) and UDP glucose 4-epimerase (EC 5.1.3.2), so these epimerase types could not be used for industrial applications such as production of free, neutral sugars.

As the epimerase interacting with free sugars, alternatively, two epimerase examples interacting with aldose, such as aldose 1-epimerase (EC 5.1.3.3) and cellobiose epimerase (EC 5.1.3.11) or an epimerase interacting with ketose, such as D-ketohexose 3-epimerase has been known. Aldose 1-epimerase catalyzes epimerization between the α- and β anomers of aldose at position 1, while cellobiose epimerase similarly catalyzes the epimerization between the α- and β anomers of cellobiose. D-ketose 3-epimerase catalyzes ketohexose at position 3, but there has never been known whether or not it may interact with deoxy sugars.

The catalytic reaction of L-rhamnose isomerase known as described in accordance with the invention between 6-deoxy L-psicose and 6-deoxy L-altrose has not been known. Furthermore, the reaction from 1-deoxy L-mannitol to produce 1-deoxy L-fructose or the reaction from 1-deoxy D-allitol to produce 1-deoxy D-psicose, via the oxidation with a microorganism with a potency to generate a dehydrogenase, which is known as described in accordance with the invention and belongs to the genus *Enterobacter* has never been known.

Specifically, the inventors found that the enzyme (deoxyketohexose isomerase which can be obtained from a bacterium of the genus *Pseudomonas*, namely D-ketohexose 3-epimerase) catalyzed the reactions between the following compounds:

(i) epimerization reaction from 6-deoxy L-fructose to 6-deoxy L-psicose or the inverse reaction thereof,
(ii) epimerization reaction from 1-deoxy L-tagatose to 1-deoxy L-sorbose or the inverse reaction thereof,
(iii) epimerization reaction from 6-deoxy L-sorbose to 6-deoxy L-tagatose or the inverse reaction thereof,
(iv) epimerization reaction from 1-deoxy L-psicose to 1-deoxy L-fructose or the inverse reaction thereof,
(v) epimerization reaction from 6-deoxy D-sorbose to 6-deoxy D-tagatose or the inverse reaction thereof,
(vi) epimerization reaction from 1-deoxy D-psicose to 1-deoxy D-fructose or the inverse reaction thereof,
(vii) epimerization reaction from 6-deoxy D-fructose to 6-deoxy D-psicose or the inverse reaction thereof,
(viii) epimerization reaction from 1-deoxy D-tagatose to 1-deoxy D-sorbose or the inverse reaction thereof.

Using aldose isomerase, further, D- or L-deoxyketohexose or D- or L-deoxyaldohexose can readily be isomerized to the corresponding D- or L-product, while these sugars remain the free deoxy sugars.

In accordance with the invention, therefore, there is established a method for producing deoxyaldose or deoxyketohexose via conversion from the produced deoxyketohexose to the corresponding deoxyaldose or from the deoxyaldose to the deoxyketohexose.

The enzyme (aldose isomerase) catalyzes reactions between the following compounds:
(a) isomerization reaction of 6-deoxy L-glucose to 6-deoxy L-fructose or the inverse reaction thereof,
(b) isomerization reaction of 6-deoxy L-mannose to 6-deoxy L-fructose or the inverse reaction thereof,
(c) isomerization reaction of 6-deoxy L-allose to 6-deoxy L-psicose or the inverse reaction thereof,
(d) isomerization reaction of 6-deoxy L-altrose to 6-deoxy L-psicose or the inverse reaction thereof,
(e) isomerization reaction of 6-deoxy L-idose to 6-deoxy L-sorbose or the inverse reaction thereof,
(f) isomerization reaction of 6-deoxy L-gulose to 6-deoxy L-sorbose or the inverse reaction thereof,
(g) isomerization reaction of 6-deoxy L-galactose to 6-deoxy L-tagatose or the inverse reaction thereof,
(h) isomerization reaction of 6-deoxy L-talose to 6-deoxy L-tagatose or the inverse reaction thereof,
(i) isomerization reaction of 6-deoxy D-glucose to 6-deoxy D-fructose or the inverse reaction thereof,
(j) isomerization reaction of 6-deoxy D-mannose to 6-deoxy D-fructose or the inverse reaction thereof,
(k) isomerization reaction of 6-deoxy D-allose to 6-deoxy D-psicose or the inverse reaction thereof,
(l) isomerization reaction of 6-deoxy D-altrose to 6-deoxy D-psicose or the inverse reaction thereof,
(m) isomerization reaction of 6-deoxy D-idose to 6-deoxy D-sorbose or the inverse reaction thereof,
(n) isomerization reaction of 6-deoxy D-gulose to 6-deoxy D-sorbose or the inverse reaction thereof,
(o) isomerization reaction of 6-deoxy D-galactose to 6-deoxy D-tagatose or the inverse reaction thereof,
(p) isomerization reaction of 6-deoxy D-talose to 6-deoxy D-tagatose or the inverse reaction thereof.

Using polyol dehydrogenase, additionally, deoxyketohexose and deoxy sugar alcohol can readily be reduced or oxidized to the corresponding deoxy sugar alcohol and deoxyketose, respectively, while these sugars remain the free deoxy sugars.

In accordance with the invention, additionally, a method for producing deoxy sugar alcohol or deoxyketose via conversion from the produced deoxyketohexose to the corresponding deoxy sugar alcohol or from the deoxy sugar alcohol to the deoxyketose has been established. The reduction reaction of deoxyketohexose to deoxy sugar alcohol may also be carried out by a chemical reduction process.

The enzyme (polyol dehydrogenase) catalyzes reactions between the following compounds:
(a) oxidation reaction of 6-deoxy L-glucitol to 6-deoxy L-fructose or the inverse reduction reaction thereof,
(b) oxidation reaction of 6-deoxy L-mannitol to 6-deoxy L-fructose or the inverse reduction reaction thereof,
(c) oxidation reaction of 6-deoxy L-allitol to 6-deoxy L-psicose or the inverse reduction reaction thereof,
(d) oxidation reaction of 6-deoxy L-altritol to 6-deoxy L-psicose or the inverse reduction reaction thereof,
(e) oxidation reaction of 1-deoxy L-talitol to 1-deoxy L-tagatose or the inverse reduction reaction thereof,
(f) reduction reaction of 1-deoxy L-galactitol to 1-deoxy L-tagatose or the inverse oxidation reaction thereof,
(g) oxidation reaction of 1-deoxy L-gulitol to 1-deoxy L-sorbose or the inverse reduction reaction thereof,
(h) oxidation reaction of 1-deoxy L-iditol to 1-deoxy L-sorbose or the inverse reduction reaction thereof,
(i) oxidation reaction of 6-deoxy L-iditol to 6-deoxy L-sorbose or the inverse reduction reaction thereof,
(j) oxidation reaction of 6-deoxy L-gulitol to 6-deoxy L-sorbose or the inverse reduction reaction thereof,
(k) oxidation reaction of 6-deoxy L-galactitol to 6-deoxy L-tagatose or the inverse reduction reaction thereof,
(l) oxidation reaction of 6-deoxy L-talitol to 6-deoxy L-tagatose or the inverse reduction reaction thereof,
(m) oxidation reaction of 1-deoxy L-altritol to 1-deoxy L-psicose or the inverse reduction reaction thereof,
(n) oxidation reaction of 1-deoxy L-allitol to 1-deoxy L-psicose or the inverse reduction reaction thereof,
(o) reduction reaction of 1-deoxy L-mannitol to 1-deoxy L-fructose or the inverse oxidation reaction thereof,
(p) oxidation reaction of 1-deoxy L-glucitol to 1-deoxy L-fructose or the inverse reduction reaction thereof,
(q) oxidation reaction of 6-deoxy D-gulitol to 6-deoxy D-sorbose or the inverse reduction reaction thereof,
(r) oxidation reaction of 6-deoxy D-iditol to 6-deoxy D-sorbose or the inverse reduction reaction thereof,
(s) oxidation reaction of 6-deoxy D-galactitol to 6-deoxy L-tagatose or the inverse reduction reaction thereof,
(t) oxidation reaction of 6-deoxy D-talitol to 6-deoxy D-tagatose or the inverse reduction reaction thereof,
(u) oxidation reaction of 1-deoxy D-allitol to 1-deoxy D-psicose or the inverse reduction reaction thereof,
(v) reduction reaction of 1-deoxy D-glucitol to 1-deoxy D-fructose or the inverse oxidation reaction thereof, (w) oxidation reaction of 1-deoxy D-mannitol to 1-deoxy D-fructose or the inverse reduction reaction thereof,
(x) oxidation reaction of 6-deoxy D-mannitol to 6-deoxy D-fructose or the inverse reduction reaction thereof,
(y) oxidation reaction of 6-deoxy D-glucitol to 6-deoxy D-fructose or the inverse reduction reaction thereof,
(z) oxidation reaction of 6-deoxy D-allitol to 6-deoxy D-psicose or the inverse reduction reaction thereof,
(A) oxidation reaction of 6-deoxy D-allitol to 6-deoxy D-psicose or the inverse reduction reaction thereof,
(B) oxidation reaction of 1-deoxy D-talitol to 1-deoxy D-tagatose or the inverse reduction reaction thereof,
(C) oxidation reaction of 1-deoxy D-galactitol to 1-deoxy D-tagatose or the inverse reduction reaction thereof,
(D) reduction reaction of 1-deoxy D-iditol to 1-deoxy D-sorbose or the inverse oxidation reaction thereof,
(E) oxidation reaction of 1-deoxy D-gulitol to 1-deoxy D-sorbose or the inverse reduction reaction thereof.

Using aldose reductase or via a chemical reduction reaction, additionally, deoxyaldohexose is readily reduced to deoxy sugar alcohol while the sugar remains the free deoxy sugar.

In accordance with the invention, additionally, a method for producing deoxy sugar alcohol via conversion of deoxyaldohexose to the corresponding deoxy sugar alcohol is provided.

The enzyme (aldose reductase) or a chemical reduction process catalyzes the reactions between the following compounds:
(a) reduction reaction of 6-deoxy L-glucose to 6-deoxy L-glucitol,
(b) reduction reaction of 6-deoxy L-mannose to 6-deoxy L-mannitol,
(c) reduction reaction of 6-deoxy L-allose to 6-deoxy L-allitol,
(d) reduction reaction of 6-deoxy L-altrose to 6-deoxy L-altritol,
(e) reduction reaction of 6-deoxy L-idose to 6-deoxy L-iditol,
(f) reduction reaction of 6-deoxy L-gulose to 6-deoxy L-gulitol,
(g) reduction reaction of 6-deoxy L-galactose to 6-deoxy L-galactitol,
(h) reduction reaction of 6-deoxy L-talose to 6-deoxy L-talitol,
(i) reduction reaction of 6-deoxy D-altrose to 6-deoxy D-altritol,
(j) reduction reaction of 6-deoxy D-allose to 6-deoxy D-allitol,
(k) reduction reaction of 6-deoxy D-glucose to 6-deoxy D-glucitol,
(l) reduction reaction of 6-deoxy D-mannose to 6-deoxy D-mannitol,
(m) reduction reaction of 6-deoxy D-talose to 6-deoxy D-talitol,
(n) reduction reaction of 6-deoxy D-galactose to 6-deoxy D-galactitol,
(o) reduction reaction of 6-deoxy D-idose to 6-deoxy D-iditol, and
(p) reduction reaction of 6-deoxy D-gulose to 6-deoxy D-gulitol.

In accordance with the invention, there are established and provided a method for producing any of 1- or 6-D-deoxyhexose or 1- or 6-L-deoxyhexose by using a combination of the four enzymes described above and the chemical reduction process from any of the 1- or 6-D-deoxyhexose or 1- or 6-L-deoxyhexose as a raw material.

The method for producing deoxyhexose in accordance with the invention is based on a novel finding that D-ketohexose 3-epimerase has an activity of epimerizing deoxyketohexose at position 3 to generate the corresponding deoxyketohexose. According to the method, there are provided approaches for producing all deoxyhexose types by systematically using aldose isomerase, polyol dehydrogenase, aldose reductase and chemical reduction processes.

As the D-ketose 3-epimerase for use, D-ketose 3-epimerase epimerizing D-deoxyketohexose at position 3 is selected. D-Ketose 3-epimerase described in U.S. Pat. No. 3,333,969 is preferable owing to the high reaction activity. Additionally, any aldose isomerase catalyzing the isomerization between deoxyketohexose and deoxyaldohexose is satisfactory, but L-rhamnose isomerase described in WO2004/063369 is particularly preferable. Additionally, the reduction reaction of deoxyketohexose and deoxyaldohexose can be carried out by contact reduction with Raney nickel as a catalyst, and with aldose reductase and polyol dehydrogenase. Additionally, the oxidation of sugar alcohol can be done with polyol dehydrogenase and the like.

The main physico-chemical properties of D-tagatose 3-epimerase for use in accordance with the invention are described in the specification of U.S. Pat. No. 3,333,969, and the properties thereof on deoxy sugars are described below.
(1) Action and substrate specificity: epimerizing D- or L- or 1- or 6-deoxyketohexose at position 3 to generate the corresponding D- or L- or 1- or 6-deoxyketohexose.
(2) Optimal pH and pH stability: optimal pH at pH 7 to 10, with stability at pH 5 to 10.
(3) Optimal temperature and thermostability: optimal temperature around 60° C., with stability at 50° C. or less.

The D-tagatose 3-epimerase, namely D-ketohexose 3-epimerase of the invention can generally be prepared by the method disclosed in the specification of U.S. Pat. No. 3,333,969 using *Pseudomonas cichorii* ST-24 (FERM BP-2736) and variant species thereof.

Specifically, *Pseudomonas cichorii* ST-24 (FERM BP-2736) is cultured in a nutritious culture medium containing for example a carbon source, a nitrogen source, an inorganic salt, and vitamin for about one to 5 days, preferably under aerobic conditions under aerated agitation in a liquid culture medium. From the resulting bacterial cell or the resulting culture such as culture supernatant is extracted D-tagatose 3-epimerase. Generally, the culture can be utilized as crude D-ketohexose 3-epimerase. If necessary, the culture may be purified partially by known methods such as filtration, centrifugation, desalting out, dialysis, concentration and freeze-drying for use. Furthermore, the resulting culture may be highly purified by a combination of adsorption onto and elution from ion exchangers, gel filtration, isoelectric fractionation, electrophoresis, high-performance liquid chromatography, affinity chromatography, and adsorption onto and elution from monoclonal antibodies. The resulting culture may also be used. In such manner, D-tagatose 3-epimerase purified by electrophoresis on polyacrylamide gel to a single peak epimerizes the OH group at position 3 in D-ketohexose. Surprisingly, further, it was revealed that the enzyme exerted the epimerase activity even for 1- or 6-D-deoxyhexose, or 1- or 6-L-deoxyhexose.

For the conversion reaction of the invention, namely the conversion reaction of one or more ketoses selected from D- or L-deoxyketohexose types to epimerize the position 3 of the ketose to generate the corresponding D- or L-deoxyketohexose, the D-deoxyketohexose 3-epimerase is immobilized by a known method advantageously for repeated use for the reaction or for use in continuous reaction.

The conversion reaction is generally done under the following conditions. The substrate concentration is 1 to 60 w/v %, preferably about 5 to 50 w/v %; the reaction temperature is 10 to 70° C., preferably about 30 to 60° C.; the reaction pH is pH 5 to 10, preferably about pH 7 to 10; the enzyme activity is one unit or more per gram substrate, and is preferably selected from a range of 50 to 5,000 units. The reaction time can appropriately be selected. In terms of economy, a range of 5 to 50 hours is generally selected for a batch reaction.

The enzyme activity unit described above is the enzyme unit for tagatose 3-epimerase activity and is assayed as follows.

Specifically, a solution (or a suspension) containing 100 µl of 50 mM Tris-HCl buffer (pH 7.5), 50 µl of 40 mM D-tagatose, and 50 µl of the enzyme solution was incubated at 30° C. for 60 minutes; and the product D-sorbose was assayed by HPLC. One unit of the enzyme activity corresponds to an enzyme amount epimerizing 1 µmol of D-tagatose per one minute to generate D-sorbose.

The reaction solution resulting from the conversion in such manner contains the raw material deoxyketose and freshly generated deoxyketose (the epimer of the raw material), and if necessary, the concentrate solution of the reaction solution is fractionated by column chromatography using a strongly acidic cation exchange resin of an alkali metal type or an alkali earth metal type to separate and purify the freshly generated deoxyketose from the raw material deoxyketose; a fraction highly containing the freshly generated deoxyketose is concentrated to obtain a syrup-like product. In case that crystallization is possible, additionally, the deoxyketose is crystallized to obtain a crystalline product, advantageously. Additionally, the separated raw material deoxyketose may also be recycled as the raw material for the conversion reaction.

The species of the enzyme catalyzing the isomerization for use in accordance with the invention, namely the species of the aldose isomerase catalyzing the isomerization between 1- or 6-deoxyketohexose and 1- or 6-deoxyaldohexose includes but is not specifically limited to L-rhamnose isomerase described in WO 2004/063369 or JP-A-2006-153591.

The L-rhamnose isomerase described in WO 2004/063369 is an isomerizing enzyme known as an enzyme catalyzing the isomerization from L-rhamnose obtained from the liquid culture of "*Pseudomonas stutzeri* LL172" to 6-deoxy L-fructose and the isomerization of 6-deoxy L-fructose to L-rhamnose. Additionally, the bacterial strain *Pseudomonas stutzeri* LL172 is internationally deposited at the Patent Organism Depositary Center, the Incorporated Administrative Agency, the Advanced Industrial Science and Technology, Japan (Chuo 6$^{th}$, 1-1-1, Higashi, Tsukuba, Ibaraki, Nippon) on Jan. 6, 2004 (IPOD FERM BP-08593).

The properties of the enzyme are as follows.
(I) Action pH and Optimal pH
The action pH is 7.0 to 10.0, while the optimal pH is 9.0.
(II) pH Stability
In case that the enzyme is retained at various pHs and 4° C. for one hour, the enzyme is stable within a range of pH 6.0 to 11.0.
(III) Action Temperature and Optimal Temperature
The action temperature is 40 to 65° C., while the optimal temperature is 60° C.
(IV) Temperature Stability
Stable at 40° C. for 10 minutes; at 50° C. for 10 minutes, 90% or more of the enzyme remains.

(V) Influence of Chelating Agents
EDTA and EGTA as chelating agents when concurrently exist with the enzyme during the assay of the activity, the activity is hardly inhibited.
(VI) Influence of Metal Ions
1 mM cobalt ion inhibits about 30% of the enzyme.
(VII) Molecular weight by SDS-PAGE
Molecular weight of about 43,000.

The polyol dehydrogenase (polyol dehydrogenase) for use in accordance with the invention is an enzyme catalyzing the reaction between 1- or 6- or D- or L-deoxyketohexose and sugar alcohol of the corresponding hexose and can be selected from known such enzymes.

The aldose reductase for use in accordance with the invention is an enzyme catalyzing the redox reaction between 6-deoxy D- or L-aldohexose and the corresponding sugar alcohol. As such, known enzymes can be used.

At the step of reducing 6-deoxy D- or L-aldohexose or 1- or 6-deoxy or D- or L-ketohexose to produce the corresponding sugar alcohol, a chemical reduction reaction may also be used.

A reduction reaction of organic chemistry can be done by hydrogenation (contact reduction) in the presence of a catalyst containing a metal selected from elements of the group 8 in the periodic table, such as nickel, ruthenium, platinum and palladium.

The intended deoxyhexose can be produced from any deoxyhexose via a combination of the reactions described above. L-Fucose or L-rhamnose naturally occurring can be used as the starting raw material, most inexpensively.

Because it is expected that the deoxyhexose produced above is applicable to research works about metabolism and biological signals, in particular, the deoxyhexose is preferable as chemical products, pharmaceutical products, intermediate materials, and research reagents. The deoxyhexose can be used advantageously for giving sweetness to orally ingestible materials and improving the taste thereof, including for example fermenting carbon sources, drinks and foods, feeds, baits, toothpastes, oral fragrance, sublingual tablets, and oral drugs. Additionally, the deoxyhexose can be utilized as an intermediate for pharmaceutical materials.

The invention is now described in detail in some Examples. However, the invention is never limited by these Examples.

Example 1

Production of 6-deoxy L-psicose from L-rhamnose

Using L-rhamnose isomerase, L-rhamnose is isomerized to L-rhamnulose (6-deoxy L-fructose), which is then epimerized with D-tagatose 3-epimerase to produce 6-deoxy L-psicose.

[Preparation of D-Tagatose 3-Epimerase]
The gene of D-tagatose 3-epimerase derived from *Pseudomonas cichorii* strain ST-24 (FERM BP-2736) was transfected into *Escherichia coli*, to culture a recombinant strain of *Escherichia coli* to obtain D-tagatose 3-epimerase. After culturing the recombinant strain of *Escherichia coli* at a mass scale, the resulting bacterial cells were frozen and stored at −80° C. The bacterial cells frozen under storage were left to stand in ice water for 30 minutes, to thaw the surface thereof. Then, the bacterial cells were suspended using 50 mM Tris-HCl buffer, pH 8.0. Using an ultrasonic homogenizer SONIFIER 250 (Branson Co., Ltd.), 200 ml of the suspension was disrupted for 6 minutes, while the suspension was kept at 4° C. The procedure was repeated twice. The solution was centrifuged at 4° C. and 11,500 rpm for 20 minutes, and the resulting supernatant was defined as a crude enzyme solution. Under agitation with a magnetic stirrer, ground polyethylene glycol #6000 was gradually added at 5% by weight to the crude enzyme solution in an ice-water bath, for subsequent agitation for another one hour after addition. The resulting mixture was centrifuged at 4° C. and 11,500 rpm for one hour to recover the supernatant. Polyethylene glycol #6000 was again added at 25% by weight to the supernatant by the same procedure, for agitation for another one hour after addition. This was centrifuged at 4° C. and 11,500 rpm for one hour to recover the precipitate. A small amount (about 5-fold the weight of the bacterial cells) of 50 mM Tris-HCl buffer, pH 8.0 was added to the precipitate, for suspension (the resulting suspension was defined as partially purified D-tagatose 3-epimerase).

[Assay of the Activity of D-Tagatose 3-Epimerase]

The activity of D-tagatose 3-epimerase was assayed using D-tagatose as a substrate for reaction. The amount of the generated D-sorbose was determined by HPLC analysis. The enzyme reaction progressed at the composition shown in Table 1, at 30° C. for 10, 20 and 30 minutes; and the reaction was terminated by heating in hot water for 2 minutes. The generated D-sorbose was determined to define the amount of D-tagatose 3-epimerase generating 1 μmol D-sorbose per one minute as 1 U (unit).

TABLE 1

Reaction composition for assaying the activity of D-tagatose 3-epimease

| | |
|---|---|
| 50 mM Tris-HCl buffer (pH 8.0) + DTE enzyme solution | 100 μl |
| 200 mM D-tagatose | 100 μl |
| | 200 μl in total |

The properties of the resulting partially purified D-tagatose 3-epimerase are as follows.

(1) As to the action and the substrate specificity, the D-tagatose 3-epimerase epimerizes 1- or 6-deoxy or D- or L-ketohexose at position 3 to generate the corresponding f- or 6-deoxy or D- or L-ketohexose.

(2) Optimal pH and pH stability: optimal pH around pH 7 to 10 with stability at pH 5 to 10.

(3) Optimal temperature and thermostability: optimal temperature around 60° C. with stability at 50° C. or less.

[Immobilization of D-Tagatose 3-Epimerase]

The immobilization of D-tagatose 3-epimerase was done, using Chitopearl BCW 2510. First, the Chitopearl resin was washed with 50 mM Tris-HCl buffer, pH 8.0 and then left to stand overnight in a refrigerator for equilibrium. Then, the partially purified D-tagatose 3-epimerase of 200 U was mixed with 1 mL (corresponding to about 1 g of the wet weight) of the Chitopearl resin, and left to stand in a refrigerator for 2 days under eventual agitation, to immobilize the enzyme. The Chitopearl was washed with the same buffer, and the resulting Chitopearl was defined as the immobilized enzyme.

In the following Examples, the immobilized enzyme was used for carrying out the epimerization of deoxyketohexose.

[Production of L-Rhamnose Isomerase]

[Properties of L-Rhamnose Isomerase]

The gene of L-rhamnose isomerase derived from *Pseudomonas stutzeri* LL172 (IPOD FERM BP-08593) was transfected into *Escherichia coli*, to culture a recombinant strain of *Escherichia coli* to obtain D-rhamnose isomerase.

After culturing the recombinant strain of *Escherichia coli* at amass scale, the resulting bacterial cells were frozen and stored at −80° C. The bacterial cells frozen under storage were left to stand in ice water for 30 minutes, to thaw the surface thereof. Then, the bacterial cells were suspended using 10 mM Tris-HCl buffer, pH 9.0. Using an ultrasonic homogenizer SONIFIER 250 (Branson Co., Ltd.), 200 ml of the suspension was disrupted for 6 minutes, while the suspension was kept at 4° C. The procedure was repeated twice. The solution was centrifuged at 4° C. and 11,500 rpm for 20 minutes, and the resulting supernatant was defined as a crude enzyme solution. Under agitation with a magnetic stirrer, ground polyethylene glycol #6000 was gradually added at 5% by weight to the crude enzyme solution in an ice-water bath, for subsequent agitation for another one hour after addition. The resulting mixture was centrifuged at 4° C. and 11,500 rpm for one hour to recover the supernatant. Polyethylene glycol #6000 was again added at 25% by weight to the supernatant by the same procedure, for agitation for another one hour after addition. A small amount (about 5-fold the weight of the bacterial cells) of 10 mM Tris-HCl buffer, pH 9.0 was added to the precipitate, for suspension (the resulting suspension was defined as partially purified L-rhamnose isomerase).

[Assay of the Activity of L-Rhamnose Isomerase]

The activity of L-rhamnose isomerase was assayed using L-rhamnose as a substrate for reaction. The amount of the generated 6-deoxy L-fructose was determined by the cysteine carbazole method. The enzyme reaction progressed at the composition shown in Table 2 at 30° C. for 10 minutes; and the reaction was terminated by addition of 50 μl of 10% TCA (trichloroacetic acid). As shown in table 3, the cysteine carbazole method comprised sequentially adding 100 μl of 1.5% cysteine solution, and 3 ml of 70% sulfuric acid to 0.5 ml of the sample after the enzyme reaction; and the resulting mixture was left to stand in water under agitation, to which 100 μl of 0.12% carbazole solution was added for reaction under agitation at 35° C. for 20 minutes. After completion of the reaction, the absorbance at 540 nm was measured with an ultraviolet visible spectrophotometer V530 (Jasco Corporation). Herein, the enzyme amount generating 1 μmol 6-deoxy L-fructose per one minute was defined as 1 U.

TABLE 2

Reaction composition for assaying the activity of L-rhamnose isomerase and reaction conditions therefor

| | |
|---|---|
| 10 mM Tris-HCl buffer (pH 9.0) | 350 μl |
| LRI enzyme solution | 50 μl |
| 50 mM L-rhamnose | 50 μl |
| ↓ | |
| Incubation at 30° C. for 10 minutes | |
| 10% Trichloroacetic acid | 50 μl |
| | in total of 500 μl |

TABLE 3

Cysteine carbazole method

| | |
|---|---|
| Sample 500 μl | |
| Cysteine solution | 100 μl |
| 70% sulfuric acid | 3,000 μl |
| Carbazole solution | 100 μl |
| Incubation at 35° C. for 20 minutes | |
| Measuring absorbance at 540 nm. | |

The properties of the partially purified L-rhamnose isomerase were as follows.

(1) The enzyme catalyzes the isomerization between L-rhamnose and 6-deoxy L-fructose.
(2) The enzyme catalyzes the reaction between 6-deoxy L-psicose and 6-deoxy L-altrose.
(3) The enzyme is thermostable at 40° C. or less, with the optimal temperature of 60° C. Stability at pH 7.0 to 9.0, with the optimal pH at pH 9.0.

[Immobilization of L-Rhamnose Isomerase]

For immobilizing L-rhamnose isomerase, then, Chitopearl BCW 2510 was used. First, the Chitopearl resin was washed with 10 mM Tris-HCl buffer, pH 9.0 and then left to stand overnight in a refrigerator for equilibrium. Then, the partially purified L-rhamnose isomerase of 50 U was mixed with 1 mL (corresponding to about 1 g of the wet weight) of the Chitopearl resin, and left to stand in a refrigerator for 2 days under eventual agitation, to immobilize the enzyme. The Chitopearl was washed with the same buffer, and the resulting Chitopearl was defined as the immobilized enzyme.

[Isomerization of L-Rhamnose with the Immobilized L-Rhamnose Isomerase]

L-Rhamnose was prepared to Brix 30%; 250 ml of the resulting solution was transferred into a 500-ml Erlenmeyer flask. Under agitation under conditions of 42° C. and 120 rpm, 100 ml (corresponding to 5000 U) of the immobilized L-rhamnose isomerase and 5 mL (at a final concentration of about 10 mM) of 1M Tris-HCl buffer, pH 9.0 were added to the flask, for reaction under agitation under conditions of 42° C. and 120 rpm. Every one hour, 10 µl of the reaction solution was collected, diluted with 290 µl of water (30-fold dilution) and heated with hot water for 2 minutes to inactivate the enzyme. Subsequently, the reaction mixture was centrifuged at 12,000 rpm for 5 minutes, to recover the supernatant. A small volume of the desalting resin (a mixture of IRA411: SKIB=2:1, which was dried) was added to the supernatant, for inverse mixing. One hour later, the solution was filtered through a 0.45-µm filter for HPLC. The equilibrium ratio of the reaction was L-rhamnose of 55% and 6-deoxy L-fructose of 45% (FIG. 9). Additionally, the time required until the reaction reached equilibrium was about 10 hours. The results of the HPLC analysis of the solution at the equilibrium are shown (FIG. 10).

[Isomerization (Epimerization) of 6-Deoxy L-Fructose with D-Tagatose 3-Epimerase]

A mix sugar solution of L-rhamnose and 6-deoxy L-fructose was prepared to Brix 30% and 250 mL, which was then transferred into a 500-mL Erlenmeyer flask. 25 mL (corresponding to 5,000 U) of the immobilized D-tagatose 3-epimerase and 40 mL of 1M Tris-HCl buffer, pH 8.0 (to a final concentration of about 50 mM) were placed in the flask, for reaction under conditions of 42° C. and 120 rpm under agitation.

10 µl of the reaction solution was taken out every one hour, and then diluted with 290 µl of water (30-fold dilution). After heating in hot water for 2 minutes, the heated solution was centrifuged at 12,000 rpm for 5 minutes. The resulting supernatant is transferred to another Eppendorf tube. A small volume of a desalting resin (a mixture of IRA411: SKIB=2:1, which was dried) was added to the tube for inversion mixing. One hour later, the solution was filtered through a 0.45-µm filter, for HPLC. The equilibrium ratio was L-rhamnose at 55%, 6-deoxy L-fructose at 36% and 6-deoxy L-psicose at 9% (FIG. 11). Additionally, the time required for the reaction to reach the equilibrium was about 96 hours. The results of the HPLC analysis of the solution at the equilibrium state are shown (FIG. 12).

[Separation of 6-Deoxy L-Psicose]

After the isomerization, the immobilized enzyme was removed by filtration. Desalting resins (IRA411 (40 ml) and SKIB (20 ml)) were mixed together and packed in an open column, through which the sugar solution was passed in small portions. After desalting, the resulting eluate was concentrated with a rotary evaporator. Subsequently, the resulting concentrate was filtered through a 0.22-µm filter, and the resulting filtrate was prepared to Brix 30%. Using a one-pass mode chromatographic apparatus, 6-deoxy L-psicose was separated (Table 4). After separation, the solutions in the individual tanks were analyzed by HPLC, and the results are shown in FIG. 13. The calculated yield from L-rhamnose was about 8%. FIG. 13 shows separation graphs with the one-pass column; tank A contains almost no sugar; and L-rhamnose and L-rhamnulose in tank B, a small amount of 6-deoxy L-fructose in tank C and 6-deoxy L-fructose in tank D are mainly eluted and separated at purity. In other words, the peaks in tank A, tank B, tank C and tank D individually correspond to extremely small amounts of L-rhamnose and L-rhamnulose, L-rhamnose and L-rhamnulose, small amounts of 6-deoxy L-fructose and 6-deoxy L-fructose, respectively.

TABLE 4

Method for separating 6-deoxy L-psicose by one-pass chromatography

| | |
|---|---|
| Sample volume | 300 mL |
| Flow rate | 60 mL/min |
| Equilibrium | 90 min |
| Tank A | 30 min |
| Tank B | 70 min |
| Tank C | 20 min |
| Tank D | 90 min |

[Structural Analysis of 6-Deoxy L-Psicose]

6-Deoxy L-psicose of 20 to 30 mg (for $^{13}$C-NMR) or of 10 to 15 mg (for $^1$H-NMR) was placed in an Eppendorf tube, to which 600 µL of heavy water was added. The opening of the tube was covered with a para-film, through which punctures were made with a toothpick at three positions. Then, the tube was frozen in a deep freezer. The resulting tubes were freeze-dried, to which 600 µL of heavy water was added again, for freeze-drying. After drying, 600 µL of heavy water preliminarily prepared to 1% of a TSP (3-methylsilyl propionic 2, 2, 3, 3-d4 acid) concentration was added to dissolve the freeze-dried material. The resulting solutions were placed in glass tubes for NMR and subjected to measurement. As reference materials, L-rhamnose and D-psicose were analyzed. The individual $^{13}$C-NMR shifts were assigned, while the structures of the tautomers are shown in Tables 5, 6 and 7. The black columns in the tables show the absence of any shift. These indicate that 6-deoxy-L-psicose was generated and that the equilibrium ratio between 6-deoxy-L-fructose and 6-deoxy-L-psicose was 80:20.

TABLE 5

Chemical shifts of L-rhamnose on $^{13}$C NMR and tautomer types

| | C1 | C2 | C3 | C4 | C5 | C6 |
|---|---|---|---|---|---|---|
| α-Pyranose | 96.32 | 74.16 | 73.65 | 72.80 | 74.67 | 19.58 |
| β-Pyranose | 96.81 | 74.85 | 75.03 | 71.16 | 75.59 | 19.63 |
| α-Franose | | | | | | |
| β-Franose | | | | | | |

TABLE 6

Chemical shifts of D-psicose on $^{13}$C NMR and tautomer types

|  | C1 | C2 | C3 | C4 | C5 | C6 |
|---|---|---|---|---|---|---|
| α-Pyranose | 65.97 | 100.48 | 67.92 | 74.53 | 68.69 | 60.82 |
| β-Pyranose | 66.87 | 101.22 | 71.82 | 73.01 | 73.20 | 67.00 |
| α-Franose | 66.14 | 106.06 | 68.40 | 73.20 | 85.56 | 64.20 |
| β-Franose | 65.27 | 108.40 | 77.57 | 73.83 | 85.56 | 65.62 |

TABLE 7

Chemical shifts of 6-deoxy L-psicose on $^{13}$C NMR and tautomer types

|  | C1 | C2 | C3 | C4 | C5 | C6 |
|---|---|---|---|---|---|---|
| α-Pyranose |  |  |  |  |  |  |
| β-Pyranose |  |  |  |  |  |  |
| α-Franose | 65.38 | 105.76 | 78.02 | 78.84 | 73.17 | 20.53 |
| β-Franose | 66.35 | 108.06 | 81.34 | 80.78 | 73.17 | 22.16 |

Example 2

Generation of 6-Deoxy L-Altrose from 6-Deoxy L-Psicose

Using L-rhamnose isomerase for isomerization of a substrate 6-deoxy L-psicose obtained in Example 1, 6-deoxy L-altrose was generated.

L-Rhamnose isomerase was purified in the same manner as in Example 1.

[Isomerization of 6-Deoxy L-Psicose in a Bioreactor Using Immobilized L-Rhamnose Isomerase]

150 mL (corresponding to 7,500 U) of the immobilized L-rhamnose isomerase was filled in a column with a jacket. While water at 42° C. flowed in the jacket, the column was kept warm. 6-Deoxy L-psicose prepared to Brix 2% flowed at a rate of 0.5 mL/min upwardly from the bottom to the top through the column. Herein, 1M. Tris-HCl buffer, pH 9.0 was preliminarily added to the substrate to a final concentration of about 10 mM. The equilibrium ratio was 6-deoxy-L-psicose of 94% and 6-deoxy L-altrose of 6%. The results of the HPLC analysis of the solution at the equilibrium state are shown (FIG. 14). The equilibrium ratio between 6-deoxy L-psicose and 6-deoxy L-altrose was 94:6.

[Separation of 6-Deoxy L-Altrose]

After the isomerization, the immobilized enzyme was removed by filtration. Desalting resins (IRA411 (40 ml) and SKIB (20 ml)) were mixed together and packed in an open column, through which the sugar solution was passed in small portions. After desalting, the resulting eluate was concentrated with a rotary evaporator. Subsequently, the resulting concentrate was filtered through a 0.22-μm filter, and the resulting filtrate was prepared to Brix 30%. Using a one-pass mode chromatographic apparatus, 6-deoxy L-altrose was separated. The yield from L-rhamnose was about 0.48%.

[Structural Analysis of 6-Deoxy L-Altrose]

6-Deoxy L-altrose of 20 to 30 mg (for $^{13}$C-NMR) or of 10 to 15 mg (for $^1$H-NMR) was placed in individual Eppendorf tubes, to which 600 μL of heavy water was added and freeze-dried, to which 600 μL of heavy water was added again, for freeze-drying. After drying, 600 μL of heavy water preliminarily prepared to 1% of a TSP (3-methylsilyl propionic 2,2,3,3-d4 acid) concentration was added to dissolve the freeze-dried material. The resulting solutions were placed in glass tubes for NMR and subjected to measurement. As a reference material, D-altrose was analyzed. It was assumed that the tautomers of 6-deoxy L-altrose would be four types of α- and β-pyranose and α- and β-franose. The individual $^{13}$C-NMR shifts were assigned, while the structures of the tautomers are shown in Tables 8 and 9. These indicate that 6-deoxy-L-altrose was generated.

TABLE 8

Chemical shifts of D-altrose on $^{13}$C NMR and tautomer types

|  | C1 | C2 | C3 | C4 | C5 | C6 |
|---|---|---|---|---|---|---|
| α-Pyranose | 98.17 | 73.17 | 73.04 | 68.03 | 74.09 | 63.41 |
| β-Pyranose | 93.30 | 79.42 | 73.36 | 67.09 | 76.91 | 64.41 |
| α-Franose | 104.13 | 84.24 | 78.74 | 86.10 | 74.49 | 65.19 |
| β-Franose | 96.56 | 79.42 | 77.94 | 83.93 | 75.45 | 65.23 |

TABLE 9

Chemical shifts of D-deoxy L-altrose on $^{13}$C NMR and tautomer types

|  | C1 | C2 | C3 | C4 | C5 | C6 |
|---|---|---|---|---|---|---|
| α-Pyranose | 97.80 | 72.25 | 71.21 | 70.51 | 73.16 | 18.81 |
| β-Pyranose | 94.46 | 72.74 | 72.54 | 69.76 | 73.87 | 20.67 |
| α-Franose | 103.80 | 87.28 | 78.29 | 89.19 | 73.40 | 20.12 |
| β-Franose | 95.92 | 79.54 | 77.12 | 84.39 | 73.72 | 20.24 |

Example 3

Production of 6-Deoxy L-Mannitol Via Reduction of L-Rhamnose (6-Deoxy L-Mannose)

Via a chemical reaction, 6-deoxy L-mannitol was produced from 6-deoxy L-mannose.

[Reduction with Raney-Nickel as a Catalyst]

100 g of aqueous 20% NaOH solution was added to 10 g of 50% Raney-nickel (manufactured by Wako Pure Chemical Industry Co., Ltd.). After addition, heating was done at 90° C. for one hour. After the termination of gas generation was confirmed, the catalyst was washed with distilled water by decantation. Washing was continued until the wash solution reached pH 9.2.

After 24 g of the Raney-nickel obtained by the method described above was added to 300 g of an aqueous solution containing 100 g of 6-deoxy L-mannose and the resulting mixture was then placed in a 1 L-glass autoclave equipped with an agitator and a thermometer, water was additionally added to adjust the total reaction volume to 600 g. So as to adjust the reaction solution to pH 7, then, calcium carbonate was added. The reaction progressed while the temperature was kept at 50° C.; the hydrogen pressure, at 12 kg/cm$^2$ (gauge pressure); the agitation velocity, at 700 rpm. The reaction solution was analyzed by HPLC. Consequently, up to 1% of the 6-deoxy L-mannose was reduced during the 8-hour reaction, to enable the production of 6-deoxy L-mannitol.

Example 4

Production of 1-Deoxy L-Fructose Via Oxidation of 1-Deoxy L-Mannitol

Via a microbial reaction with *Enterobacter aerogenes* IK7, 1-deoxy L-mannitol prepared in Example 3 was oxidized to produce 1-deoxy L-fructose.

The bacterial strain was isolated in soil in a river running in Miki-cho, Kida-gun, Kagawa-ken. 16SrRNA extracted from the bacterial strain was sequenced, and the sequence thereof was compared with those of plural existing 16SrRNAs obtained from other microorganisms. The data was 99-% identical to the sequence from *Enterobacter aerogenes*. Based on the evidence and other physiological features described below, it was concluded that the bacterial strain corresponded to *Enterobacter aerogenes*. Herein, the nucleotide sequence of DNA fragments can be determined by known methods, for example the Sanger method (Molecular Cloning, Vol. 2, pp. 13.3, 1989), PCR-based methods and the like. Generally, the reaction therefor is done for example with GenomeLab DTCS Quick Start Kit (a sequencing kit containing fluorescent dideoxy terminator) by Beckman Coulter Corporation, to determine the nucleotide sequence with an automatic sequencer (for example, CEQ8,000) manufactured by Beckman Coulter Corporation.

[Physiological Features]
Gram staining negative
Motility none
Growth temperature 37° C. (possibly growing at 4 up to 40° C., preferably at 37° C.)
Oxygen demand facultative anaerobic but preferably in an oxygen-supplying mode
Morphology rod
Urea decomposition negative
Ornithine decarboxylate positive
Colonies at growing state circular, protrusion, dry, transparent, cream and white
[Culture Medium]
(Culturing at for example pH 5 to 9, preferably at pH 6 to 8.5. Culturing is performed under aerobic conditions such as shaking or aerated agitation)
1. TSB (Tryptic Soy Broth) Culture Medium at 1 to 2%
   TSB: Becton, Dickinson Co., Ltd.
2. Meat Extract Culture Medium
[meat extracts (Wako Pure Chemical Industry Co., Ltd.) at 0.5%, polypeptone (Wako Pure Chemical Industry Co., Ltd.) at 0.5%, sodium chloride (Wako Pure Chemical Industry Co., Ltd.) at 0.5%, pH 7.0]
3. Yeast Extract Culture Medium
[yeast extracts (Wako Pure Chemical Industry Co., Ltd.) at 0.5%, polypeptone (Wako Pure Chemical Industry Co., Ltd.) at 0.5%, sodium chloride at 0.5%, pH 7.0]
In case of an agar culture medium, agar is added to a final concentration of 2%.

The strain IK7 isolated by the inventors is a novel microorganism and was domestically deposited at the Patent Organism Depositary, the Incorporated Administrative Agency, the National Institute of Technology and Evaluation, in 2-5-8, Kazusa-kamatari, Kisarazu-shi, Chiba, Japan on Oct. 19, 2006, as the accession No. (NITE P-L-fucose). Subsequently, the original deposit (NITE P-271) was requested for transfer to the international depositary to which the original deposition was made, so that the international depositary issued an accession certificate (NITE BP-271) for the original deposit on Mar. 22, 2007.

[Preparation of Bacterial Cell carrying Sugar Alcohol Dehydrogenase]

*Enterobacter aerogenes* IK7 was inoculated in a sterilized culture broth (2% TSB (trypsin soy broth: Becton Dickinson Company) supplemented with 1% D-mannitol as a carbon source), for shaking culture at 37° C. and 120 rpm for 24 hours, to prepare a bacterial cell abundantly carrying a sugar alcohol dehydrogenase.

After completion of culturing, the culture was centrifuged. The recovered bacterial cell was washed twice with an appropriate volume of primary exchange water, and was then suspended in an appropriate volume of 50 mM Tris-HCl buffer (pH 9.0). (The resulting suspension was defined as a bacterial cell solution containing the sugar alcohol dehydrogenase.)

Using the prepared bacterial cell solution with the sugar alcohol dehydrogenase activity, 1-deoxy-L-fructose was prepared from 1-deoxy L-mannitol.

In an L-character tube (a volume of 30 ml), the bacterial solution containing 50 mM Tris-HCl buffer (pH 9.0) and the sugar alcohol dehydrogenase [to a final bacterial cell concentration of $OD_{600}=20$ ($OD_{600}$ means the optical density at the absorbance at 600 nm)] and 1-deoxy L-mannitol (to a final concentration of 10%) were placed to adjust $OD_{600}$ to 50; the resulting solution was kept warm at 37° C., for gentle shaking to allow for aerobic conditions. The product was verified by centrifuging the resulting reaction solution to remove insoluble matters and analyzing the resulting supernatant by high-performance liquid chromatography.

In 18 hours, 1-deoxy-L-fructose was obtained at maximum, which corresponded to about 80% of 1-deoxy L-mannitol.

Example 5

Production of 1-Deoxy L-Psicose Via Epimerization with D-Tagatose 3-Epimerase from 1-Deoxy L-Fructose Using D-tagatose 3-epimerase, 1-deoxy L-psicose was produced from 1-deoxy L-fructose prepared in Example 4.

D-Tagatose 3-epimerase was prepared by the same method as in Example 1.

Using 1-deoxy L-fructose prepared in the same manner as in Example 4, the epimerization reaction thereof was carried out by the same method as in Example 1.

[Structural Analysis of the Product 1-Deoxy L-Psicose]

By the same HPLC analysis of the reaction solution as in Example 1, it was verified that 1-deoxy L-psicose was produced from 1-deoxy L-fructose.

The structure of the sample obtained by chromatography was certified by NMR. $^{13}C$ NMR and proton NMR of the standard 1-deoxy D-psicose were measured. Generally, the NMR spectra of the D-form and L-form of a sugar coincide together. As the results of the measurement, the same results are obtained, so that it was confirmed that the product was 1-deoxy L-psicose.

The results show that D-tagatose 3-epimerase uses 1-deoxyketohexose as a substrate.

Example 6

Production of 1-Deoxy D-Psicose from 6-Deoxy L-Psicose

As shown in Example 1, 6-deoxy L-psicose was produced from L-rhamnose. The product was reduced and converted to 6-deoxy L-allitol, which was then oxidized to produce 1-deoxy D-psicose.

6-Deoxy L-psicose was chemically reduced to produce 6-deoxy L-altritol and 6-deoxy L-allitol. Using chromatography on a column packed with a calcium ion exchange resin for use in separation of various sugars, these sugars were separated. By the method, 6-deoxy L-allitol was obtained.

Using the same microorganism as in Example 4, 6-deoxy L-allitol was oxidized to 1-deoxy D-psicose.

[Structural Analysis]

The product 1-deoxy D-psicose and the chemically synthesized 1-deoxy D-psicose were measured with $^{13}$C NMR and proton NMR, and their structures were compared with each other. The results are shown in FIGS. 15 and 16.

The upper chart in FIG. 15 shows the $^{13}$C NMR spectrum of the chemically synthesized 1-deoxy D-psicose, while the lower chart shows the $^{13}$C NMR spectrum of the 1-deoxy D-psicose produced at the experiment. As shown in the charts, their spectra completely coincide together.

Example 7

Production of 1-Deoxy D-Fructose from 1-Deoxy D-Psicose

Using D-tagatose 3-epimerase, 1-deoxy D-fructose was produced from 1-deoxy D-psicose as the substrate as prepared in Example 6.

Using D-tagatose 3-epimerase prepared by the same method as in Example 1, 1-deoxy D-psicose as a substrate was epimerized at position 3. The reaction product was separated by the chromatography described above, to obtain a pure specimen.

[Structural Analysis]

The chemically synthesized 1-deoxy L-fructose and the product were measured of their NMR spectra for comparison. Because the chemically synthesized 1-deoxy D-fructose is hardly available, 1-deoxy D-psicose was used as a subject for the comparison. Since a D-form sugar and the L-form sugar thereof have the same NMR spectrum, 1-deoxy D-psicose can be used as such comparative standard substance.

In FIG. 17, the upper chart shows $^{13}$C NMR of 1-deoxy L-fructose, while the lower chart shows $^{13}$C NMR of 1-deoxy D-fructose.

In FIG. 18, the upper chart shows proton NMR of 1-deoxy L-fructose, while the lower chart shows proton NMR of 1-deoxy D-fructose produced in this experiment. These spectra completely coincide with each other.

Example 8

Production of 1-Deoxy D-Sorbose from 1-Deoxy D-Tagatose

Using D-tagatose 3-epimerase, 1-deoxy D-sorbose was produced from the chemically synthesized 1-deoxy D-tagatose as the substrate.

The chemically synthesized 1-deoxy D-tagatose reacted with the D-tagatose 3-epimerase prepared by the same method as in Example 1 by a general method, to verify the product by chromatography. Consequently, the peaks of 1-deoxy D-sorbose and 1-deoxy D-tagatose were confirmed. Via separation, 1-deoxy D-sorbose could be produced.

Example 9

Production of 6-Deoxy L-Sorbose from L-Fucose (6-Deoxy L-Galactose)

With D-arabinose isomerase, L-fucose (6-deoxy L-galactose) was isomerized to 6-deoxy L-tagatose, which was further epimerized with D-tagatose 3-epimerase, to produce 6-deoxy L-sorbose.

With D-arabinose isomerase generated by *Klebsiella pneumoniae* ST. 40BXX, L-fucose (6-deoxy L-galactose) as a substrate reacted. As the results of HPLC analysis, 10% of 6-deoxy L-galactose was converted to 6-deoxy L-tagatose to equilibrium. From the mixture in equilibrium was obtained a pure specimen of 6-deoxy L-tagatose by chromatography according to a routine method.

Using the D-tagatose 3-epimerase prepared by the same method as in Example 1, 6-deoxy L-tagatose as a substrate was subjected to the enzymatic reaction. Consequently, an equilibrium mixture was obtained just when about 80% of 6-deoxy L-tagatose was converted to 6-deoxy L-sorbose.

Example 10

Production of 1-Deoxy- and 6-Deoxy D-Tagatose from L-Fucose (6-Deoxy L-Galactose) and the Enantiomer D-Fucose (6-Deoxy D-Galactose)

Via a chemical reduction method with Raney-nickel (pressure at 1.2 MPa, agitation at 700 rpm, and a temperature of 50° C.), first, 6-deoxy L-galactitol and 6-deoxy D-galactitol were prepared from starting materials L-fucose and D-fucose, respectively. Subsequently, the galactitol was oxidized, and the resulting individual deoxy sugar alcohols as substrates were subjected to a reaction with washed bacterial cells [the composition for the bacterial cell reaction: bacterial cell at $OD_{600}$=40; 50 mM Tris-HCl buffer (pH 8.0); substrate at 1%], using *Enterobacter agglomerans* strain 221e (FERM BP-4700) [cultured in a culture broth (erythritol at 1.0 w/v %, yeast extract at 0.5 w/v %, polypeptone at 0.5 w/v %, common salt at 0.5 w/v %, and glycerol at 1.0 w/v %) at 30° C. and collected and washed] (see JP-A-08-056659).

The HPLC analysis results show that the bacterium oxidized and converted 6-deoxy L-galactitol to 1-deoxy D-tagatose or oxidized and converted 6-deoxy D-galactitol to 6-deoxy D-tagatose.

The results of the oxidation of 6-deoxy L-galactitol and 6-deoxy D-galactitol using the bacterial strain indicate that the bacterial cell could recognize and convert the sugar structures despite the presence of methyl group at positions 1 and 6, preferentially to D-tagatose.

[Purification of Reaction Product]

By deionization, decoloring, filtration and evaporation of the reaction mixture, a crystal could be obtained.

[Structural Analysis of Product 1-Deoxy D-Tagatose]

By HPLC analysis, the production of 1-deoxy D-tagatose from 6-deoxy L-galactitol was confirmed. The results are shown in FIG. 19.

The structure of the resulting sample was verified by NMR. The results are shown in FIG. 20.

[Structural Analysis of the Product 6-Deoxy D-Tagatose]

By HPLC analysis, the production of 6-deoxy D-tagatose from 6-deoxy D-galactitol was verified. The results are shown in FIG. 21.

The structure of the resulting sample was verified by NMR. The results are shown in FIG. 22.

The biochemical reaction in the present Example to produce 1-deoxy and 6-deoxy D-tagatose from L-fucose (6-deoxy L-galactose) and the enantiomer D-fucose (6-deoxy D-galactose), respectively are shown in Chemical schemes 1 and 2.

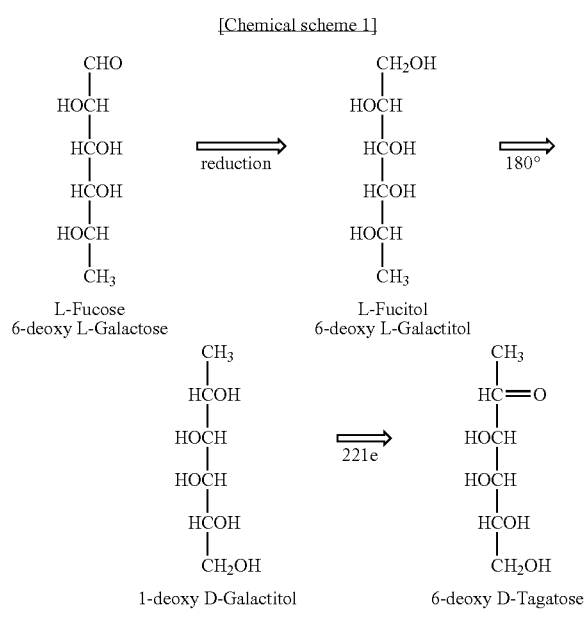

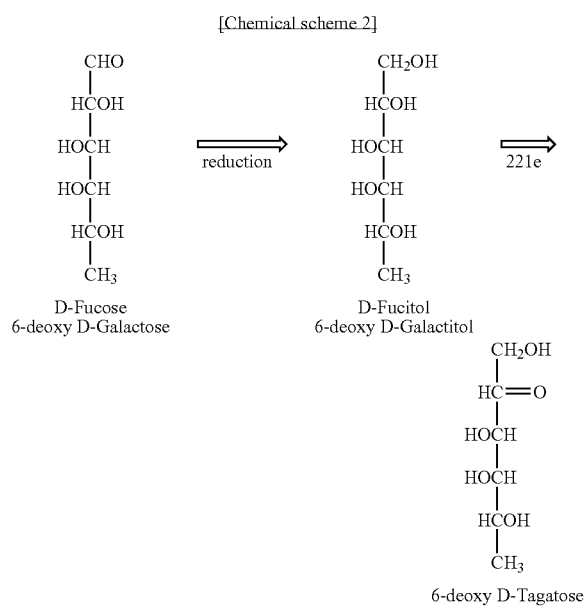

Example 11

Production of 1-Deoxy D-Psicose from L-Rhamnose by a Biological/Chemical Approach As shown in FIG. 23, first, 6-deoxy L-psicose was prepared from L-rhamnose, using L-rhamnose isomerase and D-tagatose 3-epimerase (The Annual Meeting of the Japan Society of Bioscience, Biotechnology and Agrochemistry 2007). As a consequence of the hydrogenation with a nickel catalyst under high-pressure conditions, a mixture of 1-deoxy D-allitol (6-deoxy-L-allitol) and 1-deoxy D-talitol (6-deoxy-L-tallitol) was obtained (FIGS. 24 and 26). The mixture as a substrate was subjected to a bacterial cell reaction with the bacterial strain IK7 (NITE BP-271) of the genus *Enterobacter* (FIGS. 25 and 27). Consequently, only 1-deoxy D-allitol was selectively oxidized to 1-deoxy D-psicose. Almost no reduction of the total weight of both the substrates with the bacterial strain IK7 of the genus *Enterobacter* was observed. The productivity of 1-deoxy D-psicose from 1-deoxy D-allitol was about 90%. The reaction products were separated from each other. Consequently, 1-deoxy D-psicose and 1-deoxy D-talitol were obtained individually as pure products. A photograph of the crystal of the resulting 6-deoxy L-psicose is shown in FIG. 28. The product was identified by comparison with the chemically synthesized 1-deoxy D-psicose and confirmed on the basis of the coincidence of the $^{13}$C NMR spectra (FIG. 29) of the two and the optical rotation degrees of the two.

Optical rotation $[\alpha]^{20}$ (conc. 1.00%, $H_2O$)
Authentic +1.0
Product +1.1

Additionally, the data on the authentic sample depends on the reference [Jones, N. A. and et al. Synthesis of and NMR studies on the four diasteromeric 1-deoxy-d-ketohexoses, Tetrahedron: Asymmetry (2007)].

Example 12

Production of 6-Deoxy L-Glucose and 6-Deoxy L-Fructose

In the presence of the Raney-nickel catalyst, L-rhamnose (10 w/v %) was completely reduced at a temperature of 50° C. and a pressure of 1.2 MPa, to produce 6-deoxy L-mannitol. Using the resulting 6-deoxy L-mannitol as a substrate, 6-deoxy L-fructose was produced. A freshly separated *Enterobacter* sp. 230S was used for selectively oxidizing the carbon in 6-deoxy L-mannitol at position 2 to prepare 6-deoxy L-fructose. The microorganism was cultured in a mineral salt-added culture medium supplemented with D-sorbitol (0.8 w/v %) and glycerol (0.2 w/v %) under agitation at a temperature of 30° C. and 300 rpm, for 24 hours. The culture was centrifuged at 12,000 rpm for 30 minutes, to harvest the bacterial cells, which were then washed twice with 50 mM Tris-HCl buffer (pH 10). The washed bacterial cells were suspended in the same buffer for use in converting 6-deoxy L-mannitol to 6-deoxy L-fructose. The reaction was done in various substrate concentrations in a 5-liter bioreactor (ABLE DPL-2, Japan), using the bacterial cells of $OD_{600}$=40, a handling volume of 0.5 liter, an agitation speed of 200 rpm, an air flow rate of 0.2 liters/min and a temperature of 30° C.

The present inventors already publicly report that *K. pneumonia* 40bXX catalyzes the conversion from L-fructose to L-glucose. By the same method, attempts were made to produce 6-deoxy L-glucose from 6-deoxy L-fructose (the product at the previous step). *K. pneumonia* 40bXX was cultured in a culture medium containing 0.5 w/v % polypeptone, 0.5 w/v % yeast extract, and 0.5 w/v % salt as supplemented with $MnCl_2$ (1 mM). After 24-hour incubation, the culture was centrifuged at 1200×g for 10 minutes, to recover the bacterial cells. The recovered bacterial cells were washed twice with 50 mM glycine-NaOH buffer (pH 9.0), and then centrifuged at 1200×g for 10 minutes. The washed bacterial cells were disrupted with a motor, to which activated alumina was added for grinding the bacterial cells to recover a crude enzyme. The partially purified enzyme D-AI (400 U) is preliminarily adjusted with 50 mM glycine-NaOH, and then immobilized on 30 g (wet weight) of Chitopearl BCW 2510 for use in the reaction. The rearrangement reaction was progressed in an L-tube containing 1% 6-deoxy L-fructose, the immobilized D-AI (40 U), 50 mM Tris-HCl buffer (pH 9.0) and $MnCl_2$ (to a final concentration: 1 mM) at 40° C.

[Separation Method]

In case of 6-deoxy L-mannitol, the conversion ratio was close to 100%, and therefore, the separation step simply comprises removing the Raney-nickel from the reaction mixture by filtration.

Using the remaining 230S bacterial cells, 6-deoxy L-fructose was produced via oxidation of 6-deoxy L-mannitol. The material flowing on the surface was treated with active charcoal a whole day and night, and finally, the active charcoal was removed by filtration through a cellulose filter under aspiration. The filtrate was deionized with a mixture of Diaion SK1B ($H^+$ type) and Amberlite IRA-411 ($CO_3$ 2-type). The volume of the filtrate was just an appropriate volume for rotary evaporators in vacuum. The concentrated filtrate was applied to a Dowex 50W-X2 column of $Ca^{2+}$ type. The column was eluted with distilled water, and the resulting eluate fractions were collected for HPLC analysis.

[Identification]

6-Deoxy L-mannitol and 6-deoxy L-fructose were identified by HPLC analysis (FIG. 30), optical rotation measurement, and $^{13}C$ NMR.

The HPLC analysis results of the purified 6-deoxy L-fructose are shown in FIG. 30. Additionally, the optical rotation of the produced 6-deoxy L-fructose was +12.9, while the known optical rotation of 6-deoxy L-fructose as reported in references was +13.6. Still further, $^{13}C$ NMR of the produced 6-deoxy L-fructose absolutely coincides with the $^{13}C$ NMR of 6-deoxy L-fructose (FIG. 31).

[Results]

6-Deoxy L-mannitol can readily be produced via chemical reduction of 6-deoxy L-mannose. At a productivity close to 99%, 6-deoxy L-mannose is completely converted to 6-deoxy L-mannitol. When the initial concentrations of 6-deoxy L-mannitol were 3%, 4% and 5%, almost 90%, 70% and 65%, respectively of 6-deoxy L-mannitol produced 6-deoxy L-fructose and 1-deoxy L-fructose, using the washed bacterial cell reaction.

The final ratio of 6-deoxy L-fructose to 1-deoxy L-fructose in the reaction mixture was about 8:2. In the bioreactor, 6-deoxy L-mannitol (30 g/l) was completely consumed in about 10 hours to produce 6-deoxy L-fructose and 1-deoxy L-fructose; the final productivity of 6-deoxy L-fructose through various purification steps from 6-deoxy L-mannitol is about 50%.

In case of isomerization of 6-deoxy L-fructose to 6-deoxy L-glucose with the immobilized D-arabinose isomerase, the HPLC peak of 6-deoxy L-glucose could not be detected because the enzyme activity was very low. Therefore, 6-deoxy L-glucose was not separated or identified at the present time.

6-Deoxy L-fructose can be produced from 6-deoxy L-mannose, using L-rhamnose isomerase. Since a mixture of equal amounts of such sugars exerts overlapped peaks, however, it is totally difficult to separate 6-deoxy L-fructose and 6-deoxy L-mannose from each other. Thus, such separation is unrealistic. At the experiment, 6-deoxy L-fructose could be purified from 6-deoxy L-mannose at a productivity yield of about 50%, using combinations of chemical methods and biochemical methods.

Example 13

Novel Biochemical Production Method of 1-Deoxy L-Psicose En Route 6-Deoxy L-Mannitol and 1-Deoxy L-Fructose from L-Rhamnose

[Raw Materials and Method]
[Reagents, Etc.]

L-Rhamnose and other biochemical products were all purchased from Sigma Chemical Co. (MO, USA) and Wako Pure Chemical Industry Co., Ltd. (Osaka, Japan), and these were all certified of their reagent grades. 50 mM Tris-HCl buffer for use in the oxidation of L-rhamnose was prepared from tris(hydroxymethyl) aminoethane $H_2NC(CH_2OH)_3$ adjusted to pH 9.0 with 1.0N HCl. Hydrogenation of L-rhamnose was carried out in a hydrogenation apparatus TEM-1000M (Taitasu Techno Co., Ltd., Japan). Microbial culturing and oxidation were facilitated in a bioreactor (TS-M-15L fermentation tank and TS-M-5L fermentation tank) available from Takasugi Seisakusho Co., Ltd. Polyol oxidation and ketose accumulation in the reaction mixture is determined by the Nelson-Somogyi method using an ultraviolet-visible spectrophotometer (U.V.-1700 pharmaspec, Shimadzu Seisakusho, Kyoto). Using acetone as an initial standard, $^{13}C$ NMR spectra (Burker AMX500, 126 MHz) are recorded in $D_2O$. The optical rotation is recorded with Jasco R1030 polarimeter with $Na^+$ lamp (Jasco, Tokyo, Japan) of an $H_2O$ polarimeter deionized of a 1-dm path length, at 20° C. The concentration was up to g 100 $mL^{-1}$ liter. The product was analyzed by high-performance liquid chromatography (Hitachi GL-611 column, Tokyo, Japan and Shimadzu RID-6A refractive index detector, Kyoto <Japan>) at 600° C., with $10^{-4}$ M NaOH as an eluent at a flow rate of 1.0 ml/min.

[Chemical Reduction of L-Rhamnose to 6-Deoxy L-Mannitol]

Raney-nickel (catalyst) was added to a solution of L-rhamnose (50 g) in 300 ml of water; the reaction was progressed in a reactor at a hydrogen pressure of 1.2 MPa while the total reaction volume was adjusted to 500 ml. Subsequently, the reactor was heated to 50° C. for 8 hours, to reduce L-rhamnose to 6-deoxy L-mannitol.

[Oxidation of 6-Deoxy L-Mannitol to 1-Deoxy L-Fructose]

The bacterial strain IK7 (NITE BP-271) of the genus *Enterobacter* is used for biochemical conversion of 6-deoxy L-mannitol to 1-deoxy L-fructose. For generating 1-deoxy L-fructose via a bacterial cell reaction, the bacterial strain was cultured in a 2% TBS culture medium supplemented with 1% D-mannitol at 37° C. The conversion reaction was carried out in a 5.0-L bioreactor at 37° C. and an agitation velocity of 120 rpm at an air flow rate of 0.5 l/min for 12 hours. The composition of the reaction mixture was as follows: 50 g (5 w/v %) 1-deoxy L-mannitol and the washed bacterial cells at $OD_{600}$=50 ($A_{600}$) as the density of the bacterial cells were suspended in Tris-HCl buffer (1000 ml, 50 mM, pH 9.0).

[Isomerization of 1-Deoxy L-Fructose to 1-Deoxy L-Psicose]

For isomerization of 1-deoxy L-fructose to 1-deoxy L-psicose, D-tagatose 3-epimerase derived from *Pseudomonas cichorii* strain ST24 (FERM BP-2736) was used. D-TE obtained from the recombinant *Escherichia coli* was partially purified and immobilized using Chitopearl BCW 2510 so as to construct a bioreactor. 1-Deoxy L-fructose (5%) dissolved in Tris-HCl buffer (1,000 ml, 50 mM, pH 7.5) flowed in the bioreactor at 42° C.

[Separation Method]

Matters floating on the surface as obtained at the individual steps were treated and decolored with active charcoal, from which the active charcoal used for the treatment was filtered off. The resulting filtrate was deionized with a mixture of Diaion SK1B ($H^+$ type; Mitsubishi Chemical, Tokyo) and Amberlite IRA-411 ($CO_3^{2-}$ type, Muromachi Tecynos, Tokyo) ion exchange resins. The deionized filtrate was evaporated at 40° C., and concentrated. After concentration, the mixture was separated on a one-pass separation system comprising eight columns bound together with two pumps, where 2.5 L of UKB-555 ion exchange resins ($Ca^{2+}$ type, Mitsubishi Chemical, Tokyo) were filled in each of the columns. The separated fraction was concentrated to 50%, and the concentrate was stored in a desiccator for crystallization.

[Identification]

The products obtained at the individual steps were identified by HPLC analysis, optical rotation measurement, and $^{13}$C NMR.

$^{13}$C NMR spectrum of the produced 1-deoxy L-psicose is shown in FIG. 32. Additionally, the optical rotation of the produced 1-deoxy L-psicose is as follows.

| Optical rotation | 1-deoxy L-psicose (p) | −1.0 |
|---|---|---|
| | 1-deoxy D-psicose | +1.15 |

[Results]

Chemical Reduction of L-Rhamnose to 6-Deoxy L-Mannitol

L-Rhamnose in water when L-rhamnose is used at 10 w/v % as a substrate is hydrogenated with a nickel catalyst at 50° C. at a pressure of 1.2 MPa to L-rhamnitol at a yield of 100%. By the method, not any separation process is required. FIG. 33 shows the results of HPLC analysis.

Oxidation of 6-Deoxy L-Mannitol to 1-Deoxy L-Fructose

When 5 w/v % 6-deoxy L-mannitol is used as a substrate, the 6-deoxy L-mannitol is oxidized with a bacterial cell reaction of the *Enterobacter* strain IK7 (NITE BP-271) to 1-deoxy L-fructose at a yield of 90%. 1-Deoxy L-fructose is separated by the following method. FIG. 34 shows the results of HPLC analysis.

Isomerization of 1-Deoxy L-Fructose to 1-Deoxy L-Psicose

When 5 w/v % 1-deoxy L-fructose was used as a substrate, the 1-deoxy L-fructose was isomerized with the immobilized D-TE in the bioreactor to 1-deoxy L-psicose at a yield of 25%. FIG. 35 shows the results of HPLC analysis.

[Conclusion]

The novel biochemical production method of 1-deoxy L-psicose from L-rhamnose en route 6-deoxy L-mannitol and 1-deoxy L-fructose is shown in FIG. 36.

[Summary of Outcome of Experimental Results]

(1) D-Tagatose 3-epimerase epimerizes all 1- and 6-deoxyketohexoses at position 3.

(2) 6-Deoxyaldose works as a substrate for aldose isomerase, to possibly produce the corresponding 6-deoxyaldose.

(3) Via reduction of 1- or 6-deoxy D- or L-ketohexose, the corresponding 1- or 6-deoxy sugar alcohol with 6 carbon atoms can be produced. Via reduction of 6-deoxyaldose, further, 6-deoxy sugar alcohol can be produced.

(4) Via oxidation with a microorganism, using 1- or 6-deoxy sugar alcohol as a substrate, the corresponding 1- or 6-deoxyketohexose can be produced.

[Construction of Deoxy-Izumoring as a Production Strategy for all Deoxyhexoses]

Using the outcome described above in (1) through (4), Deoxy-Izumoring as a production strategy for all deoxyhexoses could be constructed. (FIGS. 1 through 3)

On the large ring shown in the figures, all the eight types of 1-deoxyketoses and all the eight types of 6-deoxyketohexose are linked to the individually corresponding deoxyhexoses with D-tagatose 3-epimerase, while two types of deoxyketohexoses are arranged as the group 8. The individual groups are linked with 1- and 6-deoxy hexitols as common products and substrates for redox reactions. The principle is summarized in FIG. 1 on the bottom.

In summary from the left, L-rhamnose (6-deoxy L-mannose) is isomerized to produce 6-deoxy L-psicose, which is epimerized with D-tagatose 3-epimerase to 6-deoxy L-psicose (Example 1). Via a chemical reduction, the resulting epimer is reduced to 6-deoxy glucitol, which is the same as 1-deoxy gulitol when the figure is upside down. Via the oxidation of 1-deoxy gulitol, 1-deoxy D-sorbose can be produced. With D-tagatose 3-epimerase, 1-deoxy D-tagatose can be produced from 1-deoxy D-sorbose (Example 8). This is just one example. The large ring shows the entirety can be linked together by repeating such process. Via the principle, a fundamental backbone to produce all 16 1- and 6-deoxy types of ketohexoses can be established.

Additionally, all the 16 types of 6-deoxyketohexoses are linked to 6-deoxyketohexoses around the ring. Via aldose isomerase, 6-deoxyketohexose can be converted to 6-deoxyketohexose. It is shown that 6-deoxyaldose can be produced from 6-deoxy L-fructose (Example 1). As described above, all the 16 types of 6-deoxyaldoses are linked together around the ring.

As described above, Deoxy-Izumoring in FIGS. 1 through 3 shows that all the 1- and 6-deoxyhexoses can be linked together via enzyme reactions, to reveal a production strategy for all deoxyhexoses. Additionally, all D-form deoxyhexoses are arranged on the right side, while L-form deoxyhexoses are arranged on the left side. All the 1- and 6-deoxyhexoses are apparently arranged so that the production method can be understood instantly. Herein, those marked with arrow heads in dot line in the figures can be overlapped together when the figures are upside down; i.e. those are the same 1-deoxy and 6-deoxy hexitol. The dot line suggests efficient synthetic methods not only for the synthesis on the ring in the figures but also for playing bypass roles.

Deoxyaldose currently existing relatively abundantly in the natural kingdom, namely L-rhamnose (6-deoxy L-mannose) or L-fucose (6-deoxy L-galactose) is used as a starting material for production using Deoxy-Izumoring, which can be effectively utilized for producing these novel deoxyhexoses.

By making an advance in the summary described above, Deoxy-Izumoring with deoxy sugars marked with numerical figures is shown in FIG. 3. With reference to FIG. 3, production of novel deoxyhexoses is described specifically in Examples of Example 14 and thereafter.

FIG. 3 shows the following reactions A through D with arrow heads with different labels, as in FIGS. 1 and 2.

A DTE epimerization
B Polyol oxidation
C Isomerization (isomerization between aldose and ketose)
D Reduction with nickel catalyst (reduction of ketose and aldose to polyol)

Example 14

Production of 6-Deoxy L-Sorbose

The reaction is for the epimerization of 6-deoxy L-tagatose with D-TE to 6-deoxy L-sorbose, which corresponds to the reaction A numbered with 27-26 in FIG. 3.

Under the following conditions, 6-deoxy L-tagatose produced from L-rhamnose reacted with DTE.

<Reaction Conditions>
Substrate: 6-deoxy L-tagatose
Enzyme: immobilized D-tagatose 3-epimerase
Buffer: 50 mM Tris-HCl buffer (pH 7.5)
Temperature: 40° C.

The progress of the reaction was verified by HPLC. As shown in FIG. 37, the production of 6-deoxy L-sorbose was verified. The equilibrium was attained at 6-deoxy L-tagatose and 6-deoxy L-sorbose at a ratio of about 1:3.

These were separated from each other by the following method, to obtain pure 6-deoxy L-sorbose (FIG. 38). The optical rotation was −48.5.

<Separation Method>
Dowex 50W X2
One-pass separation system

The reaction for the production of 6-deoxy L-sorbose from 6-deoxy L-tagatose in the present Example is shown in Chemical scheme 3.

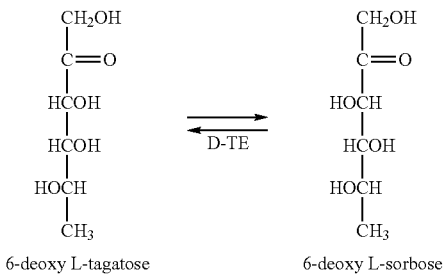

[Chemical scheme 3]

Example 15

Production of 6-Deoxy D-Sorbose

The reaction is for the epimerization of 6-deoxy D-tagatose to 6-deoxy D-sorbose, which corresponds to the reaction A numbered with 3-2 in FIG. 3.

6-Deoxy D-galactitol obtained by a chemical reduction method using Raney-nickel of a starting raw material L-fucose (6-deoxy L-galactose) was oxidized and converted to 6-deoxy D-tagatose, with which DTE reacted under the following reaction conditions.

<Reaction Conditions>
Substrate: 6-deoxy D-tagatose
Enzyme: immobilized D-tagatose 3-epimerase
Buffer: 50 mM Tris-HCl buffer (pH 7.5)
Temperature: 40° C.

<Separation Method>
Dowex 50W X2

The progress of the reaction was verified by HPLC. As shown in FIG. 39, the production of 6-deoxy D-sorbose was verified. The equilibrium was attained in the same fashion as in the case of 6-deoxy L-tagatose: 6-deoxy L-sorbose, which was about 1:3.

The reaction for the production of 6-deoxy D-sorbose from 6-deoxy D-tagatose in the present Example is shown in Chemical scheme 4.

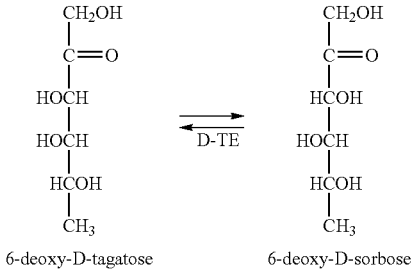

[Chemical scheme 4]

Example 16

Production of 1-Deoxy L-Psicose

The reaction is for the epimerization of 1-deoxy L-fructose with D-TE to 1-deoxy L-psicose, which corresponds to the reaction A numbered with 18-19 in FIG. 3.

1-Deoxy L-fructose produced from L-rhamnose reacted with DTE.

1-Deoxy L-fructose was produced en route 6-deoxy L-mannitol from L-rhamnose.

1-Deoxy L-fructose produced from L-rhamnose reacted with DTE. The reaction conditions are as follows.

<Reaction Conditions>
Substrate: 1-deoxy L-fructose
Immobilized D-TE: 10,000 U (Chitopearl BCW 2510)
Temperature: 42° C.
Agitation: 90 rpm
Volume: 100 ml
Time: 24 hours
Conversion ratio: 75 (F): 25 (P)

It was confirmed that 1-deoxy L-psicose was produced due to the DTE action, while the equilibrium was attained at 75: as the ratio of 1-deoxy L-fructose: 1-deoxy L-psicose. The solution after the reaction was separated by one-pass chromatography. The separation conditions are as follows.

<Separation Conditions>
System: One-pass separation system
Sample: mixture of 30% 1-deoxy L-fructose and 1-deoxy L-psicose
Volume: 100 mL
Flow rate: 60 ml/min
Wait time: 90 min
Fractions: tanks A, B, C and D
Results: pure 1-deoxy L-psicose was obtained.

The purity of 1-deoxy L-fructose (a) and 1-deoxy L-psicose (b) separated from the reaction mixture was analyzed by HPLC. They are so pure as shown in FIG. 40. $^{13}$C NMR spectrum of 1-deoxy L-psicose is shown in FIG. 41. It was certified that the spectrum is identical to the chart shown in FIG. 32.

Example 17

Production of 6-Deoxy D-Fructose

The reaction is for the epimerization of 6-deoxy D-psicose with DTE to 6-deoxy D-fructose, which corresponds to the reaction A numbered with 11-10 in FIG. 3.

1-Deoxy L-psicose prepared via a reaction of 1-deoxy L-fructose with DTE was reduced to obtain 1-deoxy L-allitol, which was then oxidized microbially (IK7), to produce 6-deoxy D-psicose. 1-Deoxy D-psicose thus obtained reacted with DTE. The reaction conditions are as follows.

<Reaction Conditions>
Buffer: Tris (pH 7.5) of 500 μl
Substrate: 1.5% 6-deoxy D-psicose
D-TE: about 100 units
Temperature: 40° C.
Time: 12 hours
Conversion ratio: 50 (S): 50 (P)

It was confirmed that 6-deoxy D-fructose was produced at 50-% equilibrium in the solution after reaction. FIG. 42(a) shows 6-deoxy D-psicose before reaction, while FIG. 42(b) shows the HPLC analysis of the reaction mixture after reaction.

Example 18

Production of 6-Deoxy L-Sorbose

The reaction is for the isomerization of 6-deoxy L-tagatose with DTE to 6-deoxy L-sorbose, which corresponds to the reaction A numbered with 22-23 in FIG. 3.

1-Deoxy L-psicose produced via the reaction of 1-deoxy L-fructose with DTE was reduced to obtain 1-deoxy L-talitol. The 1-deoxy L-talitol was oxidized microbially (40b) to produce 1-deoxy L-tagatose. 1-Deoxy L-tagatose thus produced reacted with DTE. The reaction conditions are as follows.

<Reaction Conditions>
Buffer: Tris (pH 7.5) of 500 µl
Substrate: 1.0% 6-deoxy L-tagatose
D-TE: about 100 units
Temperature: 42° C.
Time: 12 hours
Conversion ratio: 20 (S): 80 (P)

In the solution after reaction, 6-deoxy L-sorbose was produced. The ratio of the substrate and the product was 1:4. FIG. 43(*a*) shows 6-deoxy L-tagatose as the substrate, while FIG. 43(*b*) shows the results of HPLC analysis of the reaction mixture after reaction.

Example 19

Production of 1-Deoxy D-Tagatose

The reaction is for producing 1-deoxy D-tagatose via a microbial oxidation of 6-deoxy L-galactitol, which corresponds to the reaction B numbered with 46=39-13 in FIG. 3.

L-Fucose (6-deoxy L-galactose) was reduced, for a microbial oxidation of the resulting L-fucitol (6-deoxy L-galactitol) with *E. agglomerans* 221e [the bacterial cell at $OD_{600}$=30, Tris-HCl buffer (pH 8.0) of 50 mM, the substrate 6-deoxy L-galactitol at 1%] at 30° C. for 6 hours. Only 1-deoxy D-tagatose was produced. FIG. 44(*a*) shows the reaction mixture after reaction, while FIG. 44 (*b*) shows the results of HPLC analysis of the produced 1-deoxy D-tagatose. The optical rotation was +14.0. $^{13}$C NMR spectrum thereof is shown in FIG. 45.

The reaction for the production of 6-deoxy L-galactitol from 1-deoxy D-tagatose in this Example is shown in Chemical scheme 5.

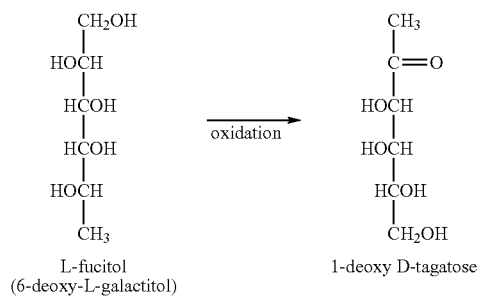

Example 20

Production of 1-Deoxy L-Tagatose

The reaction is for producing 1-deoxy L-tagatose via a microbial oxidation of 6-deoxy D-galactitol, which corresponds to the reaction B numbered with 34=43-22 in FIG. 3.

L-Fucose (6-deoxy L-galactose) was reduced to produce L-fucitol (6-deoxy L-galactitol), which was then used as a substrate for a microbial oxidation with *K. pneumoniae* 40b at 30° C. [the composition for the bacterial reaction: the bacterial cell at $OD_{600}$=30, Tris-HCl buffer (pH 8.0) of 50 mM, the substrate at 1%] at 30° C. FIG. 46 shows the results of HPLC analysis in the course of producing 1-deoxy L-tagatose, which indicates that 1-deoxy L-tagatose can be produced.

The reaction for the production of 1-deoxy L-tagatose from 6-deoxy D-galactitol in this Example is shown in Chemical scheme 6.

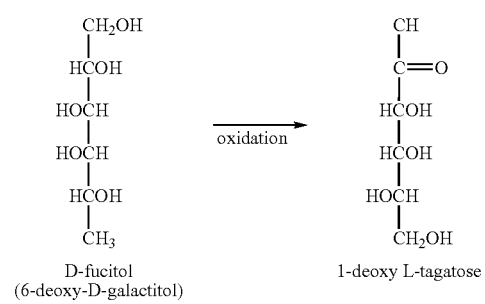

Example 21

Production of 6-Deoxy D-Tagatose

The reaction is for producing 6-deoxy D-tagatose via a microbial oxidation of 6-deoxy D-galactitol, which corresponds to the reaction B numbered with 34-3 in FIG. 3.

D-Fucose (6-deoxy D-galactose) was reduced to produce D-fucitol (6-deoxy D-galactitol), which was then used as a substrate for a microbial oxidation with *E. agglomerans* 221e [the composition for the bacterial reaction: the bacterial cell at $OD_{600}$=30, Tris-HCl buffer (pH 8.0) of 50 mM, the substrate 6-deoxy L-galactitol at 1%] at 30° C. FIG. 47(*a*) shows HPLC of the reaction mixture after reaction, while FIG. 47(*b*) shows HPLC of the separated 1-deoxy D-tagatose purified. The optical rotation was −0.8, and FIG. 48 shows $^{13}$C NMR spectrum.

The reaction for the production of 6-deoxy D-tagatose from 6-deoxy D-galactitol in this Example is shown in Chemical scheme 7.

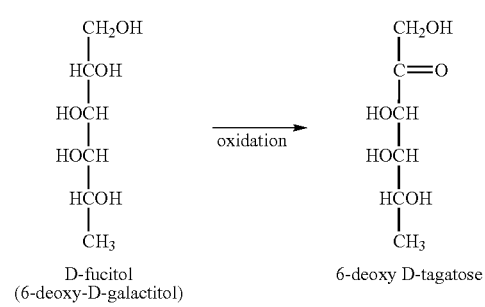

Example 22

Production of 1-Deoxy L-Fructose

The reaction is for producing 1-deoxy L-fructose via a microbial oxidation of L-rhamnitol (6-deoxy L-mannitol), which corresponds to the reaction B numbered with 41=48-31 in FIG. 3.

Under the following conditions, a hydrogenase reaction with the *Enterobacter* bacterial strain IK7 (NITE BP-271) was done using L-rhamnitol as the substrate.

<Reaction Conditions>
Substrate: 5% L-rhamnitol
Buffer: 50 mM Tris-HCl (pH 9.0)
Concentration of bacterial cell: A600$_{-40}$ (OD$_{600}$ 40)
Temperature: 37° C.
Agitation: 120 rpm
Air flow rate: 1.0 L/min
Time: 12 hours
Volume: 1.0 L
Conversion ratio: 90%

Separation and purification were done under the following conditions.

<Separation Conditions>
System: One-pass separation system
Sample: mixture of 30% L-rhamnitol and 1-deoxy L-fructose
Volume: 300 mL
Flow rate: 60 ml/min
Wait time: 120 min
Fractions: tanks A, B, C and D
Results: pure 1-deoxy L-fructose was obtained at two runs.

FIG. 49(*a*) shows the HPLC analysis results of L-rhamnitol and FIG. 49(*b*) shows those of the separated 1-deoxy L-fructose purified. FIG. 50 shows $^{13}$C NMR spectrum of the separated and purified 1-deoxy L-fructose.

Example 23

Production of 6-Deoxy D-Psicose and 6-Deoxy L-Tagatose

The reactions are for producing 6-deoxy D-psicose and 6-deoxy L-tagatose via a microbial oxidation of 1-deoxy L-allitol and 1-deoxy L-talitol, respectively, which correspond to the reactions numbered with 47=38-11 and 29=28-27 in FIG. 3.

6-Deoxy D-psicose and 6-deoxy L-tagatose were produced. First, 1-deoxy L-psicose was reduced to 1-deoxy L-allitol and 1-deoxy L-talitol [FIG. 51(*a*)]. Without separation, the reduction products were subjected to an oxidation reaction with the *Enterobacter* strain IK7 (NITE BP-271) under the following condition.

<Reaction Conditions>
Buffer: Tris (pH 9.0)
Substrate: a mixture of 1% 1-deoxy L-allitol and 1-deoxy L-talitol
Bacterial cell: 30 (A$_{600}$) (OD$_{600}$ 30)
Temperature: 37° C.
Agitation: 100 rpm
Time: 12 hours
Volume: 100 ml
Conversion ratio: 100%

Separation and purification were carried out under the following separation conditions.

<Separation Conditions>
System: Dowex 50 Ca$^{2+}$; column: 100 cm×2
Sample: mixture of 20% 1-deoxy L-allitol and 1-deoxy L-talitol
Volume: 10 mL
Flow rate: 0.5 ml/min
Wait time: 90 min
Fraction: 2.0 ml/tube
Results: pure 6-deoxy D-psicose and 6-deoxy L-tagatose were obtained.

As shown in the HPLC analysis results in FIG. 51, (b) 6-deoxy D-psicose and 6-deoxy L-tagatose could be produced from (a) 1-deoxy L-allitol and 1-deoxy L-talitol, respectively. The individual HPLC charts of the separated and purified 6-deoxy D-psicose and 6-deoxy L-tagatose are shown as (c) and (d), respectively.

Example 24

Production of 6-Deoxy L-Tagatose

The reaction is for producing 6-deoxy L-tagatose by isomerizing 6-deoxy L-galactose, which corresponds to the reaction C numbered with 63-27 in FIG. 3.

Under the following reaction conditions, L-fucose (6-deoxy L-galactose) was isomerized with D-arabinose isomerase, to produce 6-deoxy L-tagatose.

<Reaction Conditions>
Substrate: 10% L-fucose (6-deoxy L-galactose)
Enzyme: immobilized D-arabinose isomerase
Buffer: 50 mM glycine-NaOH buffer (pH 9.0)
Ion: 1 mM MnCl$_2$
Temperature: 40° C.

Separation was done by the following method.

<Separation Method>
Dowex 50W X2
One-pass separation system

FIG. 52(*a*) shows HPLC after reaction, while FIG. 52(*b*) shows HPLC of the separated and purified product (6-deoxy L-tagatose). The optical rotation was +0.9. The $^{13}$C NMR spectrum is shown in FIG. 53.

The reaction for the production of 6-deoxy L-tagatose from 6-deoxy L-galactose in this Example is shown in Chemical scheme 8.

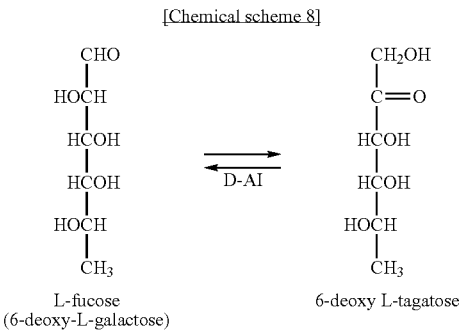

[Chemical scheme 8]

L-fucose (6-deoxy-L-galactose) → 6-deoxy L-tagatose (D-AI)

Example 25

Production of 6-Deoxy L-Talose

The reaction is for producing 6-deoxy L-talose via the isomerization of 6-deoxy L-tagatose, which corresponds to the reaction C numbered with 27-64 in FIG. 3.

6-Deoxy L-talose was produced by allowing L-rhamnose isomerase to react with 6-deoxy L-tagatose produced from L-fucose.

<Reaction Conditions>
Substrate: 6-deoxy L-tagatose
Enzyme: immobilized L-rhamnose isomerase
Buffer: 50 mM glycine-NaOH buffer (pH 9.0)
Ion: 1 mM $MnCl_2$
Temperature: 40° C.
Separation was done by the following method.

<Separation Method>
Separation by Chromatography

FIG. 54(a) shows HPLC of the reaction mixture after reaction; and FIG. 54(b) shows HPLC of the separated and purified product (6-deoxy D-talose). FIG. 54(c) shows $^{13}C$ NMR spectrum of 6-deoxy D-talose separated and purified. 6-Deoxy L-talose could be produced with L-rhamnose isomerase.

The reaction of the production of 6-deoxy L-talose from 6-deoxy L-tagatose in this Example is shown in Chemical scheme 9.

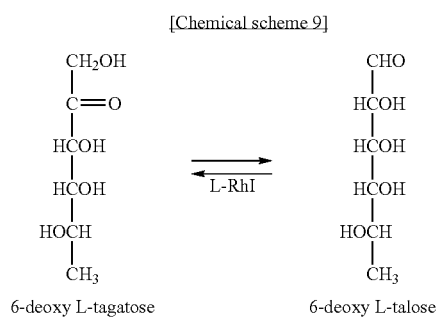

[Chemical scheme 9]

6-deoxy L-tagatose → 6-deoxy L-talose (L-RhI)

Example 26

Production of 6-Deoxy D-Allose and 6-Deoxy D-Altrose

The reactions are for producing 6-deoxy D-allose and 6-deoxy D-altrose via the isomerization of 6-deoxy D-psicose, which correspond to the reactions C numbered with 11-55 and 11-56, respectively, in FIG. 3.

6-Deoxy aldose was produced via the isomerization reaction under the following conditions, using 6-deoxy D-psicose produced from 6-deoxy D-allitol as the raw material.

<Reaction Conditions>
Substrate: 1.0% 6-deoxy D-psicose of 500 μl
Buffer: 50 mM glycine-NaOH buffer (pH 9.0) of 500 μl
L-Rhamnose isomerase: 100 units
$MnCl_2$: 50 μl
Temperature: 42° C.
Time: 24 hours
Conversion ratio: 40 (s): 60 (ps)

FIG. 55(a) shows HPLC of 6-deoxy D-psicose used as the substrate; and FIG. 55(b) shows HPLC after the reaction with L-rhamnose isomerase. The results show that 6-deoxy D-altrose and 6-deoxy D-allose could be produced from 6-deoxy D-psicose.

Example 27

Production of 6-Deoxy D-Talose

The reaction is for producing 6-deoxy D-talose via the isomerization of 6-deoxy D-tagatose, which corresponds to the reaction C numbered with 3-52 in FIG. 3.

6-Deoxy D-talose was produced by allowing L-ribose isomerase to react with 6-deoxy D-tagatose produced from D-fucose.

<Reaction Conditions>
Substrate: 6-deoxy D-tagatose
Enzyme: immobilized L-ribose isomerase
Buffer: 50 mM glycine-NaOH buffer (pH 9.0)
Ion: 1 mM $MnCl_2$
Temperature: 30° C.

The ratio after the isomerization was 2:3 as 6-deoxy D-tagatose: 6-deoxy D-talose. FIG. 56 shows the HPLC analysis results of the reaction mixture after the reaction with L-ribose isomerase.

The reaction of the production of 6-deoxy D-talose from 6-deoxy D-tagatose in this Example is shown in Chemical scheme 10.

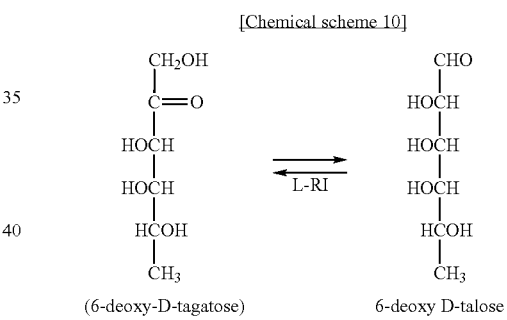

[Chemical scheme 10]

(6-deoxy-D-tagatose) → 6-deoxy D-talose (L-RI)

Example 28

Production of 6-Deoxy L-Galactitol

The reaction is for producing 6-deoxy L-galactitol via the reduction of 6-deoxy L-galactose, which corresponds to the reaction D numbered with 63-46 in FIG. 3.

D-Fucose (6-deoxy D-galactose) was reduced [a composition in total of 500 ml containing D-fucose at 1% and 20 ml of the Raney-nickel catalyst] to produce D-fucitol (6-deoxy D-galactitol). FIG. 57(a) shows HPLC analysis results of D-fucose before reduction and FIG. 57(b) shows HPLC analysis results of 6-deoxy L-galactitol after the reduction. The optical rotation of 6-deoxy L-galactitol was +1.7, and FIG. 58 shows $^{13}C$ NMR spectrum of 6-deoxy L-galactitol.

The reaction for the production of 6-deoxy L-galactitol from 6-deoxy L-galactose in this Example is shown in Chemical scheme 11.

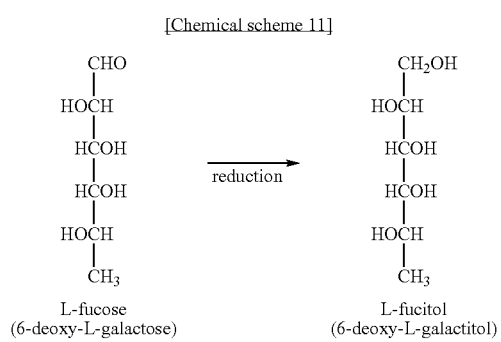

[Chemical scheme 11]

L-fucose (6-deoxy-L-galactose) → reduction → L-fucitol (6-deoxy-L-galactitol)

Example 29

Production of 6-Deoxy D-Galactitol

The reaction is for producing 6-deoxy D-galactitol via the reduction of 6-deoxy D-galactose, which corresponds to the reaction D numbered with 51-34 in FIG. 3.

L-Fucose (6-deoxy L-galactose) was reduced [a composition in total of 500 ml containing L-fucose at 1% and 20 ml of the Raney-nickel catalyst] to produce L-fucitol (6-deoxy L-galactitol). FIG. 59(*a*) shows HPLC analysis results of L-fucose before reduction and FIG. 59(*b*) shows HPLC analysis results of 6-deoxy D-galactitol after the reduction. The optical rotation of 6-deoxy L-galactitol was −1.7, and FIG. 60 shows $^{13}$C NMR spectrum of 6-deoxy D-galactitol.

The reaction for the production of 6-deoxy D-galactitol from 6-deoxy D-galactose in this Example is shown in Chemical scheme 12.

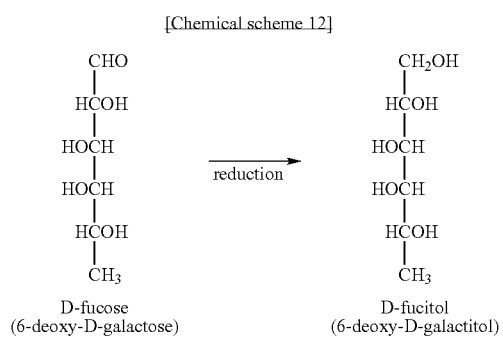

[Chemical scheme 12]

D-fucose (6-deoxy-D-galactose) → reduction → D-fucitol (6-deoxy-D-galactitol)

Example 30

Production of L-Rhamnitol

The reaction is for producing L-rhamnitol via the reduction of L-rhamnose by a hydrogenation method, which corresponds to the reaction D numbered with 58-41 in FIG. 3.

L-Rhamnitol (6-deoxy L-mannitol) was produced by reducing L-rhamnose (6-deoxy L-mannose) under the following reaction conditions.

<Reaction Conditions>
Substrate: 5% L-rhamnose
Catalyst: nickel
H$_2$ pressure: 1.2 MPa
Temperature: 50° C.
Agitation: 700 rpm
Time: 12 hours
Volume: 500 ml
Conversion ratio: 100%

FIG. 61(*a*) shows HPLC analysis results of L-rhamnose before reduction; and FIG. 61(*b*) shows HPLC analysis results of L-rhamnitol after the reduction. In such manner, L-rhamnitol could be produced readily.

Example 31

Production of L-Rhamnitol

The reactions are for producing 1-deoxy L-mannitol and 1-deoxy L-sorbitol via the reduction of 1-deoxy L-fructose by a hydrogenation method, which correspond to the reactions D numbered with 31-32 and 31-48, respectively in FIG. 3.

1-Deoxy L-mannitol and 1-deoxy L-sorbitol were produced by reducing 1-deoxy L-fructose under the following reaction conditions. By a general method with the Raney-nickel, these two polyols could be produced at almost equal amounts.

<Reaction Conditions>
Substrate: 5% 1-deoxy L-fructose
Catalyst: nickel
H$_2$ pressure: 1.2 MPa
Temperature: 50° C.
Agitation: 700 rpm
Time: 7 hours
Volume: 500 ml
Conversion ratio: 100%

FIG. 62 shows HPLC analysis results of the mixture of 1-deoxy L-mannitol and 1-deoxy L-sorbitol after the reduction. In such manner, L-rhamnitol could be produced readily.

Example 32

Production of 1-Deoxy L-Allitol and 1-Deoxy L-Talitol

The reactions are for producing 1-deoxy L-allitol and 1-deoxy L-talitol via the reduction of 1-deoxy L-psicose by a hydrogenation method, which correspond to the reactions D numbered with 19-42 and 19-20, respectively in FIG. 3.

1-Deoxy L-allitol and 1-deoxy L-talitol were produced by reducing 1-deoxy L-psicose produced via the epimerization of 1-deoxy L-fructose under the following reaction conditions. By a general method with the Raney-nickel, these two polyols could be produced at almost equal amounts. FIG. 63 shows HPLC analysis results of the mixture of 1-deoxy L-allitol and 1-deoxy L-talitol after the reduction.

<Reaction Conditions>
Substrate: 5% 1-deoxy L-psicose
Catalyst: nickel
H$_2$ pressure: 1.2 MPa
Temperature: 50° C.
Agitation: 700 rpm
Time: 8 hours
Volume: 500 ml
Conversion ratio: 100%

Using both the deoxy polyols as they are as substrates, 1-deoxy L-psicose and 6-deoxy D-tagatose could be produced via oxidation with an acetic acid bacterium.

INDUSTRIAL APPLICABILITY

The subjects of the invention are monosaccharides. Concerning industrial applications of monosaccharides, monosaccharides are widely used as materials in various fields of foods, cosmetics and pharmaceutical products. In light of the current research and development status about monosaccharides, for example, D-glucose, D-mannose, D-galactose and D-fructose existing abundantly in the natural kingdom are mainly used. So as to promote a new development in the field, therefore, the production of "rare sugars" existing at smaller amounts so far has been needed. The production can be attained via the establishment of methods for producing all monosaccharides on the basis of the strategic Izumoring shown in FIG. 4.

As shown in FIG. 4, monosaccharides include 59 types in total, which are aldose, ketose and polyol. The number of monosaccharides producible at sufficient amounts and industrially applicable is limited. Monosaccharides are superior in that the coordination of OH group bound to carbon therein has such a unique configuration to make such monosaccharides very significant as raw materials for synthetically preparing useful compounds such as pharmaceutical products with chiral structures. Although the usefulness thereof has been understood, not any method for producing such monosaccharides has been attained yet, disadvantageously. In organic chemistry, monosaccharides with chiral structures are superior but synthetic preparation of such monosaccharides with specific chiral structures is very tough. Specifically, the importance in synthetically preparing pharmaceutical products and the like by approaches of organic chemistry means that synthetic preparation of monosaccharides with specific chiral structures by any approach of organic chemistry is very difficult.

On the background of the current status in research and development of these monosaccharides, it has been possible to produce rare sugars mainly including D-psicose and D-allose according to the strategic Izumoring shown in FIG. 4 using biotechnology approaches. A specific chiral structure of a monosaccharide which has never been applicable has now been applicable as a raw material of organic chemistry.

The subjects in accordance with the invention are not the 59 types of monosaccharides as the conventional subjects in FIG. 4 but new sugars in total of 48, which are 1- or 6-deoxyhexoses with 6 carbon atoms as shown in FIG. 1. FIG. 64 shows a list of all deoxy sugars which can be produced on the basis of Deoxy-Izumoring. Eight types of 1-deoxyketose, eight types of 6-deoxyketose, 16 types of 6-deoxyaldose and 16 types of 1- and 6-deoxy polyol (as shown in FIG. 64 in case of polyols, a polyol is expressed with two types of names; when the figure is rotated by 180 degrees, the polyol with the two names can be overlapped together, so these polyols are the same substance) are included in total of 48 types. These deoxy sugars are more hardly prepared synthetically by approaches of organic chemistry than conventional monosaccharides. Using the strategy of Deoxy-Izumoring, these deoxy sugars can be linked together and synthetically prepared by reactions.

The reactions in Deoxy-Izumoring in accordance with the invention are now described below in order. Like reactions in Izumoring, reactions using epimerization, oxidation, isomerization and reduction are also used for Deoxy-Izumoring. Results concerning deoxy sugars are described as regards the individual reactions.

1) Epimerization

As shown in FIG. 4, strategies for all the 59 types could be established by using DTE (D-tagatose 3-epimerase), which first enabled the production of new monosaccharides resulting from the epimerization of the OH group at position 3 in ketose. One of the important issues in accordance with the invention is whether or not DTE has an activity for 1- or 6-deoxyketose. As consequences of our research works, it was confirmed that DTE exerted the action on all of 1- and 6-dexy ketose types. This was an important discovery in accordance with the invention. These reactions correspond to eight epimerization reactions numbered 2-3, 6-7, 10-11, 14-15, 18-19, 22-23, 26-27, and 30-32 in FIG. 3. It could be verified that all these reactions occurred.

2) Oxidation

So as to produce all monosaccharides by completing Izumoring in a ring, polyol plays a major role. In other words, a step of microbially oxidizing polyol at position 2 to produce ketose is essential. Even for producing deoxy sugars in accordance with the invention, namely on the basis of Deoxy-Izumoring, essentially, 1- and 6-deoxyketose should be produced by oxidizing 1- and 6-deoxy polyols with microbial reactions. Because the reaction is a microbial reaction, it is required that deoxy polyol enters into the bacterial cell of a microorganism, where the oxidation of deoxy polyol to deoxyketose mainly with polyol dehydrogenase should occur. As in Izumoring, the reaction at this step should necessarily progress in Deoxy-Izumoring. As results of various investigations, it was confirmed that the use of 1-deoxy polyol and the selection of an appropriate microorganism to establish the reaction conditions therefor could lead to the production of 1- or 6-deoxyketose. The reaction is a totally novel reaction, and it could be verified the presence of a route where a microorganism specifically oxidized 1- and 6-deoxy polyol, namely a route where deoxy polyol was intracelluarly incorporated to specifically oxidize the position 2 or 5 with polyol dehydrogenase to produce 1- or 6-deoxyketose. This enabled the verification that 1- or 6-deoxyketose could be produced according to the Deoxy-Izumoring strategy, using deoxy polyol as the substrate.

3) Isomerization

Isomerization is a redox reaction between carbon-1 and carbon-2 in aldose. By conventional reactions with isomerase, various aldose types could be produced from ketose. In accordance with the invention, it was a key issue whether or not isomerase reacted with 6-deoxyaldose and ketose, as described for DTE. In accordance with the invention, isomerase reactions using various 6-deoxyketoses were investigated, so that various isomerase types used for Izumoring exerted the activity for Deoxy-Izumoring. This apparently shows that 6-deoxyaldose could be produced from various 6-deoxyketoses.

4) Reduction

For a method for reducing ketose to polyol, a process using yeast and a reaction using hydrogen of organic chemistry can be utilized. Currently, a method with hydrogen using a nickel catalyst as an industrially applicable and secure method is advantageous as long as the method can reduce 1- and 6-deoxyketose. In accordance with the invention, reduction reactions using the nickel catalyst were verified. It was revealed that 1- and 6-deoxyketose could be reduced to the individually corresponding 16 types of sugar alcohols by the hydrogenation method as one of conventional methods. Additionally, it was also confirmed that the reduction of 6-deoxyaldose could progress highly efficiently as well.

As shown in the results, it was verified that DTE reacted with 1- and 6-deoxyketose; the microorganism could oxidize deoxy polyol to an intended deoxyketose; isomerase had the corresponding activity and isomerized 6-deoxyketose to 6-deoxyaldose; and the reduction could be applied to the production of 1- and 6-deoxyketose as in the case of general ketose types.

These results apparently show the confirmation that 1- and 6-deoxy sugars conventionally hardly prepared by approaches of organic chemistry can be produced by approaches based on Izumoring. In other words, a method for systematically producing all of a great number of deoxy monosaccharides with chiral structures, which have conventionally never been produced or of which the properties have never been identified, can be established by a new production strategy of Deoxy-Izumoring.

The outcome obtained in accordance with the invention has extremely great industrial meanings in food industries, as well as associated food, cosmetic and pharmaceutical industries.

The invention claimed is:

1. A method for producing deoxyketohexose and a derivative thereof, comprising epimerizing a raw material 1-deoxy D-ketohexose or 6-deoxy D-ketohexose or 1-deoxy L-ketohexose or 6-deoxy L-ketohexose at position 3, using a deoxyketohexose isomerase which is isolated from *Pseudomonas cichorii* ST-24 (FERM BP-2736), to produce the corresponding 1-deoxy D-ketohexose or 6-deoxy D-ketohexose or 1-deoxy L-ketohexose or 6-deoxy L-ketohexose as an intended product.

2. A method for producing deoxyketohexose and a derivative thereof according to claim 1, where the derivative is prepared by reducing deoxyketohexose, the method comprising reducing the intended product 1-deoxy D-ketohexose or 6-deoxy D-ketohexose or 1-deoxy L-ketohexose or 6-deoxy L-ketohexose to generate the corresponding 1-deoxy D-sugar alcohol or 6-deoxy D-sugar alcohol, or 1-deoxy L-sugar alcohol or 6-deoxy L-sugar alcohol as a derivative thereof.

3. A method for producing deoxyketohexose and a derivative thereof according to claim 1, where the derivative is prepared by reducing deoxyketohexose followed by oxidation, the method comprising reducing the intended product 1-deoxy D-ketohexose or 6-deoxy D-ketohexose or 1-deoxy L-ketohexose or 6-deoxy L-ketohexose to generate the corresponding 1-deoxy D-sugar alcohol or 6-deoxy D-sugar alcohol, or 1-deoxy L-sugar alcohol or 6-deoxy L-sugar alcohol as a derivative thereof, and then oxidizing the 1-deoxy D-sugar alcohol or 6-deoxy D-sugar alcohol, or 1-deoxy L-sugar alcohol or 6-deoxy L-sugar alcohol to produce the corresponding 6-deoxy D-ketohexose or 1-deoxy D-ketohexose or 6-deoxy L-ketohexose or 1-deoxy L-ketohexose.

4. A method for producing deoxyketohexose and a derivative thereof according to claim 1, where the derivative is prepared by isomerizing 6-deoxyketohexose, the method comprising allowing aldose isomerase to interact with the intended product 6-deoxy D-ketohexose or 6-deoxy L-ketohexose to produce the corresponding 6-deoxy D-aldohexose or 6-deoxy L-aldohexose as a derivative thereof.

5. A method for producing deoxyketohexose and a derivative thereof according to claim 1, where the derivative is prepared by isomerizing and then reducing deoxyketohexose, the method comprising allowing aldose isomerase to interact with the intended product 6-deoxy D-ketohexose or 6-deoxy L-ketohexose to produce the corresponding 6-deoxy D-aldohexose or 6-deoxy L-aldohexose as a derivative thereof, and allowing aldose reductase to interact with the 6-deoxy D-aldohexose or 6-deoxy L-aldohexose to produce the corresponding 6-deoxy D-sugar alcohol or 6-deoxy L-sugar alcohol.

6. A method for producing deoxyketohexose and a derivative thereof according to claim 1, where 6-deoxy D-ketohexose or 6-deoxy L-ketohexose as a raw material for enzyme interaction is produced by allowing aldose isomerase to interact with 6-deoxy D-aldohexose or 6-deoxy L-aldohexose to produce the corresponding 6-deoxy D-ketohexose or 6-deoxy L-ketohexose, the method additionally comprising epimerizing the product 6-deoxy D-ketohexose or 6-deoxy L-ketohexose to produce the corresponding 6-deoxy D-ketohexose or 6-deoxy L-ketohexose as the intended product.

7. A method for producing deoxyketohexose and a derivative thereof according to claim 1, where 1-deoxy D-ketohexose or 6-deoxy D-ketohexose or 1-deoxy L-ketohexose or 6-deoxy L-ketohexose as a raw material is produced by oxidizing 1-deoxy D-sugar alcohol or 6-deoxy D-sugar alcohol or 1-deoxy L-sugar alcohol or 6-deoxy L-sugar alcohol to produce the corresponding 1-deoxy D-ketohexose or 6-deoxy D-ketohexose or 1-deoxy L-ketohexose or 6-deoxy L-ketohexose, the method additionally comprising epimerizing the resulting product to produce the corresponding 1-deoxy D-ketohexose or 6-deoxy D-ketohexose or 1-deoxy L-ketohexose or 6-deoxy L-ketohexose as the intended product.

8. A method for producing deoxyketohexose and a derivative thereof according to claim 2, where polyol dehydrogenase is used or a hydrogenation process using Raney nickel as a catalyst is used, for the oxidation reaction or reduction reaction.

9. A method according to claim 3, where a bacterial strain IK7 (NITE BP-271) of the genus *Enterobacter* and with a potency of generating dehydrogenase is used for the oxidation reaction.

10. A method for producing deoxyketohexose and a derivative thereof according to claim 1, where the raw material 1- or 6-deoxy D-ketohexose or 1- or 6-deoxy L-ketohexose is produced by allowing aldose reductase to interact with 6-deoxy D-aldohexose or 6-deoxy L-aldohexose or via a reduction reaction of organic chemistry, to produce the corresponding 6-deoxy D-sugar alcohol or 6-deoxy L-sugar alcohol and then oxidizing the resulting sugar alcohol to produce the corresponding 1- or 6-deoxy D-ketohexose or 1- or 6-deoxy L-ketohexose, the method additionally comprising epimerizing the 1- or 6-deoxy D-ketohexose or 1- or 6-deoxy L-ketohexose to produce the corresponding 1- or 6-deoxy D-ketohexose or 1- or 6-deoxy L-ketohexose as the intended product.

11. A method for producing deoxyketohexose and a derivative thereof according to claim 5, where aldose reductase is used or a chemical reduction process is used, for the reduction reaction.

12. A method for producing deoxyketohexose or a derivative thereof according to claim 4, where L-rhamnose isomerase or other aldose isomerase types are used for the isomerization reaction.

13. A method for producing deoxyketohexose and a derivative thereof according to claim 4, where L-rhamnose isomerase or other aldose isomerase types are used for the isomerization reaction for isomerization of 6-deoxy L-psicose to 6-deoxy L-altrose.

* * * * *

UNITED STATES PATENT AND TRADEMARK OFFICE
CERTIFICATE OF CORRECTION

PATENT NO.       : 8,389,248 B2                                                   Page 1 of 1
APPLICATION NO.  : 12/515605
DATED            : March 5, 2013
INVENTOR(S)      : Izumori et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 823 days.

Signed and Sealed this
First Day of September, 2015

Michelle K. Lee
*Director of the United States Patent and Trademark Office*